(12) United States Patent
Dalton et al.

(10) Patent No.: US 12,133,804 B2
(45) Date of Patent: Nov. 5, 2024

(54) TOTAL ANKLE REPLACEMENT SURGICAL METHOD

(71) Applicant: Paragon 28, Inc., Englewood, CO (US)

(72) Inventors: Mark Ray Dalton, Austin, TX (US);
Jeffrey Christensen, Everett, WA (US);
Daniel J. Lee, Denver, CO (US);
Joseph Dogué, Aurora, CO (US);
Francis D. Barmes, Parker, CO (US);
Albert Dacosta, Lone Tree, CO (US);
Aaron Kannard, Los Angeles, CA (US)

(73) Assignee: Paragon 28, Inc., Englewood, CO (US)

( * ) Notice: Subject to any disclaimer, the term of this patent is extended or adjusted under 35 U.S.C. 154(b) by 641 days.

(21) Appl. No.: 17/304,064

(22) Filed: Jun. 14, 2021

(65) Prior Publication Data

US 2021/0298911 A1 Sep. 30, 2021

Related U.S. Application Data

(63) Continuation of application No. PCT/US2019/066404, filed on Dec. 13, 2019, and a
(Continued)

(51) Int. Cl.
*A61F 2/42* (2006.01)
*A61B 17/02* (2006.01)
(Continued)

(52) U.S. Cl.
CPC .......... *A61F 2/4202* (2013.01); *A61B 17/025* (2013.01); *A61B 17/1682* (2013.01);
(Continued)

(58) Field of Classification Search
CPC ......... A61F 2/4202–2002/4207; A61F 2/4684; A61F 2/4657; A61B 17/1682
See application file for complete search history.

(56) References Cited

U.S. PATENT DOCUMENTS

| 3,710,473 A | 1/1973 | McElwain |
|---|---|---|
| 3,750,652 A | 8/1973 | Sherwin |

(Continued)

FOREIGN PATENT DOCUMENTS

| CN | 102405024 | 4/2012 |
|---|---|---|
| CN | 102770067 | 11/2012 |

(Continued)

OTHER PUBLICATIONS

Extended European Search Report for European Application No. 19895228.5, Feb. 27, 2023, 13 pages.
(Continued)

*Primary Examiner* — Zade Coley
(74) *Attorney, Agent, or Firm* — Heslin Rothenberg Farley & Mesiti P.C.; Jacquelyn A. Graff, Esq.

(57) ABSTRACT

Methods for total ankle replacement procedures are disclosed. A method includes making an initial incision, obtaining an alignment guide, performing an alignment, performing a tibia and talar resection, trialing the implant components, performing a talar chamfer resection, and implanting the components.

20 Claims, 70 Drawing Sheets

Related U.S. Application Data continuation of application No. PCT/US2019/066149, filed on Dec. 13, 2019, and a continuation of application No. PCT/US2019/066408, filed on Dec. 13, 2019, and a continuation of application No. PCT/US2019/066398, filed on Dec. 13, 2019, and a continuation of application No. PCT/US2019/066393, filed on Dec. 13, 2019, and a continuation of application No. PCT/US2019/066336, filed on Dec. 13, 2019, and a continuation of application No. PCT/US2019/066409, filed on Dec. 13, 2019, and a continuation of application No. PCT/US2019/065025, filed on Dec. 6, 2019, and a continuation of application No. PCT/US2019/064948, filed on Dec. 6, 2019.

(60) Provisional application No. 62/899,703, filed on Sep. 12, 2019, provisional application No. 62/899,740, filed on Sep. 12, 2019, provisional application No. 62/899,460, filed on Sep. 12, 2019, provisional application No. 62/899,646, filed on Sep. 12, 2019, provisional application No. 62/899,655, filed on Sep. 12, 2019, provisional application No. 62/898,854, filed on Sep. 11, 2019, provisional application No. 62/898,615, filed on Sep. 11, 2019, provisional application No. 62/890,611, filed on Aug. 22, 2019, provisional application No. 62/779,092, filed on Dec. 13, 2018, provisional application No. 62/779,436, filed on Dec. 13, 2018.

(51) Int. Cl.
 A61B 17/16 (2006.01)
 A61F 2/46 (2006.01)
 A61F 2/30 (2006.01)

(52) U.S. Cl.
 CPC ......... *A61F 2/4606* (2013.01); *A61F 2/4684* (2013.01); *A61F 2002/30594* (2013.01); *A61F 2002/4205* (2013.01); *A61F 2002/4207* (2013.01)

(56) References Cited

U.S. PATENT DOCUMENTS

| | | | |
|---|---|---|---|
| 4,899,761 A | 2/1990 | Brown | |
| 5,429,121 A | 7/1995 | Gadelius | |
| 5,628,750 A | 5/1997 | Whitlock | |
| 5,702,464 A | 12/1997 | Lackey | |
| 6,033,440 A | 3/2000 | Schall | |
| 6,241,729 B1 | 6/2001 | Estes | |
| 6,261,296 B1 | 7/2001 | Aebi | |
| 6,551,316 B1 | 4/2003 | Rinner | |
| 6,673,116 B2 | 1/2004 | Reiley | |
| 6,739,068 B1 | 5/2004 | Rinner | |
| 6,875,236 B2 | 4/2005 | Reiley | |
| 7,025,790 B2 | 4/2006 | Parks | |
| 7,153,281 B2 | 12/2006 | Holmes | |
| 7,468,075 B2 | 12/2008 | Ang | |
| 7,534,263 B2 | 5/2009 | Burdulis, Jr. | |
| 7,547,327 B2 | 6/2009 | Collazo | |
| 7,618,451 B2 | 11/2009 | Berez | |
| 7,744,601 B2 | 6/2010 | Rosa | |
| 7,981,158 B2 | 7/2011 | Fitz | |
| 8,002,841 B2 | 8/2011 | Hasselman | |
| 8,062,302 B2 | 11/2011 | Lang | |
| 8,083,745 B2 | 12/2011 | Lang | |
| 8,092,465 B2 | 1/2012 | Metzger | |
| 8,105,330 B2 | 1/2012 | Fitz | |
| 8,114,091 B2 | 2/2012 | Ratron | |
| 8,147,557 B2 | 4/2012 | Lee | |
| 8,357,166 B2 | 1/2013 | Aram | |
| 8,366,771 B2 | 2/2013 | Burdulis, Jr. | |
| 8,439,951 B2 | 5/2013 | Trautwein | |
| 8,460,304 B2 | 6/2013 | Fitz | |
| 8,585,708 B2 | 11/2013 | Fitz | |
| 8,617,172 B2 | 12/2013 | Fitz | |
| 8,657,827 B2 | 2/2014 | Fitz | |
| 8,951,259 B2 | 2/2015 | Fitz et al. | |
| 8,951,260 B2 | 2/2015 | Lang | |
| 8,965,088 B2 | 2/2015 | Tsougarakis et al. | |
| 8,979,866 B2 | 3/2015 | Patel et al. | |
| 9,023,050 B2 | 5/2015 | Lang | |
| 9,066,728 B2 | 6/2015 | Burdulis, Jr. | |
| 9,072,531 B2 | 7/2015 | Fitz et al. | |
| 9,107,680 B2 | 8/2015 | Fitz et al. | |
| 9,125,672 B2 | 9/2015 | Fitz et al. | |
| 9,125,673 B2 | 9/2015 | Fitz et al. | |
| 9,186,161 B2 | 11/2015 | Lang | |
| 9,220,517 B2 | 12/2015 | Lang | |
| 9,220,518 B2 | 12/2015 | Neal | |
| 9,326,780 B2 | 5/2016 | Wong et al. | |
| 9,351,773 B2 | 5/2016 | DiDomenico | |
| 9,358,018 B2 | 6/2016 | Fitz | |
| 9,402,640 B2 | 8/2016 | Reynolds et al. | |
| 9,480,571 B2* | 11/2016 | McGinley | A61F 2/4202 |
| 9,907,561 B2 | 3/2018 | Luna et al. | |
| 9,918,724 B2 | 3/2018 | Luna et al. | |
| 9,974,588 B2 | 5/2018 | Stemniski et al. | |
| 9,993,254 B2 | 6/2018 | Loring et al. | |
| 10,058,335 B2 | 8/2018 | Lee et al. | |
| 10,182,832 B1 | 1/2019 | Saltzman | |
| 10,321,922 B2 | 6/2019 | McGinley et al. | |
| 11,116,521 B2 | 9/2021 | McGinley et al. | |
| 11,337,711 B2 | 5/2022 | Goble et al. | |
| 11,399,949 B2 | 8/2022 | Dogue | |
| 2001/0029377 A1 | 10/2001 | Aebi | |
| 2003/0105467 A1 | 6/2003 | Ralph | |
| 2003/0204265 A1 | 10/2003 | Short | |
| 2003/0225416 A1 | 12/2003 | Bonvallet | |
| 2005/0004676 A1 | 1/2005 | Schon | |
| 2005/0021039 A1 | 1/2005 | Cusick | |
| 2005/0049603 A1 | 3/2005 | Calton | |
| 2005/0070897 A1 | 3/2005 | Petersen | |
| 2005/0267600 A1 | 12/2005 | Haberman | |
| 2005/0288792 A1 | 12/2005 | Landes | |
| 2006/0142870 A1 | 6/2006 | Robinson | |
| 2006/0229730 A1 | 10/2006 | Railey | |
| 2006/0247646 A1 | 11/2006 | Bihary | |
| 2007/0043375 A1 | 2/2007 | Anissian | |
| 2007/0073296 A1 | 3/2007 | Panchbhavi | |
| 2007/0073405 A1 | 3/2007 | Verhulst | |
| 2007/0100347 A1 | 5/2007 | Stad | |
| 2007/0123904 A1 | 5/2007 | Stad | |
| 2007/0173858 A1 | 7/2007 | Engh | |
| 2007/0270783 A1 | 11/2007 | Zumsteg | |
| 2008/0015599 A1 | 1/2008 | D'Alessio | |
| 2008/0082169 A1 | 4/2008 | Gittings | |
| 2008/0103603 A1 | 5/2008 | Hintermann | |
| 2008/0114369 A1 | 5/2008 | Bastian | |
| 2008/0269757 A1 | 10/2008 | McMinn | |
| 2009/0182433 A1* | 7/2009 | Reiley | A61B 17/1775 623/18.11 |
| 2009/0209964 A1 | 8/2009 | Yeung | |
| 2009/0234360 A1 | 9/2009 | Alexander | |
| 2009/0312807 A1 | 12/2009 | Boudreault | |
| 2010/0121334 A1 | 5/2010 | Couture | |
| 2010/0161077 A1 | 6/2010 | Boone | |
| 2010/0217338 A1 | 8/2010 | Carroll | |
| 2010/0331848 A1 | 12/2010 | Smith | |
| 2011/0208093 A1 | 8/2011 | Gross | |
| 2011/0218542 A1 | 9/2011 | Lian | |
| 2011/0218543 A1 | 9/2011 | van der Walt | |
| 2012/0053592 A1 | 3/2012 | Burgi | |
| 2012/0101504 A1 | 4/2012 | Habegger | |
| 2012/0130376 A1* | 5/2012 | Loring | A61B 17/1682 606/90 |
| 2012/0130434 A1 | 5/2012 | Stemniski | |
| 2012/0158152 A1 | 6/2012 | Claypool | |
| 2012/0232558 A1 | 9/2012 | Berberich | |
| 2012/0239045 A1 | 9/2012 | Li | |
| 2012/0259335 A1 | 10/2012 | Scifert | |

(56) References Cited

U.S. PATENT DOCUMENTS

| | | |
|---|---|---|
| 2012/0271314 A1 | 10/2012 | Stemniski |
| 2012/0277745 A1 | 11/2012 | Lizee |
| 2013/0046313 A1 | 2/2013 | Lian |
| 2013/0060253 A1 | 3/2013 | Couture |
| 2013/0085499 A1* | 4/2013 | Lian ................. A61F 2/4202 606/87 |
| 2013/0088549 A1 | 4/2013 | Loring |
| 2013/0116797 A1 | 5/2013 | Coulange et al. |
| 2014/0018931 A1 | 1/2014 | Gillard |
| 2014/0025127 A1 | 1/2014 | Richter |
| 2014/0128979 A1 | 5/2014 | Womble et al. |
| 2014/0163563 A1 | 6/2014 | Reynolds et al. |
| 2014/0180426 A1 | 6/2014 | Lian |
| 2014/0188236 A1* | 7/2014 | McGinley ........... A61F 2/4684 623/21.18 |
| 2014/0236157 A1 | 8/2014 | Tochigi et al. |
| 2014/0336658 A1* | 11/2014 | Luna ................. A61B 17/15 606/87 |
| 2014/0371865 A1 | 12/2014 | Firestone |
| 2015/0157339 A1 | 6/2015 | McGinley |
| 2015/0182273 A1* | 7/2015 | Stemniski ......... A61B 17/1739 606/96 |
| 2015/0265265 A1 | 9/2015 | Hynes et al. |
| 2015/0282952 A1 | 10/2015 | Hes |
| 2015/0305753 A1 | 10/2015 | McGinley et al. |
| 2015/0313727 A1 | 11/2015 | Waite, II |
| 2015/0320567 A1 | 11/2015 | Terrill et al. |
| 2015/0359642 A1 | 12/2015 | Claypool et al. |
| 2016/0074053 A1 | 3/2016 | Hutchinson |
| 2016/0135815 A1 | 5/2016 | Loring |
| 2016/0278754 A1 | 9/2016 | Todorov |
| 2016/0367269 A9 | 12/2016 | McGinley et al. |
| 2017/0027589 A1* | 2/2017 | Loring ................. A61B 17/15 |
| 2017/0079670 A1 | 3/2017 | Haines |
| 2017/0100140 A1* | 4/2017 | Stemniski ......... A61B 17/1717 |
| 2017/0112586 A1 | 4/2017 | Dhupar |
| 2017/0238946 A1 | 8/2017 | van der Walt et al. |
| 2017/0258526 A1* | 9/2017 | Lang ................. A61B 17/157 |
| 2017/0290597 A1 | 10/2017 | Goble |
| 2017/0296158 A1* | 10/2017 | Loring ................. A61B 17/15 |
| 2017/0296208 A1* | 10/2017 | Lian ................. A61F 2/4202 |
| 2017/0340450 A1 | 11/2017 | Toro Arbelaez |
| 2017/0354425 A1 | 12/2017 | Zaima |
| 2018/0125663 A1 | 5/2018 | Huxel et al. |
| 2018/0146970 A1 | 5/2018 | Luna et al. |
| 2018/0168826 A1 | 6/2018 | van der Walt et al. |
| 2018/0177511 A1 | 6/2018 | Luna et al. |
| 2018/0177513 A1 | 6/2018 | Stemniski et al. |
| 2018/0221074 A1 | 8/2018 | Dacosta et al. |
| 2018/0243023 A1 | 8/2018 | Stemniski et al. |
| 2018/0263639 A1 | 9/2018 | McGinley |
| 2018/0280038 A1 | 10/2018 | Goble |
| 2018/0280069 A1 | 10/2018 | Barmes et al. |
| 2018/0289380 A1 | 10/2018 | Mauldin et al. |
| 2018/0303490 A1 | 10/2018 | Loring et al. |
| 2018/0317940 A1 | 11/2018 | Stemniski et al. |
| 2019/0133612 A1 | 5/2019 | McGinley et al. |
| 2020/0046412 A1 | 2/2020 | Nachtrab et al. |
| 2020/0085452 A1 | 3/2020 | Siegler |
| 2020/0113712 A1 | 4/2020 | Luna et al. |

FOREIGN PATENT DOCUMENTS

| | | |
|---|---|---|
| CN | 107361883 | 11/2017 |
| CN | 108969162 | 12/2018 |
| EP | 1260183 | 11/2002 |
| FR | 2700462 | 7/1994 |
| JP | 2004130109 | 4/2004 |
| JP | 2011115440 | 6/2011 |
| JP | 5379966 | 12/2013 |
| KR | 1020180108949 | 10/2018 |
| WO | 2000069373 | 11/2000 |
| WO | 2005048851 | 6/2005 |
| WO | 2010122034 | 10/2010 |
| WO | 2014152535 | 9/2014 |
| WO | 2017164862 | 9/2017 |
| WO | 2019063807 | 4/2019 |
| WO | 2019091537 | 5/2019 |
| WO | 2019213122 | 11/2019 |
| WO | 2020123295 | 6/2020 |
| WO | 2020123899 | 6/2020 |
| WO | 2020124047 | 6/2020 |
| WO | 2020124052 | 6/2020 |
| WO | 2020124056 | 6/2020 |

OTHER PUBLICATIONS

Schweitzer et al., Total Ankle Arthroplasty with a Modern Fixed-Bearing System: The Salto Talaris Prosthesis, JBJS Essential Surgical Techniques, retrieved from the internet at https://www.ncbi.nlm.nih.gov/pmc/articles/PMC6407948/pdf/jbjsest-3-e18.pdf, 9 pages, 2013.

International Search Report and Written Opinion of the International Searching Authority for PCT/US2019/066409, Feb. 10, 2020, 20 pages.

Extended European Search Report issued in European Patent Application No. 9896955.2, 9 pages Oct. 21, 2022.

Non-Final Office Action issued in U.S. Appl. No. 17/345,135, Dec. 9, 2021, 16 pages.

Non-Final Office Action issued in U.S. Appl. No. 17/345,137, Nov. 15, 2021, 14 pages.

Non-Final Office Action issued in U.S. Appl. No. 17/345,402, Feb. 1, 2022, 17 pages.

* cited by examiner

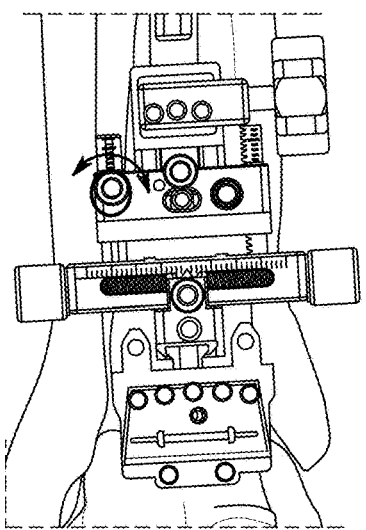
FIG. 33
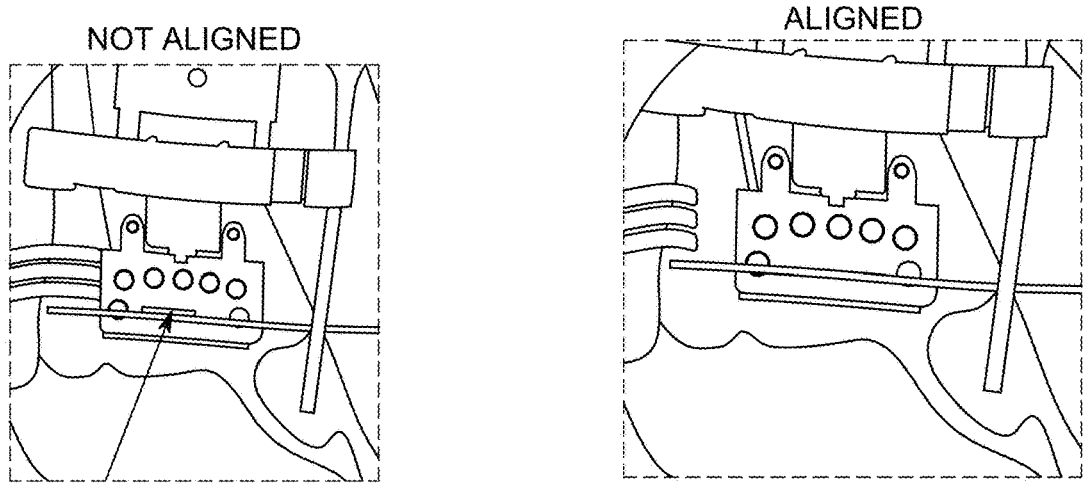
FIG. 34
FIG. 35
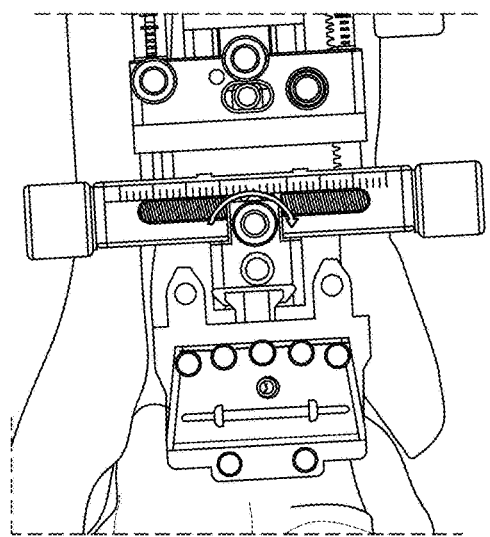
FIG. 36

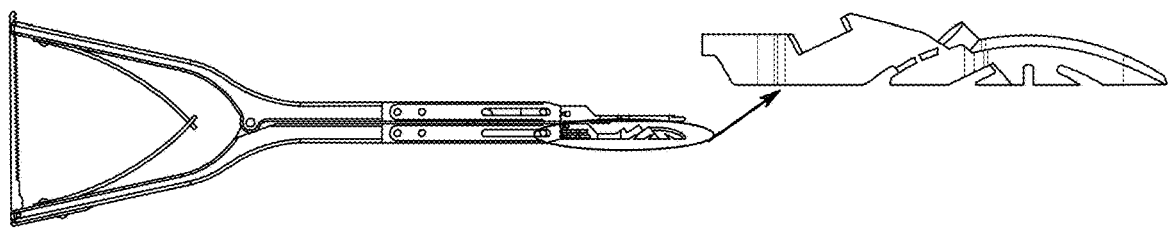
FIG. 64
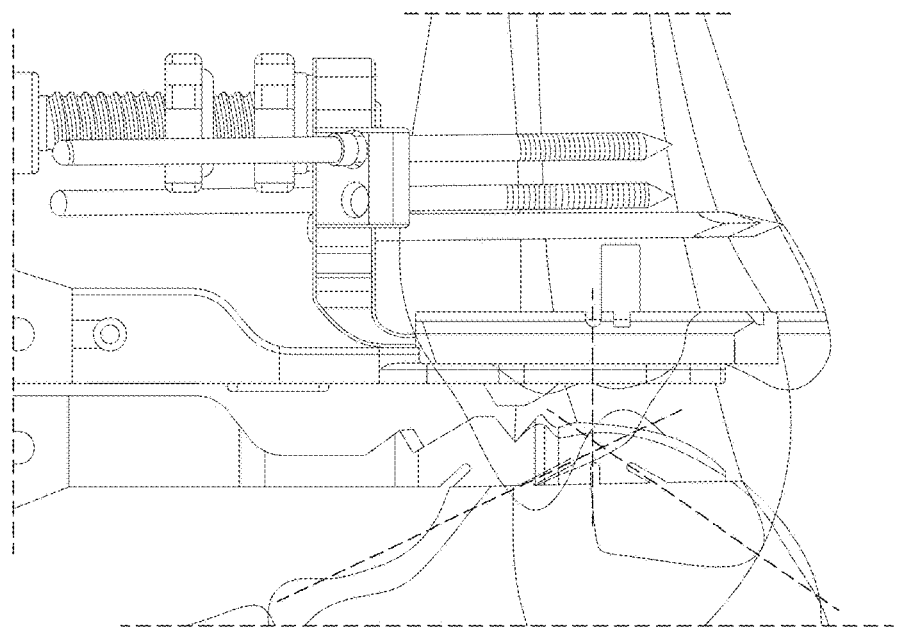
FIG. 65
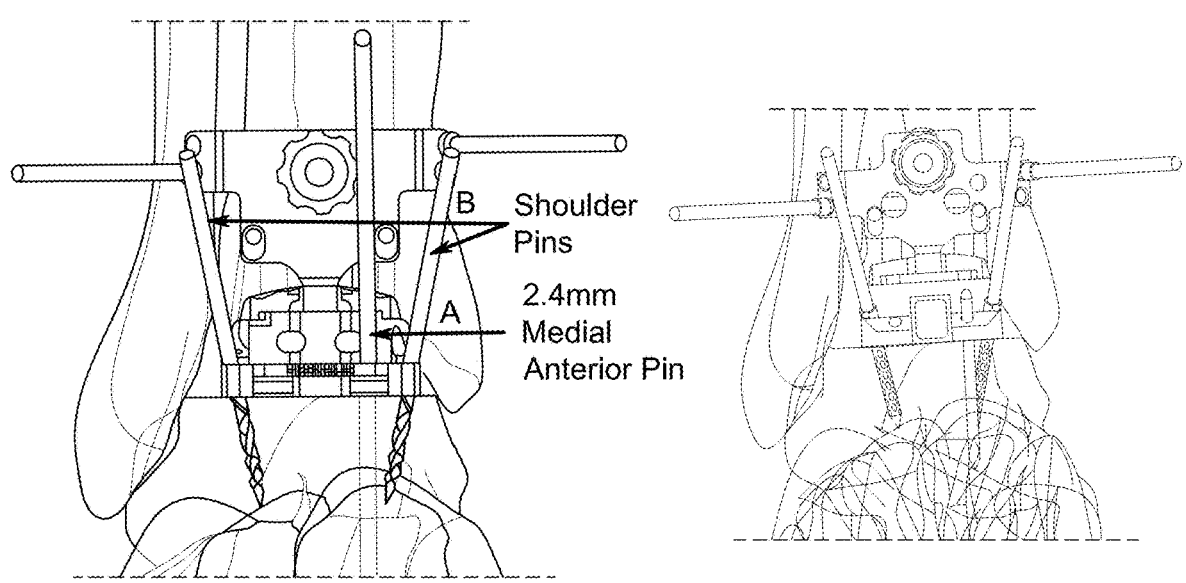
FIG. 66
FIG. 67

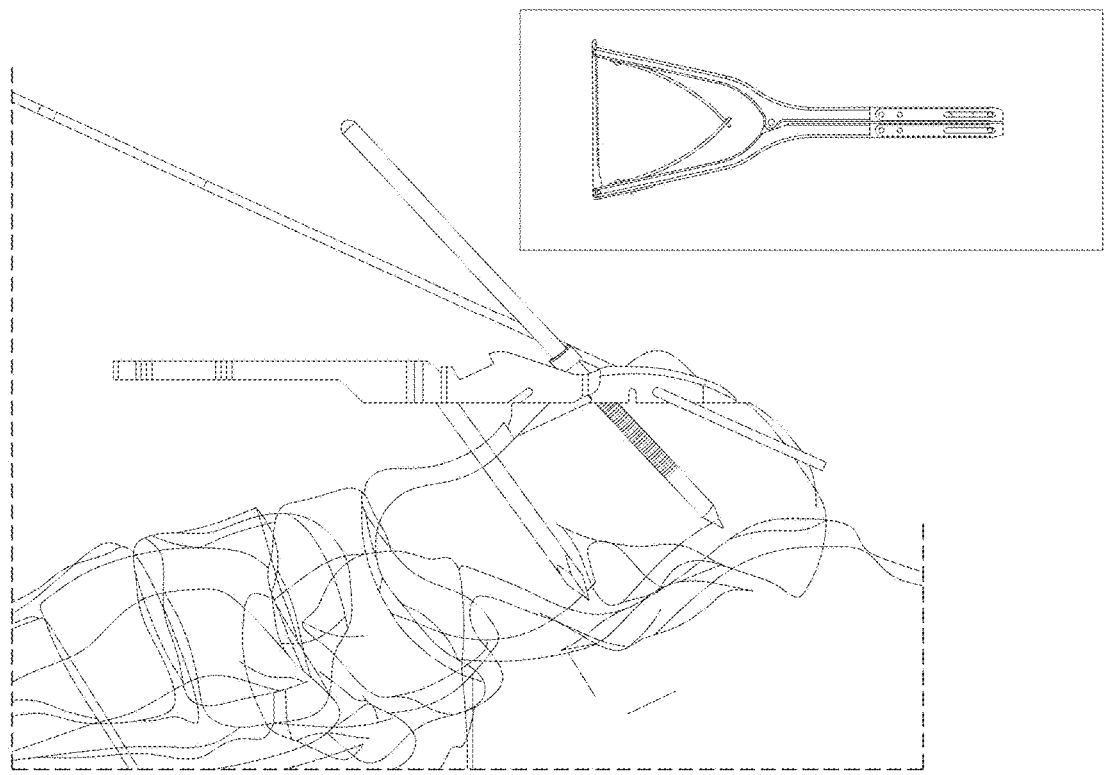
FIG. 68
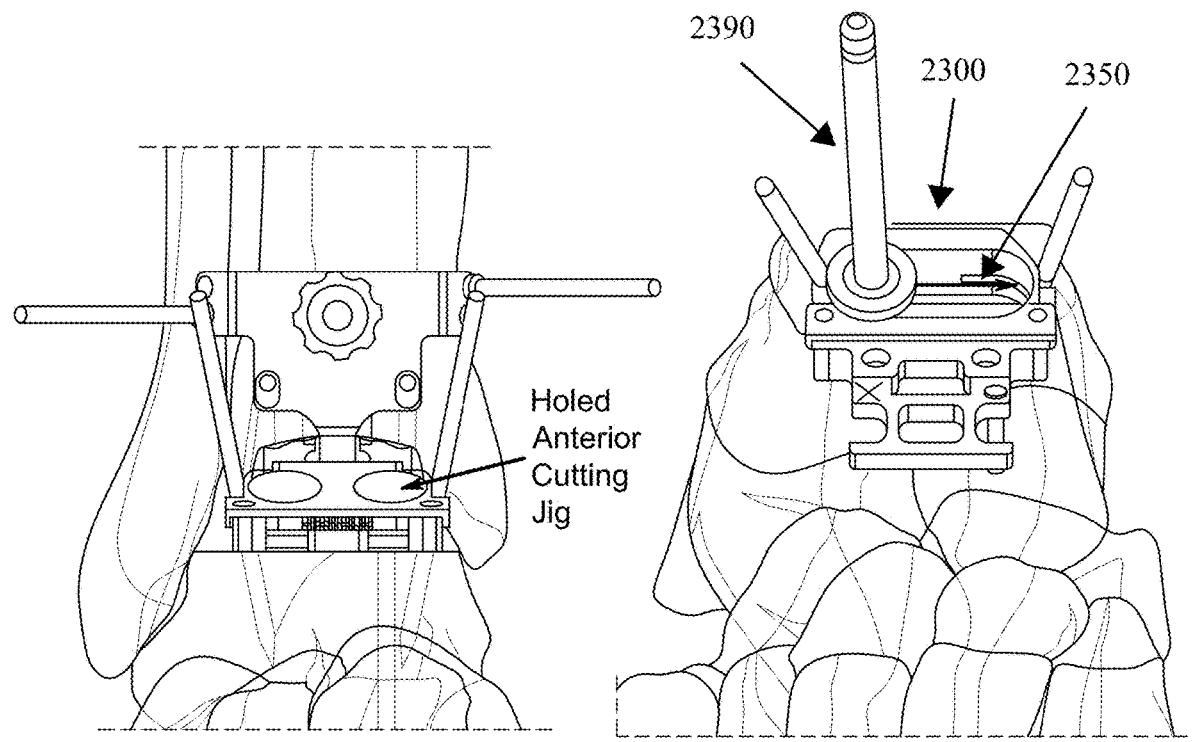
FIG. 69
FIG. 70

Laser Marked Converging Holes

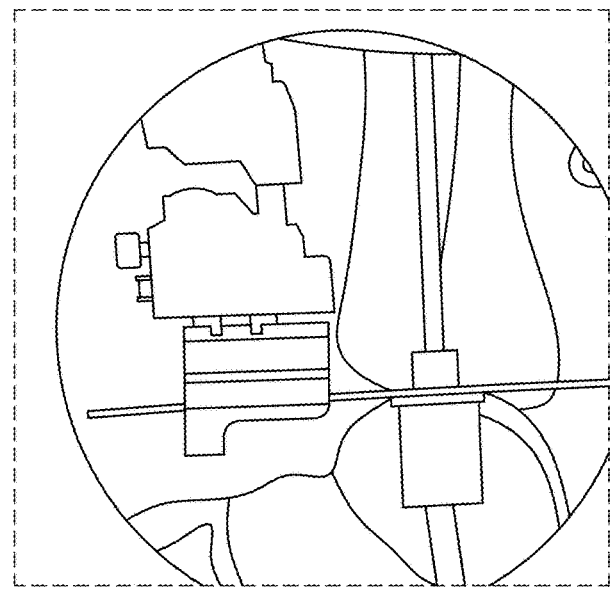
FIG. 130
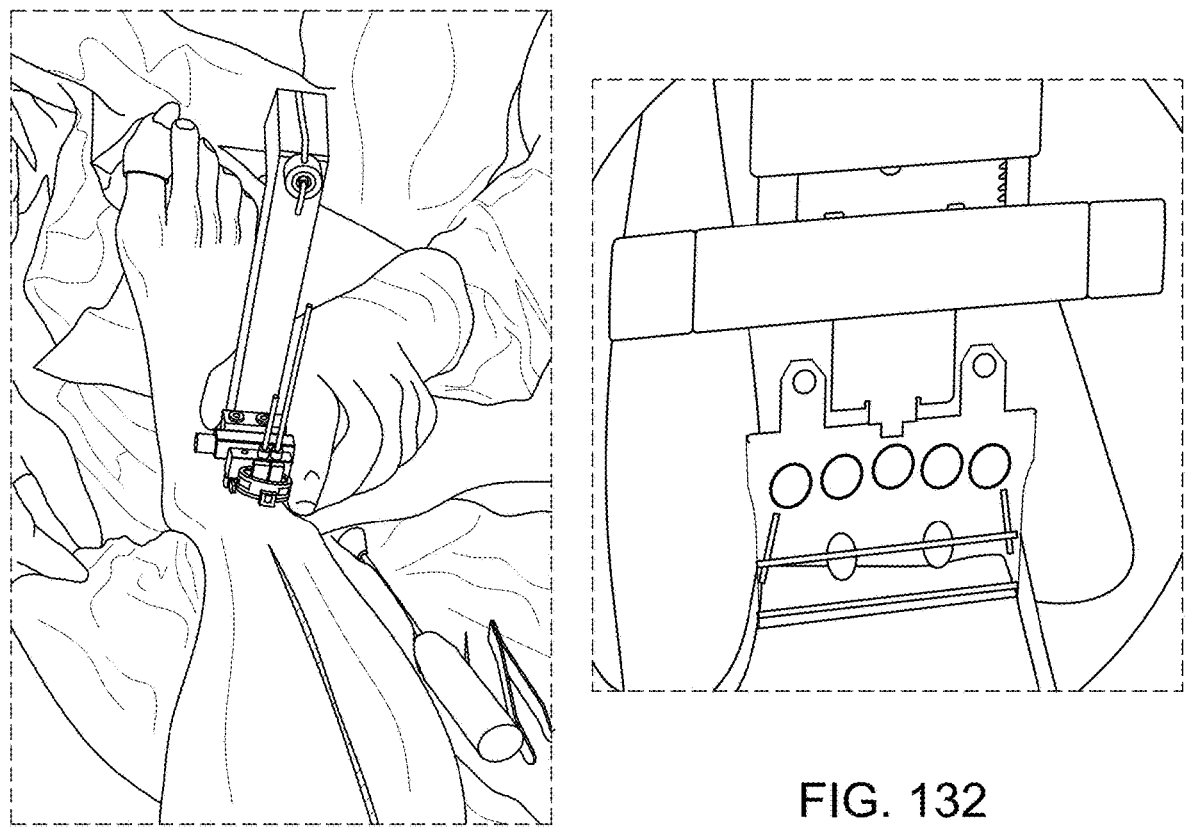
FIG. 131
FIG. 132

Sizing Resection Block

TOTAL ANKLE REPLACEMENT SURGICAL METHOD

CROSS REFERENCE TO RELATED APPLICATIONS

This application is a continuation of PCT/US2019/066409 filed on Dec. 13, 2019 and entitled Total Ankle Replacement Surgical Method, which claims priority benefit to U.S. Provisional Application No. 62/899,460 filed Sep. 12, 2019 and entitled Total Ankle Replacement Surgical Method and which also claims priority benefit to U.S. Provisional Application No. 62/779,436 filed Dec. 13, 2018 and entitled Joint Replacement Systems and Methods of Use and Assembly, which are each hereby incorporated herein in their entireties.

This application is also a continuation of International Application No. PCT/US2019/029009 filed Apr. 24, 2019 and entitled Implants and Methods of Use and Assembly, which claims priority benefit to U.S. Provisional Application No. 62/661,945 filed Apr. 24, 2018 and entitled Implants and Methods of Use and Assembly, which are each hereby incorporated herein in their entireties.

This application is also a continuation of International Application No. PCT/US2019/066404 filed Dec. 13, 2019 and entitled Instruments, Guides and Related Methods for Total Ankle Replacement, which claims priority benefit to U.S. Provisional Application No. 62/779,092 filed Dec. 13, 2018 and entitled Instruments, Guides and Related Methods for Total Ankle Replacement, and which also claims priority benefit to U.S. Provisional Application No. 62/898,854 filed Sep. 11, 2019 and entitled Distractors Having Attachable Paddles, Impaction Devices, and Methods for Use in Total Ankle Replacement, which are each hereby incorporated herein in their entireties.

This application is also a continuation of International Application No. PCT/US2019/066336 filed Dec. 13, 2019 and entitled Patient Specific Instruments and Methods of Use, which claims priority benefit to U.S. Provisional Application No. 62/890,611 filed Aug. 22, 2019 and entitled Patient Specific Instruments and Methods of Use, and which also claims priority benefit to U.S. Provisional Application No. 62/779,436 filed Dec. 13, 2018 and entitled Joint Replacement Systems and Methods of Use and Assembly, which are each hereby incorporated herein in their entireties.

This application is also a continuation of International Application No. PCT/US2019/066408 filed Dec. 13, 2019 and entitled Joint Replacement Alignment Guides, Systems and Methods of Use and Assembly, which claims priority benefit to U.S. Provisional Application No. 62/899,703 filed Sep. 12, 2019 and entitled Joint Replacement Alignment Guides, Systems and Methods of Use and Assembly, and which also claims priority benefit to U.S. Provisional Application No. 62/779,436 filed Dec. 13, 2018 and entitled Joint Replacement Systems and Methods of Use and Assembly, and which also claims priority benefit to U.S. Provisional Application No. 62/899,655 filed Sep. 12, 2019 and entitled Alignment Instruments and Methods for Use in Total Ankle Replacement, and which also claims priority benefit to U.S. Provisional Application No. 62/899,740 filed Sep. 12, 2019 and entitled Joint Replacement Alignment Guides, Systems and Methods of Use and Assembly, which are each hereby incorporated herein in their entireties.

This application is also a continuation of International Application No. PCT/US2019/066149 filed Dec. 13, 2019 and entitled Alignment Instruments and Methods for Use in Total Ankle Replacement, which claims priority benefit to U.S. Provisional Application No. 62/899,655 filed Sep. 12, 2019 and entitled Alignment Instruments and Methods for Use in Total Ankle Replacement, and which also claims priority benefit to U.S. Provisional Application No. 62/779,436 filed Dec. 13, 2018 and entitled Joint Replacement Systems and Methods of Use and Assembly, which are each hereby incorporated herein in their entireties.

This application is also a continuation of International Application No. PCT/US2019/066393 filed Dec. 13, 2019 and entitled Joint Replacement Alignment Guides, Systems and Methods of Use and Assembly, which claims priority benefit to U.S. Provisional Application No. 62/899,740 filed Sep. 12, 2019 and entitled Joint Replacement Alignment Guides, Systems and Methods of Use and Assembly, and which also claims priority benefit to U.S. Provisional Application No. 62/899,703 filed Sep. 12, 2019 and entitled Joint Replacement Alignment Guides, Systems and Methods of Use and Assembly, and which also claims priority benefit to U.S. Provisional Application No. 62/779,436 filed Dec. 13, 2018 and entitled Joint Replacement Systems and Methods of Use and Assembly, and which also claims priority benefit to U.S. Provisional Application No. 62/899,655 filed Sep. 12, 2019 and entitled Alignment Instruments and Methods for Use in Total Ankle Replacement, which are each hereby incorporated herein in their entireties.

This application is also a continuation of International Application No. PCT/US2019/064948 filed Dec. 6, 2019 and entitled Resection Guides, Sweeping Reamers, and Methods for Use in Total Ankle Replacement, which claims priority benefit to U.S. Provisional Application No. 62/898,615 filed Sep. 11, 2019 and entitled Resection Guides, Sweeping Reamers, and Methods for Use in Total Ankle Replacement, and which also claims priority benefit to U.S. Provisional Application No. 62/779,436 filed Dec. 13, 2018 and entitled Joint Replacement Systems and Methods of Use and Assembly, which are each hereby incorporated herein in their entireties.

This application is also a continuation of International Application No. PCT/US2019/066398 filed Dec. 13, 2019 and entitled Distractors Having Attachable Paddles, Impaction Devices, and Methods for Use in Total Ankle Replacement, which claims priority benefit to U.S. Provisional Application No. 62/898,854 filed Sep. 11, 2019 and entitled Distractors Having Attachable Paddles, Impaction Devices, and Methods for Use in Total Ankle Replacement, and which also claims priority benefit to U.S. Provisional Application No. 62/779,092 filed Dec. 13, 2018 and entitled Instruments, Guides and Related Methods for Total Ankle Replacement, and which also claims priority benefit to U.S. Provisional Application No. 62/779,436 filed Dec. 13, 2018 and entitled Joint Replacement Systems and Methods of Use and Assembly, which are each hereby incorporated herein in their entireties.

This application is also a continuation of International Application No. PCT/US2019/065025 filed Dec. 6, 2019 and entitled Trial Insert Assembly, which claims priority benefit to U.S. Provisional Application No. 62/899,646 filed Sep. 12, 2019 and entitled Trial Insert Assembly, and which also claims priority benefit to U.S. Provisional Application No. 62/779,092 filed Dec. 13, 2018 and entitled Instruments, Guides and Related Methods for Total Ankle Replacement, and which also claims priority benefit to U.S. Provisional Application No. 62/779,436 filed Dec. 13, 2018 and entitled Joint Replacement Systems and Methods of Use and Assembly, which are each hereby incorporated herein in their entireties.

TECHNICAL FIELD

The present disclosure relates generally to general, podiatric, and orthopaedic surgery related to joint deformities. More specifically, but not exclusively, the present disclosure relates to implants, devices, instruments, systems and methods for maintaining, correcting and/or resurfacing joint surfaces.

BACKGROUND OF THE INVENTION

Currently available implants for total ankle replacement ("TAR") may experience loosening of the tibial component. In addition, some currently available implants for total ankle replacement may cause stress concentrations in the medial malleolus. In other currently available implants for total ankle replacement, the sizing of the talus component lacks proper bone coverage. Finally, some currently available implants for total ankle replacement lack vertical stabilization features on the tibia.

Accordingly, it is an object of the present invention to overcome one or more of the above-described drawbacks and/or disadvantages of the currently used implants. For example, in view of the deficiencies of the current implants, it would be desirable to develop implants, devices, and/or systems which avoid loosening of the tibial component, remove the stress concentration from the medial malleolus, provide proper coverage of the talus bone, and provide features for vertical stabilization of the tibia.

SUMMARY OF THE INVENTION

The present disclosure is directed toward implants, devices and methods for use in maintaining, correcting and/or resurfacing joint surfaces.

In one aspect of the present disclosure provided herein, is a method for total ankle replacement. The method including placing an alignment guide on the patient's leg, performing the initial resection of the ankle, performing trialing of implants and a chamfer resection of the talus, performing final trialing of implants, preparing implant components, and implanting components.

In another aspect of the present disclosure provided herein, is an alternative method for total ankle replacement. The method further including performing a joint-line referencing ("JLR") fast-track alignment.

In yet another aspect of the present disclosure provided herein, is an alternative method for total ankle replacement. The method further including performing a decoupled talar resection.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying figures/flow charts, which are incorporated in and constitute a part of the specification, illustrate embodiments of the disclosure and together with the detailed description herein, serve to explain the principles of the disclosure. The figures/flow charts are only for purposes of illustrating preferred embodiments and are not to be construed as limiting the disclosure.

FIGS. 128-132 is a portion of the method of FIG. 24 using a patient specific alignment guide, in accordance with an aspect of the present disclosure.

DETAILED DESCRIPTION FOR CARRYING OUT THE INVENTION

Figure 1:
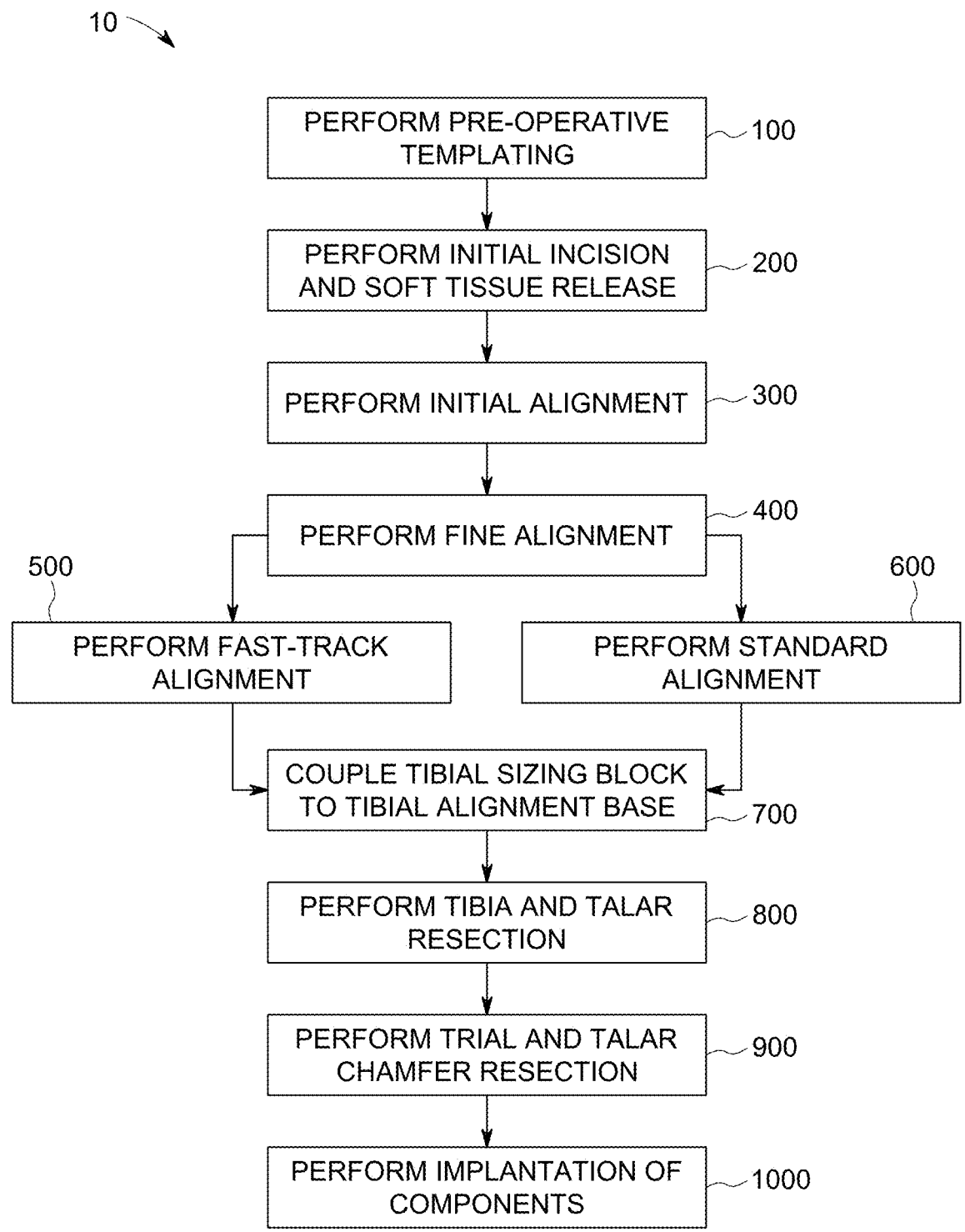
FIG. 1 is a flow chart illustrating an embodiment of a method for total ankle replacement, in accordance with an aspect of the present disclosure.

Generally stated, disclosed herein are methods for total ankle replacement surgery.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Referring to the drawings, wherein like reference numerals are used to indicate like or analogous steps throughout the several methods, and with particular reference to FIGS. 1-23, methods of a total ankle replacement ("TAR") procedure are illustrated.

Referring now to FIG. 1, the total ankle replacement procedure 10 may include, for example, a pre-operative templating procedure 100, an initial incision and soft tissue release procedure 200, an initial alignment procedure 300, a fine alignment procedure 400, either a fast-track alignment procedure 500 or a standard alignment procedure 600, a tibial sizing block and tibial alignment base coupling procedure 700, a tibia and talar resection procedure 800, a trialing and talar chamfer resection procedure 900, and an implantation procedure 1000.

Figure 2:
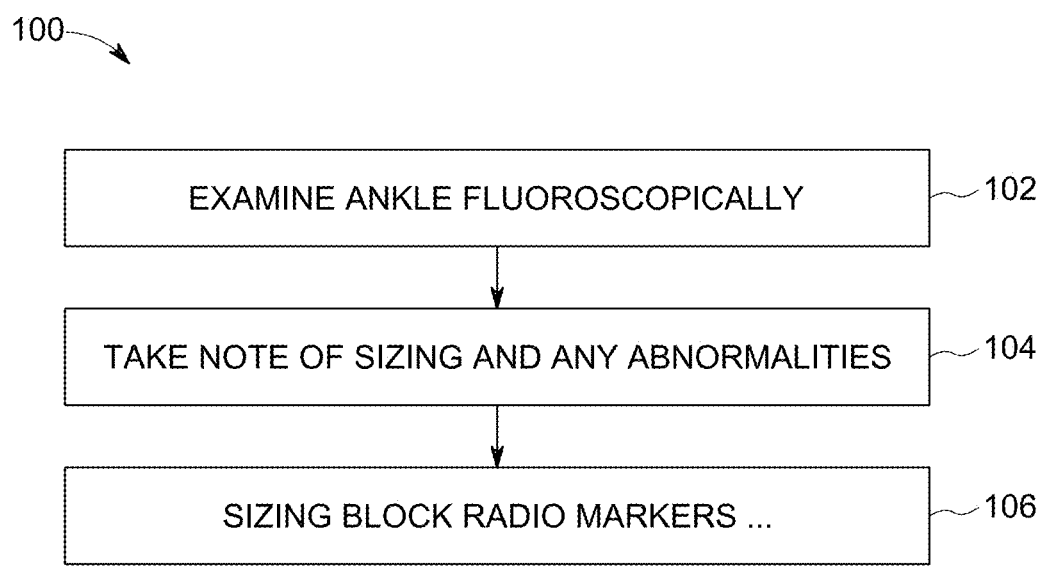
FIG. 2 is a flow chart illustrating a portion of the method of FIG. 1 for pre-operative templating, in accordance with an aspect of the present disclosure.

Referring now to FIG. 2, a pre-operative templating procedure 100 for TAR surgery is illustrated. The ankle is examined fluoroscopically 102 and the sizing block radio markers may be used to take note of sizing and any abnormalities.

Figure 3:
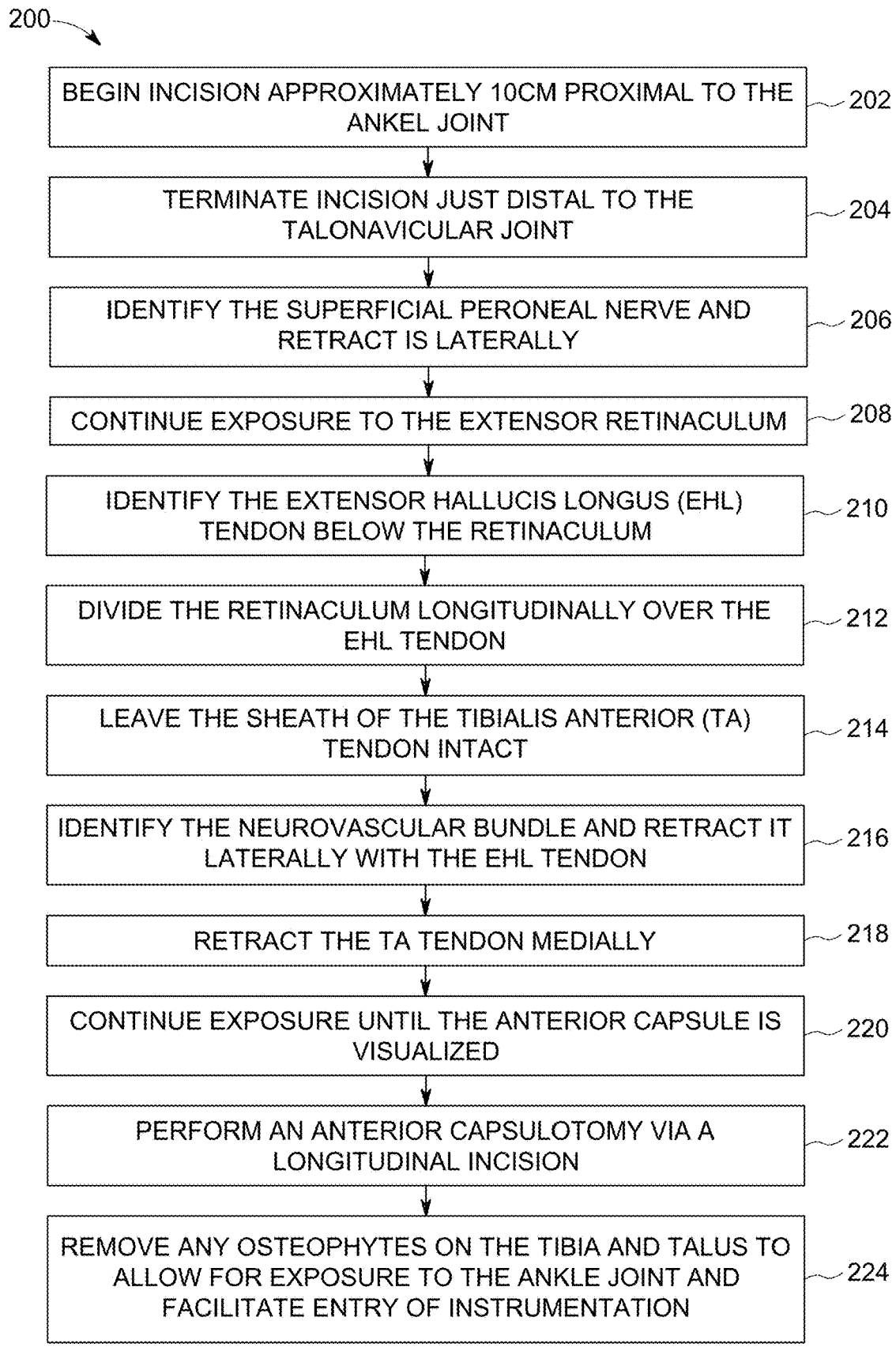
FIG. 3 is a flow chart illustrating a portion of the method of FIG. 1 for initial incision and soft tissue release, in accordance with an aspect of the present disclosure.

FIG. 3 illustrates an initial incision and soft tissue release procedure 200. The procedure may include, for example, making an incision and exposing the patient's joint. The incision may be made, for example, over the anterior ankle, approximately 10 cm proximal to the ankle joint 202 and terminating distal to the talonavicular joint 204. In addition, the incision may be started, for example, lateral to the tibial crest and lateral to the tibialis anterior tendon. The initial incision should be made, for example, to only penetrate skin, then the superficial peroneal nerve should be identified and retracted laterally 206. The exposure should continue to the extensor retinaculum 208 and the extensor hallucis longus (EHL) tendon should be identified 210. The retinaculum may then be divided longitudinally over the extensor hallucis longus tendon 212 and the sheath of the tibialis anterior (TA) tendon should be left intact 214. Next, identify the neurovascular bundle and retract is laterally with the EHL tendon 216. Then, retract the TA tendon medially 218. The exposure may continue until the anterior capsule is visualized 220. Once the anterior capsule is visualized, an anterior capsulotomy may be performed via a longitudinal incision 222. Then, the capsule and periosteum may be elevated over the anterior tibia and talus to expose the anterior ankle joint, the tibial plafond, the medial and lateral gutters, and the anterior and dorsal talus. If necessary, osteophytes on the tibia and talus may be removed to allow for exposure of the ankle joint and to facilitate entry of the alignment guide instrumentation 224.

Figure 4:
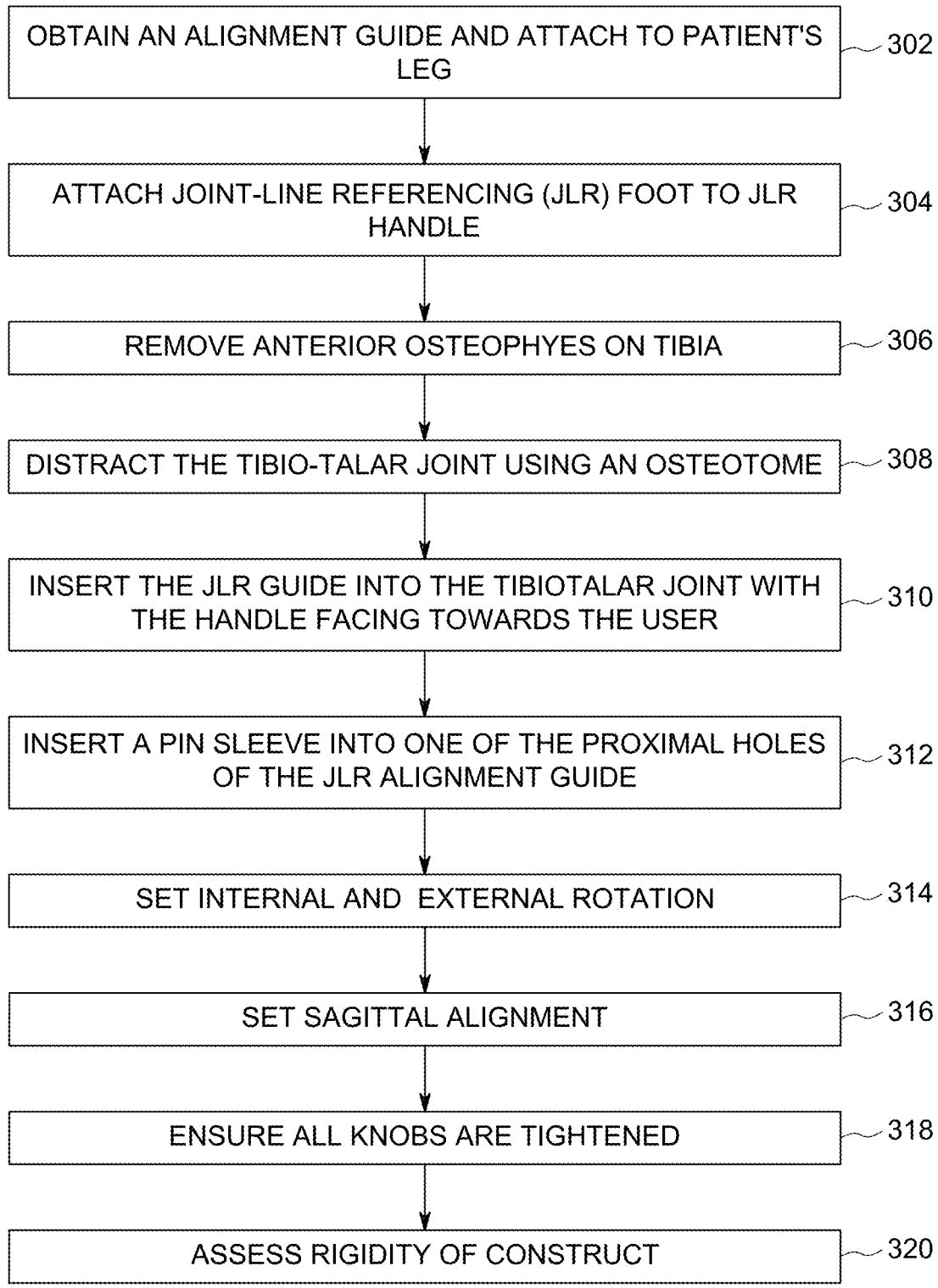
FIG. 4 is a flow chart illustrating a portion of the method of FIG. 1 for initial alignment and inserting a pin sleeve, in accordance with an aspect of the present disclosure.

As shown in FIG. 4, after the patient's joint is exposed, the method may then include an initial alignment procedure 300. The joint may be aligned using a joint line referencing alignment guide and attaching said alignment guide to the patient's leg 302. The joint line referencing alignment guide may include a joint line referencing foot coupled to a joint line referencing handle. A joint line referencing foot may be selected that most closely corresponds to the shape of the talus, for example, flat, rounded, curved, arced or the like. The selected joint line referencing foot may then be coupled to the joint line referencing handle 304. The joint line referencing alignment guide may be, for example, the type described in U.S. Provisional Application No. 62/899,655 filed Sep. 12, 2018 and entitled Alignment Instruments and Methods for Use in Total Ankle Replacement, which is hereby incorporated by reference in its entirety. Next, if necessary, anterior osteophytes on the tibia may be removed 306. The tibio-talar joint may then be distracted and the joint line referencing foot may be inserted into the tibio-talar joint with the handle facing towards the user. The tibio-talar joint may be opened using, for example, an osteotome or other like instrument to separate the joint 308. The joint line referencing alignment guide may be inserted into the tibotalar joint with the handle facing towards the user 310. A sleeve or pin sleeve may be inserted into one of the proximal holes of the joint line referencing handle 312. After the joint line referencing foot is inserted into the tibo-talar joint, the internal/external rotation may be set 314 by, for example, aligning the joint line referencing handle to the second metatarsal. The sagittal alignment may also be set 316 by, for example, positioning the alignment arm parallel to the tibial crest. Once the alignment is set with respect to the tibial crest, a pin may be inserted through the pin sleeve and into the tibia to fix the position of the joint line referencing alignment guide. Next, the method may include ensuring all knobs are tightened 318 and assessing the rigidity of the construct 320.

Figure 5:
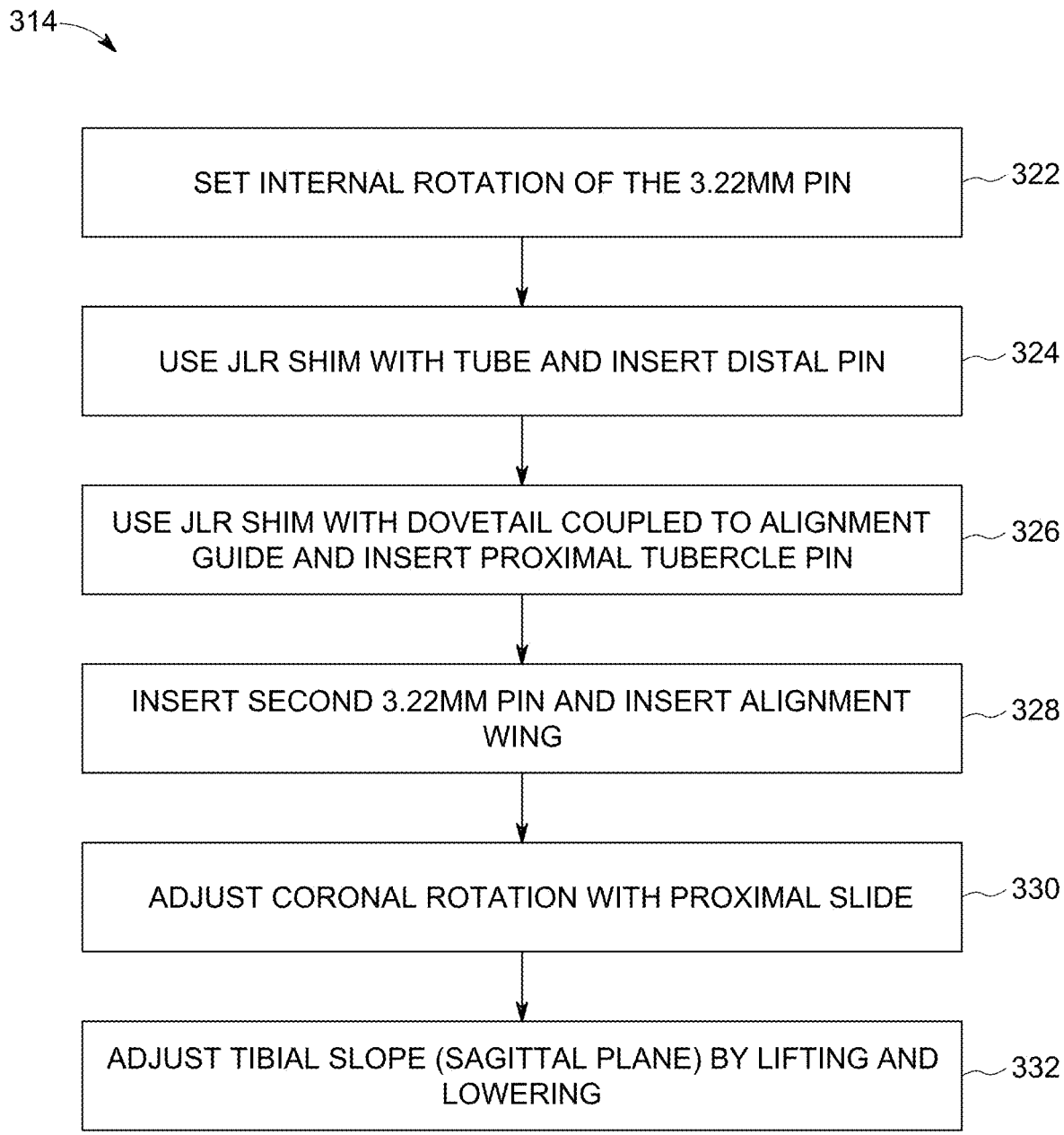
FIG. 5 is a flow chart illustrating a portion of the method of FIG. 4 for internal and external rotation, in accordance with an aspect of the present disclosure.

As shown in FIG. 5, setting the internal/external rotation 314 may include, for example, setting the internal rotation of the pin 322, using the joint line referencing shim with a tube and inserting the distal pin 324, or using the joint line referencing shim with a dovetail coupled to alignment guide and inserting a proximal tubercle pin 326. A second pin and an alignment wing may be inserted 328. Then, the coronal rotation may, for example, be set using the proximal slide 330. The tibial slope may be, for example, adjusted by lifting and lowering the front handle of a joint line pointer of the joint line referencing alignment guide 332. When the handle of the joint line pointer is "lifted" the tibial slope is opening and when the handle is "lowered" the tibial slope is closing.

Figure 6:
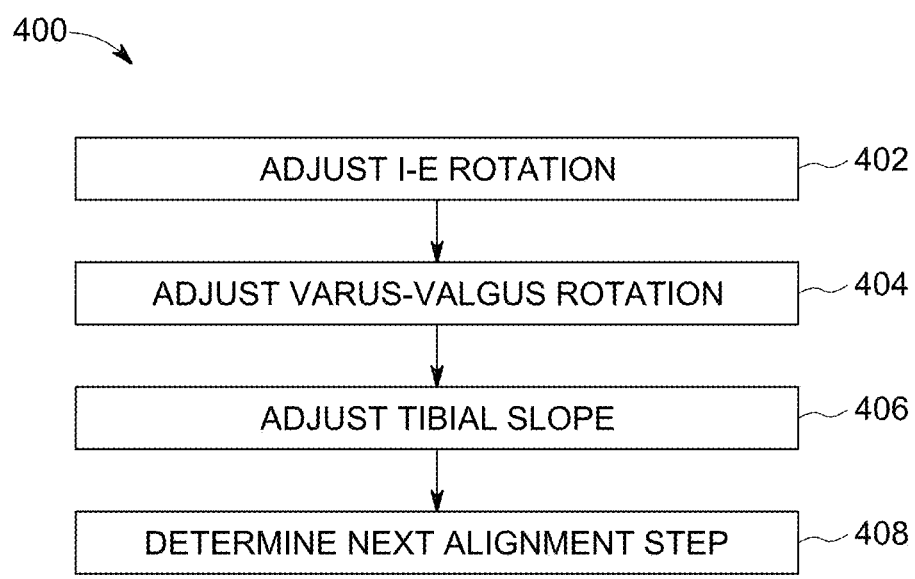
FIG. 6 is a flow chart illustrating a portion of the method of FIG. 4 for fine alignment, in accordance with an aspect of the present disclosure.

As shown in FIG. 6, the fine alignment procedure 400 may include, for example, further adjusting internal/external alignment 402, adjusting the varus/valgus rotation 404, adjusting the tibial slope 406, and determining the next alignment step 408. If the desired varus/valgus, internal/external rotation, and sagittal alignment are achieved with the joint line referencing alignment guide, a second pin may be inserted at the distal end of the alignment guide and into the tibial metaphysis. When the desired alignment is achieved with the joint line referencing alignment guide, the fast-track alignment guide 500 may be used next, as described in greater detail below. The fast-track alignment guide may be, for example, the type described in U.S. Provisional Application No. 62/899,703 filed Sep. 12, 2019 and entitled Joint Replacement Alignment Guides, Systems and Methods of Use and Assembly and International Application No. PCT/US2019/066408 filed Dec. 13, 2019 and entitled Joint Replacement Alignment Guides, Systems and Methods of Use and Assembly, which are hereby incorporated by reference in their entireties. However, when the desired alignment of the long axis of the tibia cannot be achieved with the joint line referencing alignment guide, or a second pin cannot be inserted into the distal end of the tibia then, the standard alignment guide 600 should be used, as described in greater detail below. The standard alignment guide may be, for example, the type described in U.S. Provisional Application No. 62/899,740 filed Sep. 12, 2019 and entitled Joint Replacement Alignment Guides, Systems and Methods of Use and Assembly, International Application No. PCT/US2019/066393 filed Dec. 13, 2019 and entitled Joint Replacement Alignment Guides, Systems and Methods of Use and Assembly, which is hereby incorporated by reference in its entirety. Once a determination is made on whether the fast-track alignment guide 500 or the standard alignment guide 600 guide will be used next, the pin sleeve(s) should be removed and then the joint line referencing guide may be removed from the patient's bones leaving the pin(s) in the tibia.

Figure 7:
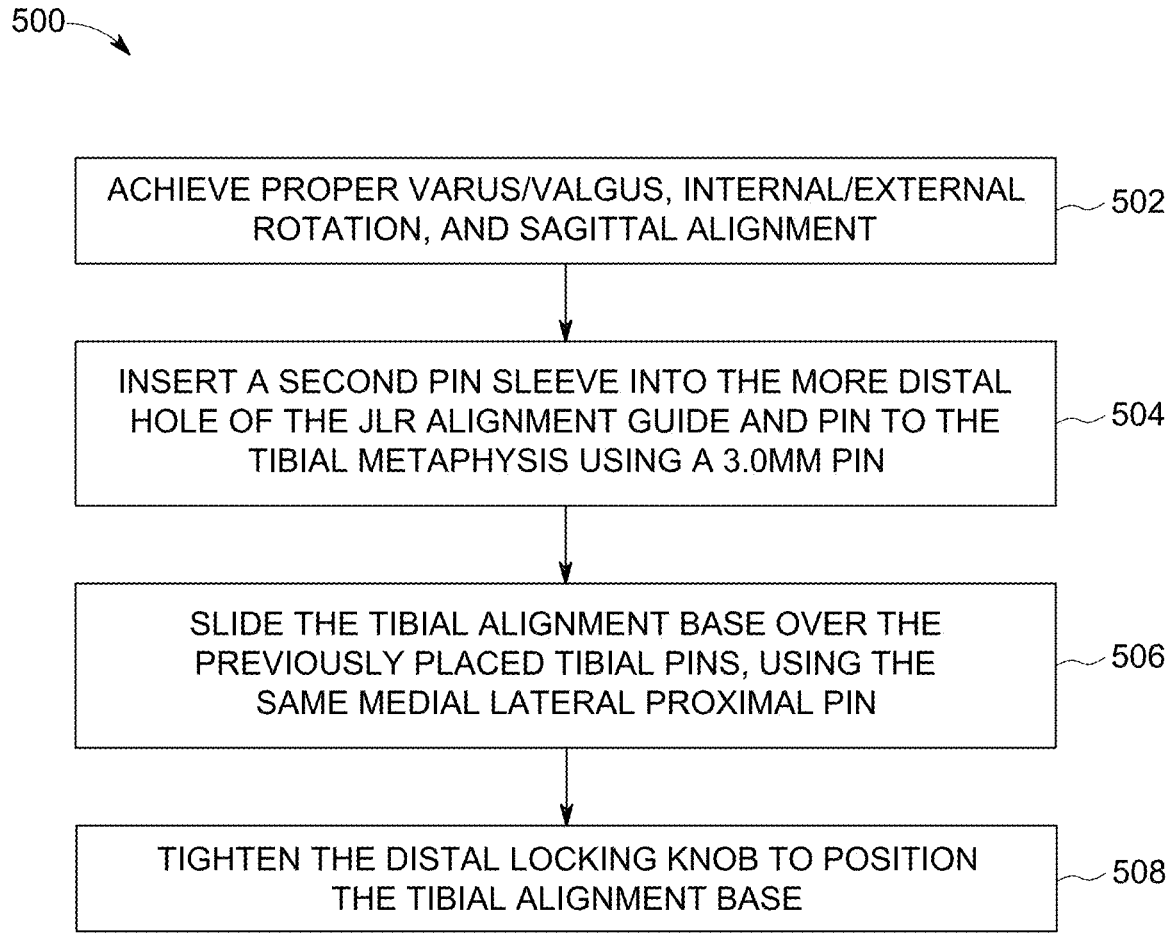
FIG. 7 is a flow chart illustrating a portion of the method of FIG. 1 for the fast-track alignment, in accordance with an aspect of the present disclosure.

As shown in FIG. 7, fast-track alignment is performed 500 when a proper varus/valgus, internal/external rotation, and sagittal alignment are achieved 502. For example, a second sleeve or pin sleeve may be inserted into a distal hole of the joint line referencing alignment guide and a second pin may be inserted through the sleeve and into the tibial metaphysis 504. When using the fast-track alignment guide, the fast-track alignment guide should be selected and the tibial alignment base should be slid over the pins and onto the tibia 506. Once the tibial base is positioned on the tibia, the distal locking knob may be tightened to secure the tibial base in position 508.

Figure 8:
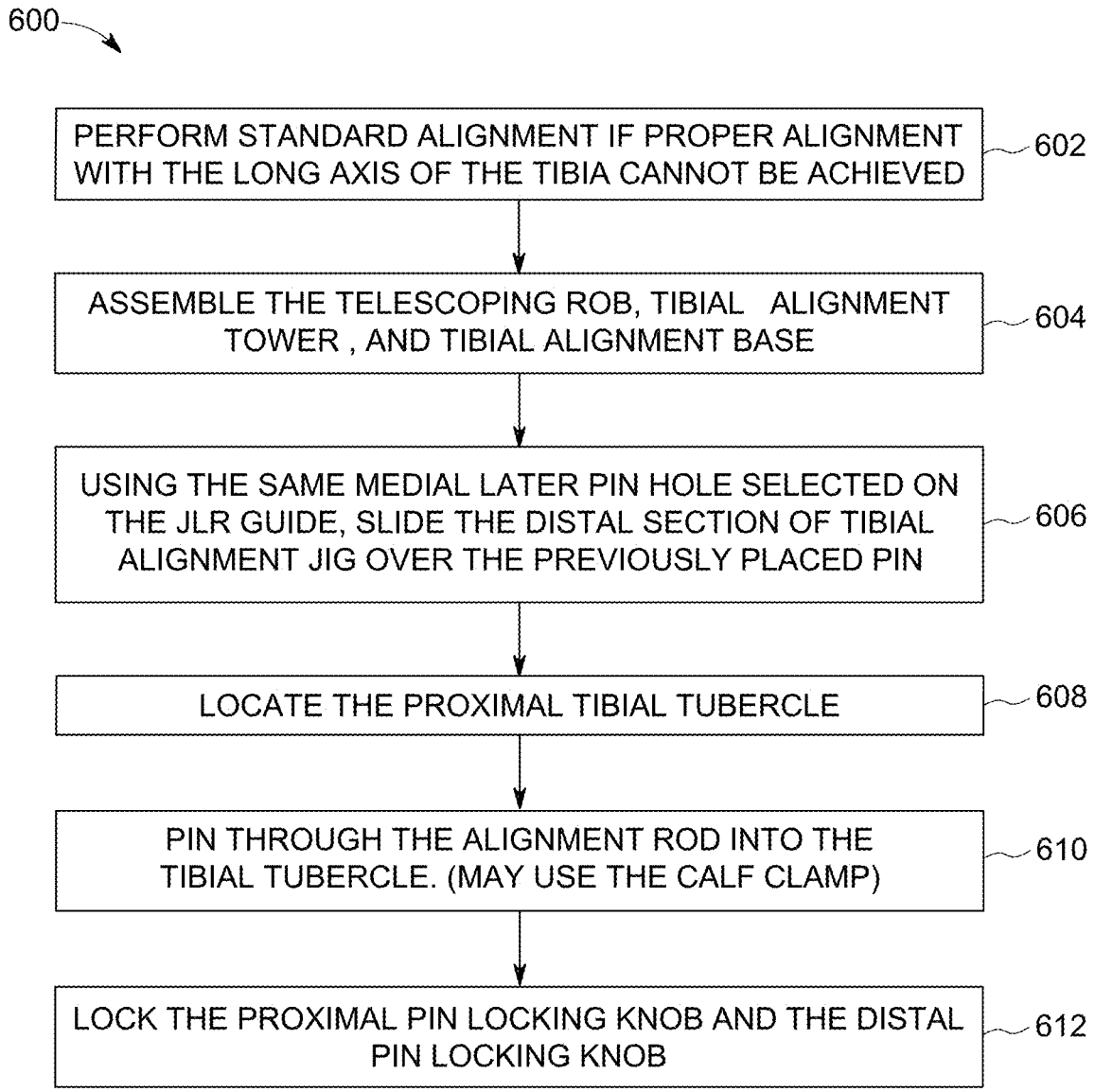
FIG. 8 is a flow chart illustrating a portion of the method of FIG. 1 for standard alignment, in accordance with an aspect of the present disclosure.

As shown in FIG. 8, standard alignment 600 is used when proper alignment with the long axis of the tibia cannot be achieved 602. When using a standard alignment guide 600, the standard alignment guide should be selected for the patient's anatomy. The standard alignment guide may also include a telescoping rod, tibial alignment tower, and tibial alignment base, which may be assembled together 604. Next, using the same medial later pin hole selected on the JLR guide, slide the distal section of the tibial alignment jig over the previously placed pin 606. The proximal tibial tubercle should be located 608 and a pin inserted through the telescoping rod and into the tibial tubercle 610. In addition, a clamp, such as a calf clamp, may be used. The calf clamp may be locked into position with respect to the telescoping rod using, for example, a knob, pin knob, or the like. Next, the tibial slope or sagittal alignment may be set by, for example, measuring a set distance, such as two finger widths, off the tibial crest. Once the desired sagittal alignment is achieved, the proximal pin locking knob and the distal pin locking knob may be tightened to lock the position of the proximal end of the standard alignment guide 612.

Figure 9:
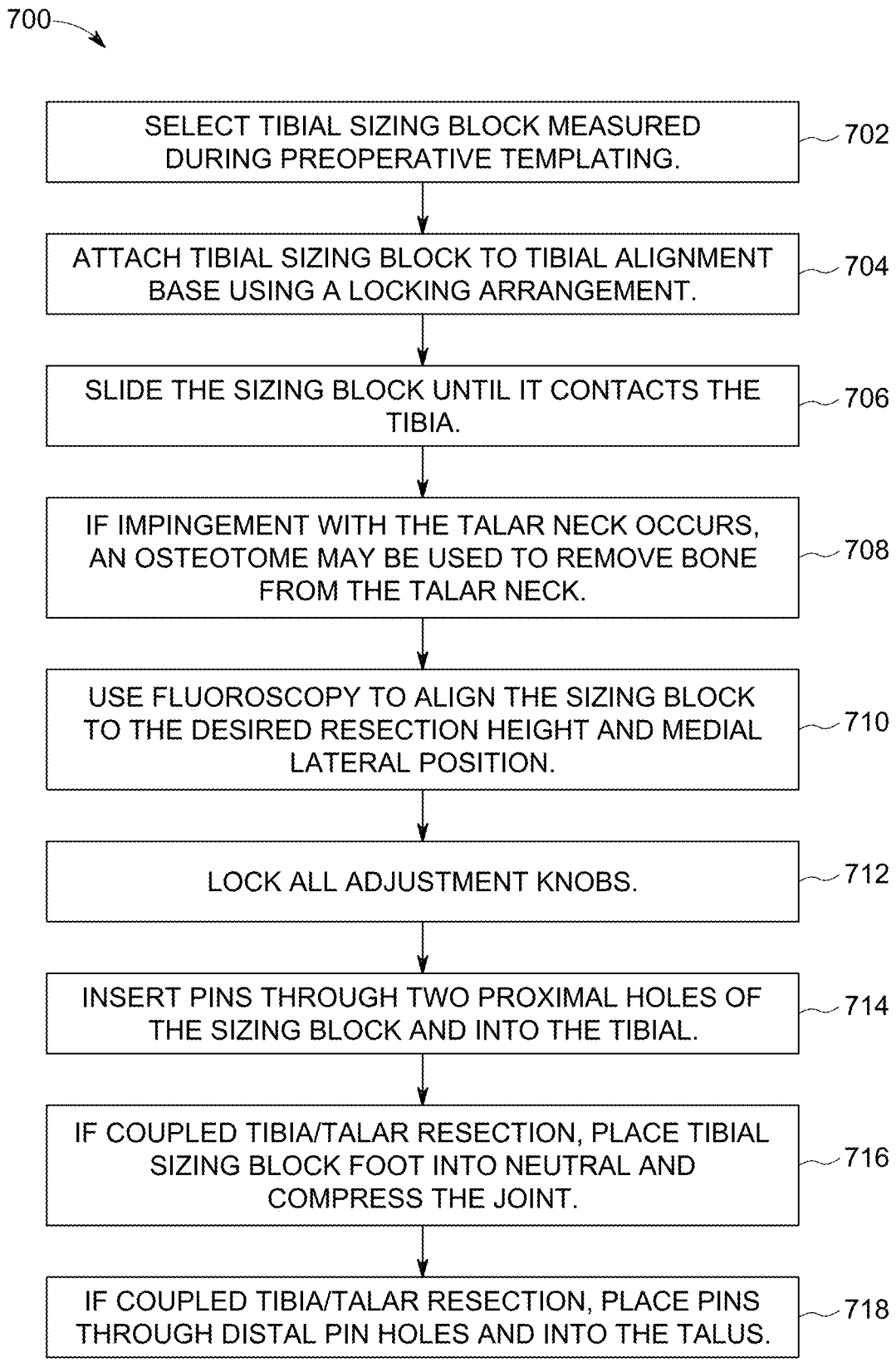
FIG. 9 is a flow chart illustrating a portion of the method of FIG. 1 for coupling the trial sizing block to the tibial alignment base.

As shown in FIG. 9, the tibial sizing block is coupled to the tibial alignment base 700. A tibial sizing block may be selected, for example, the sizing block may be selected based on measurements taken during preoperative templating 702. The sizing block may then be attached to the tibial alignment base, for example, using a dovetail arrangement or other locking arrangement 704. The sizing block may be, for example, slid posteriorly until the sizing block contacts the tibia 706. If necessary due to impingement with the talar neck, an osteotome may be used to remove bone from the talar neck 708. After the sizing block is in a desired position on the tibia, the sizing block may be locked into place, for example, using a hex driver and a hex opening. The sizing block may be, for example, of the type described in U.S. Provisional Application No. 62/898,615 entitled Resection Guides, Sweeping Reamers, and Methods for Use in Total Ankle Replacement, which is hereby incorporated by reference in its entirety.

After attachment of the sizing block, the tibial alignment jig may be aligned to the long axis of the tibia using the varus-valgus adjustment knobs positioned near the proximal pin. Once the desired varus-valgus position is achieved, the varus-valgus adjustment knobs may be locked with the locking screw by, for example, an instrument, such as a driver or hex driver. In addition, the telescoping rod lock knob positioned near the center of the tibial alignment jig may be turned to lock the length of the standard alignment guide. Finally, the internal/external rotation of the sizing block may be set using the internal/external adjustment screw.

The sizing block may be further aligned using fluoroscopy to set the sizing block to the desired resection height and medial lateral position 710. Once the desired resection height and medial lateral positions are set, all the adjustment knobs may be locked 712 and pins may be inserted through two proximal holes of the sizing block and into the tibia 714. For coupled tibial/talar resections, the foot should be placed into neutral and the joint compressed 716. Then, pins may be placed, for example, through the distal pin holes and into the talus 718. The talus pins may be, for example, shorter in length than the tibial pins. However, if performing a decoupled resection pins should not be placed into the talus.

Figure 10:
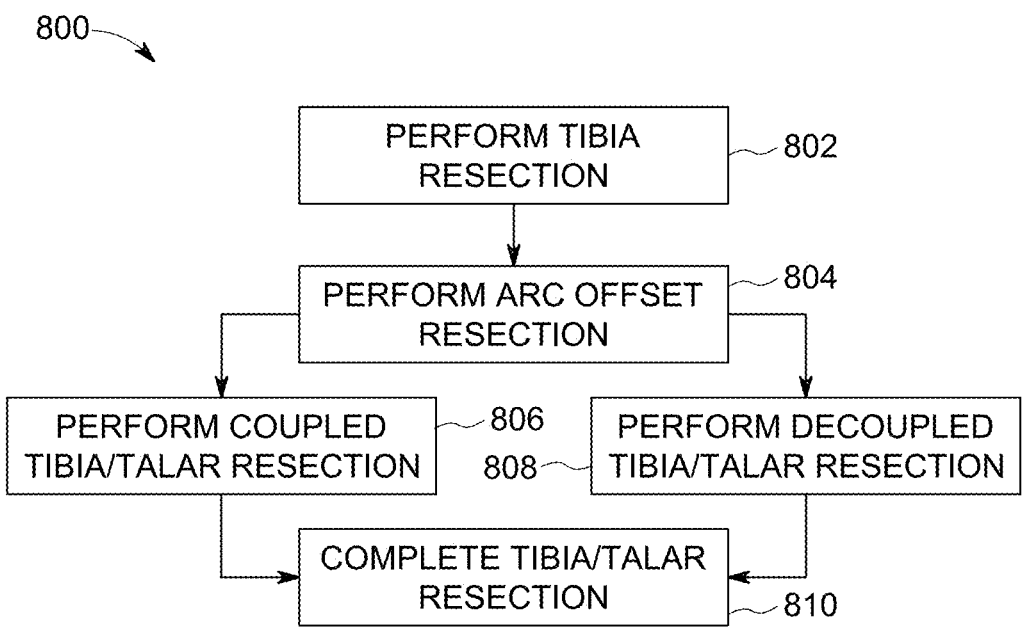
FIG. 10 is a flow chart illustrating a portion of the method of FIG. 1 for performing tibial and talar resections, in accordance with an aspect of the present disclosure.

As shown in FIG. 10, the tibia and talar resections procedures 800 may include, for example, a tibia resection 802, an arc offset resection 804, either a coupled tibia/talar resection 806 or a decoupled tibia/talar resection 808, and a completion of the tibia/talar resection 810.

Figure 11:
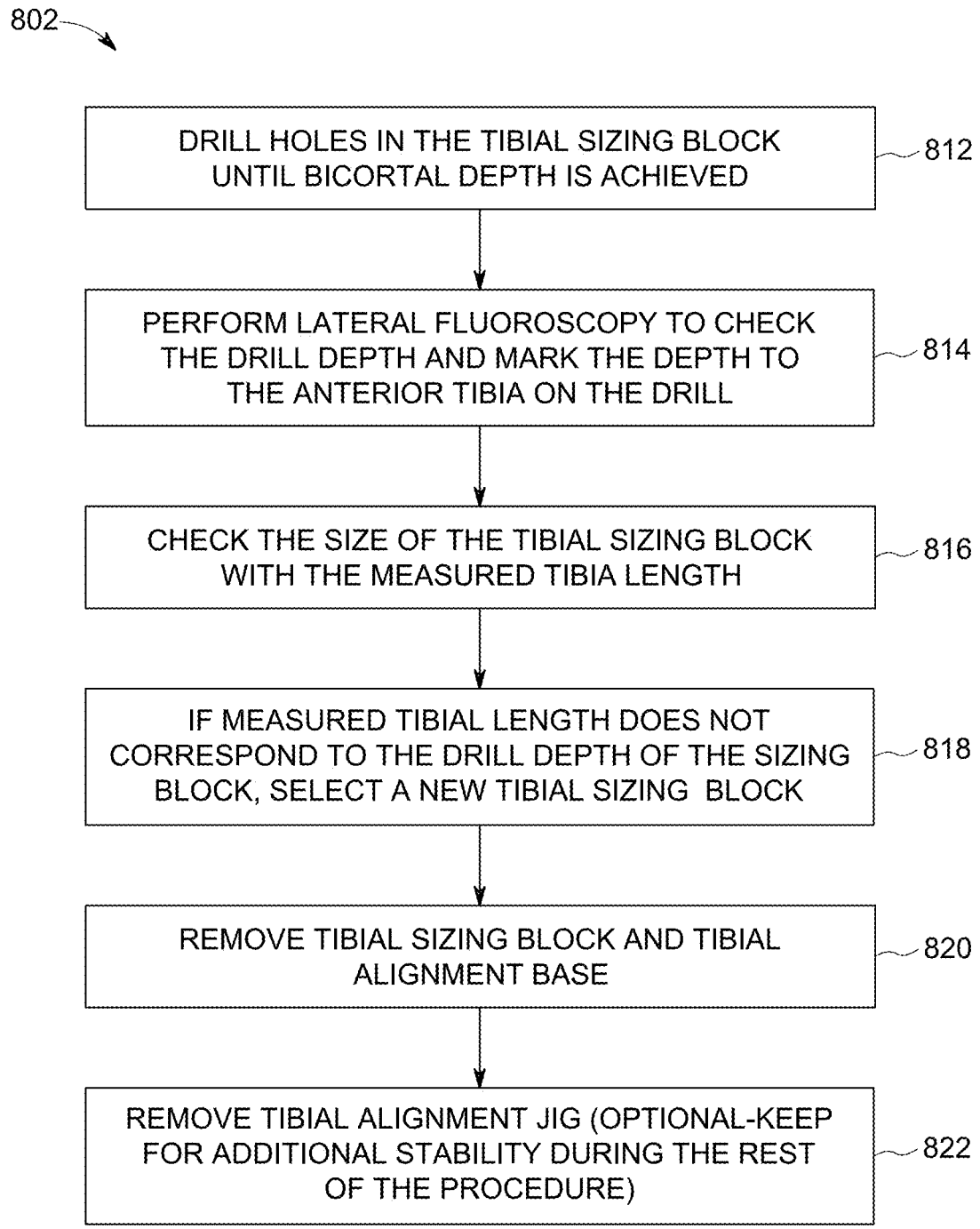
FIG. 11 is a flow chart illustrating a portion of the method of FIG. 10 for performing a tibia resection, in accordance with an aspect of the present disclosure.

As shown in FIG. 11, the tibia resection 802 procedure may include, for example, drilling holes in the tibia sizing block until a bicortal depth is achieved 812. Next, lateral fluoroscopy may be performed to check the drill depth 814 and the size of the tibial sizing block may be compared with the measured tibia length 816. Then, a new tibial sizing block may be selected and inserted onto the alignment guide 818, if needed. If the tibial sizing block is of a different size compared to the measured tibia length, the tibial sizing block and tibial alignment base 820 may be removed or exchanged. After drilling the openings in the tibial drill openings, the tibial alignment jig may be removed 822. After the sizing block is placed in the desired position, an instrument, for example, a drill or resection drill may be inserted through one of the center holes in the sizing block until bicortal depth is achieved. The center hole of the sizing block may be, for example, marked for later reference. Next, perform lateral fluoroscopy to check the drill depth and mark the depth to the anterior tibia on the drill. A sizing chart may optionally be used to check the size of the sizing block with the measured tibial length. To check the size of the sizing block, the drill depth may be compared to the measured tibial length. If the measured tibial length does not correspond to the drill depth of the sizing block being used, then a new sizing block that more closely corresponds to the measured tibial length should be selected. Once the desired sizing block is selected and coupled to the tibial alignment base, the remaining drill holes should be drilled until all holes have been drilled. While drilling the tibia using the remaining drill holes, proper depth control and a "pecking technique," or alternative method of drilling through bone, should be used. In addition, care should be taken not to perforate the neurovascular bundle medially while drilling the remaining drill holes. After all of the drill holes are drilled, the sizing block locking screws should be loosened and the sizing block removed from the tibial alignment base. The tibial alignment jig may also be optionally removed after the sizing block is drilled or may be left in place for additional stability during the rest of the procedure.

Figure 12:
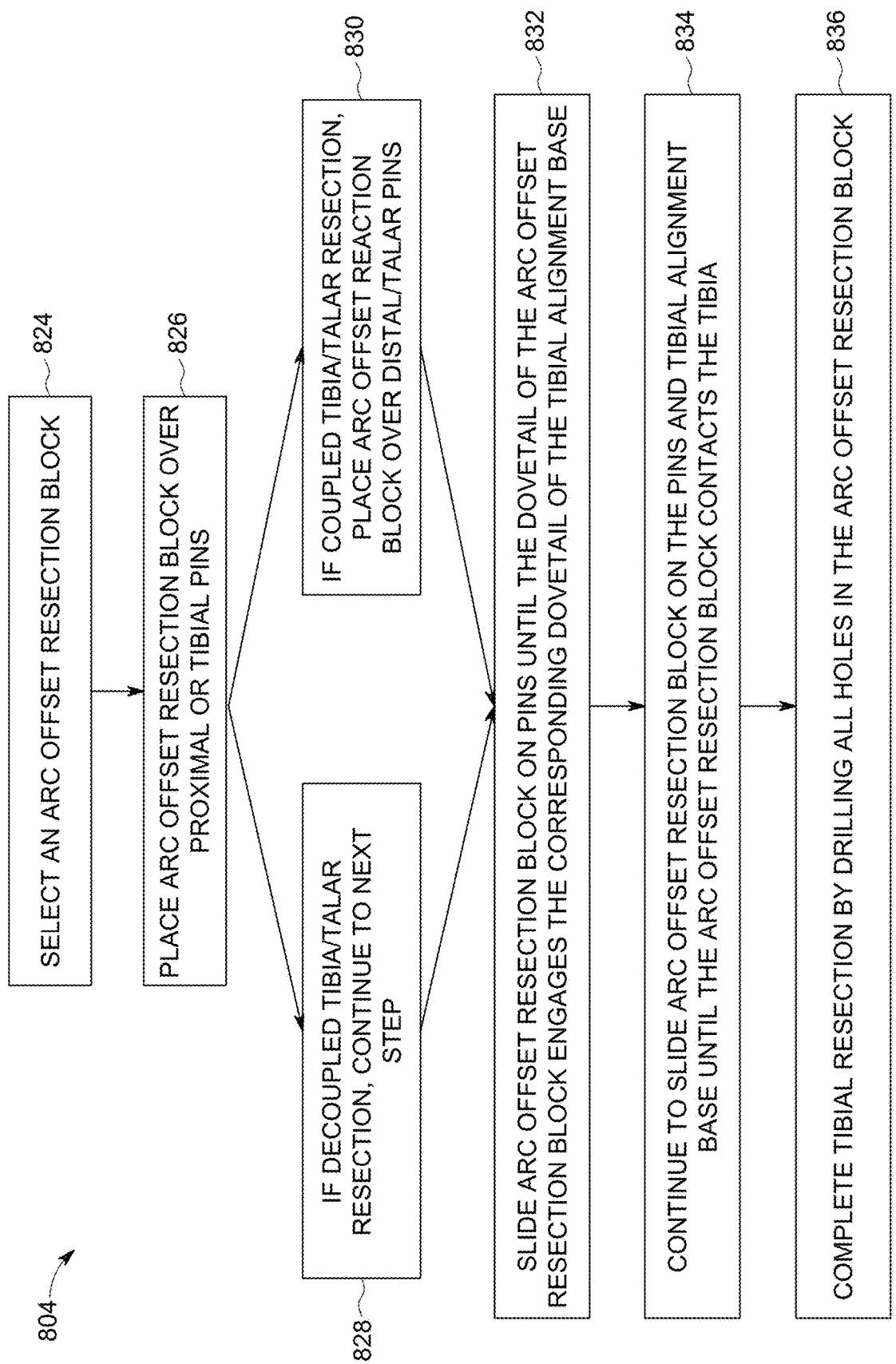
FIG. 12 is a flow chart illustrating a portion of the method of FIG. 10 for performing the arc offset resection, in accordance with an aspect of the present disclosure.

As shown in FIG. 12, the arc offset resection procedure 804 may be performed and include, for example, selecting an arc offset resection block 824 and placing the arc offset resection block over the proximal tibial pins 826. The method may also include a tibia/talar resection procedure that may include offsetting the resection block over the distal/talar pins 828, sliding the arc offset resection block on pins until the dovetail of the arc offset resection block engages the corresponding dovetail of the tibial alignment base 830, Continue to slide the arc offset resection block on the pins and tibial alignment base until the arc offset resection block contacts the tibia 832, and completing the tibial resection by drilling all holes in the arc offset resection block 834.

An arc offset resection block may be selected that corresponds to the size of the removed sizing block. The selected arc offset block may then be placed over the proximal or tibial pins. If performing a coupled resection, the selected arc offset block may also be placed over the distal or talar pins. The arc offset block may then be slid on the pins until the dovetail of the arc offset block engages the corresponding dovetail of the tibial alignment base. The arc offset block may continue to be slid on the pins and tibial alignment base until the arc offset block contacts the tibia. Once the arc offset block is positioned on the tibia, the drill or resection drill may be used to drill all of the holes in the arc offset block to complete the tibial resection.

Figure 13:
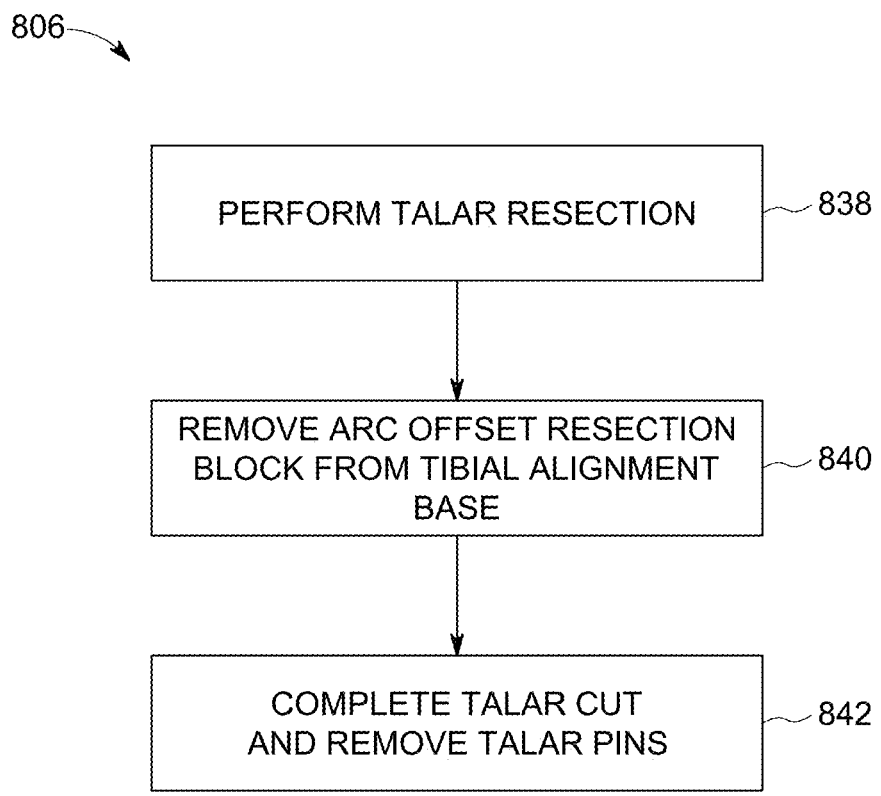
FIG. 13 is a flow chart illustrating a portion of the method of FIG. 10 for performing the tibia/talar resection, in accordance with an aspect of the present disclosure.

As shown in FIG. 13, a coupled tibia/talar resection procedure 806 may include, for example, a talar resection 838, removing the arc offset resection block from tibial alignment base 840, and completing the talar cut and removing the talar pins 842. After the tibial resection is performed, then the talar resection may be performed. For a coupled talar resection, pins may optionally be placed in the medial and lateral ends of the talar resection slot of the arc offset block. The pins in the medial and lateral ends of the talar resection slot may, for example, help to prevent notching of the medial malleolus and fibula. A cutting instrument, for example, a saw blade may then be inserted into the talar resection slot to make the talar resection. After the talar resection is made the arc offset block may be removed from the tibial alignment base. Then, if necessary, the talar cut may be completed and the talar pins removed. The tibial pins should remain in place after removal of the talar pins.

Figure 14:
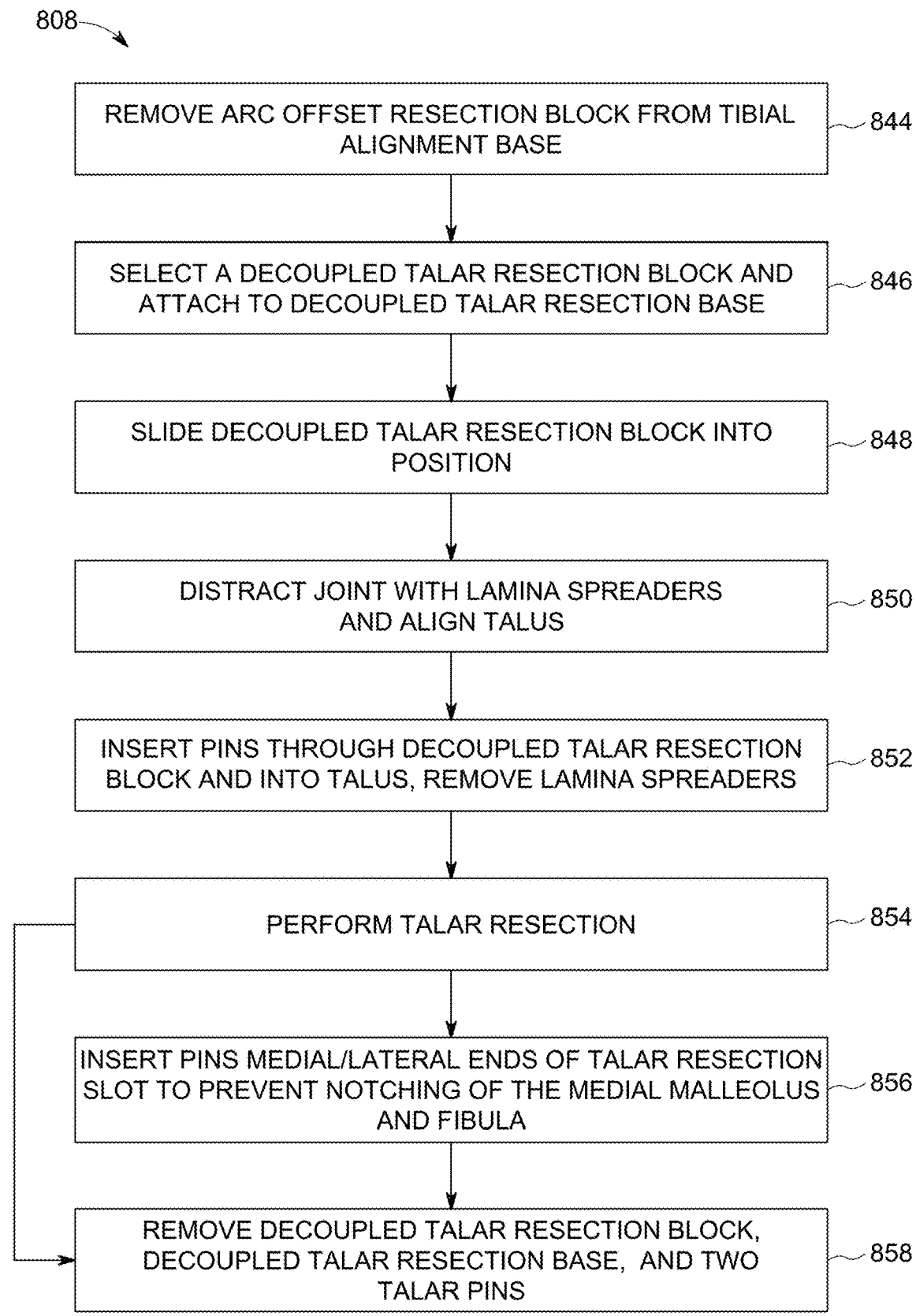
FIG. 14 is a flow chart illustrating a portion of the method of FIG. 10 for decoupling the tibia/talar resection instrument during the portion of the method for the tibia and talar resections, in accordance with an aspect of the present disclosure.

As shown in FIG. 14, a decoupled tibia/talar resection procedure 808 may include, for example, removing the arc offset resection block from tibial alignment base 844. The procedure may also include selecting a decoupled talar resection block and attaching the decoupled talar resection base 846. Next, the decoupled talar resection block, for example, may be a resection block, and the method may include sliding the decoupled talar resection block into position 848. Then, the method may include distracting the joint with lamina spreaders and aligning the talus 850 and inserting pins through decoupled talar resection block and into talus. Then, the lamina spreaders 852 may be removed and a talar resection performed 854. Optionally, the method may include inserting pins in medial/lateral ends of talar resection slot to prevent notching of the medial malleolus and fibula 856. Next, the method may include removing the decoupled talar resection block, decoupled talar resection base, and two talar pins 858.

Alternatively, for a decoupled talar resection after removal of the arc offset block, a decoupled talar resection block may be selected. If necessary for placement of the decoupled resection block, some of the resected tibial bone may be removed. The selected decoupled talar resection block may then be assembled by attaching the decoupled talar resection base to the decoupled talar resection block. The assembled resection block and base may then be slid over the tibial pins until the tongue of the talar resection block is positioned on the surface of the talus. The ends of each lamina spreader may then be inserted into the cutouts of the decoupled talar resection base and tension applied to distract the joint. After the talus is aligned to the proper position, two pins may be inserted through the decoupled talar resection block and into the talus. After the pins are inserted, the lamina spreaders may be removed and a talar resection may be made using a saw blade. Optionally, pins may also be placed in the medial and lateral ends of the talar resection slot to prevent notching of the medial malleolus and fibula. Next, the decoupled talar resection base and the resection block may be removed. In addition, the two talar pins may be removed and the tibial pins may be kept in place.

Figure 15:
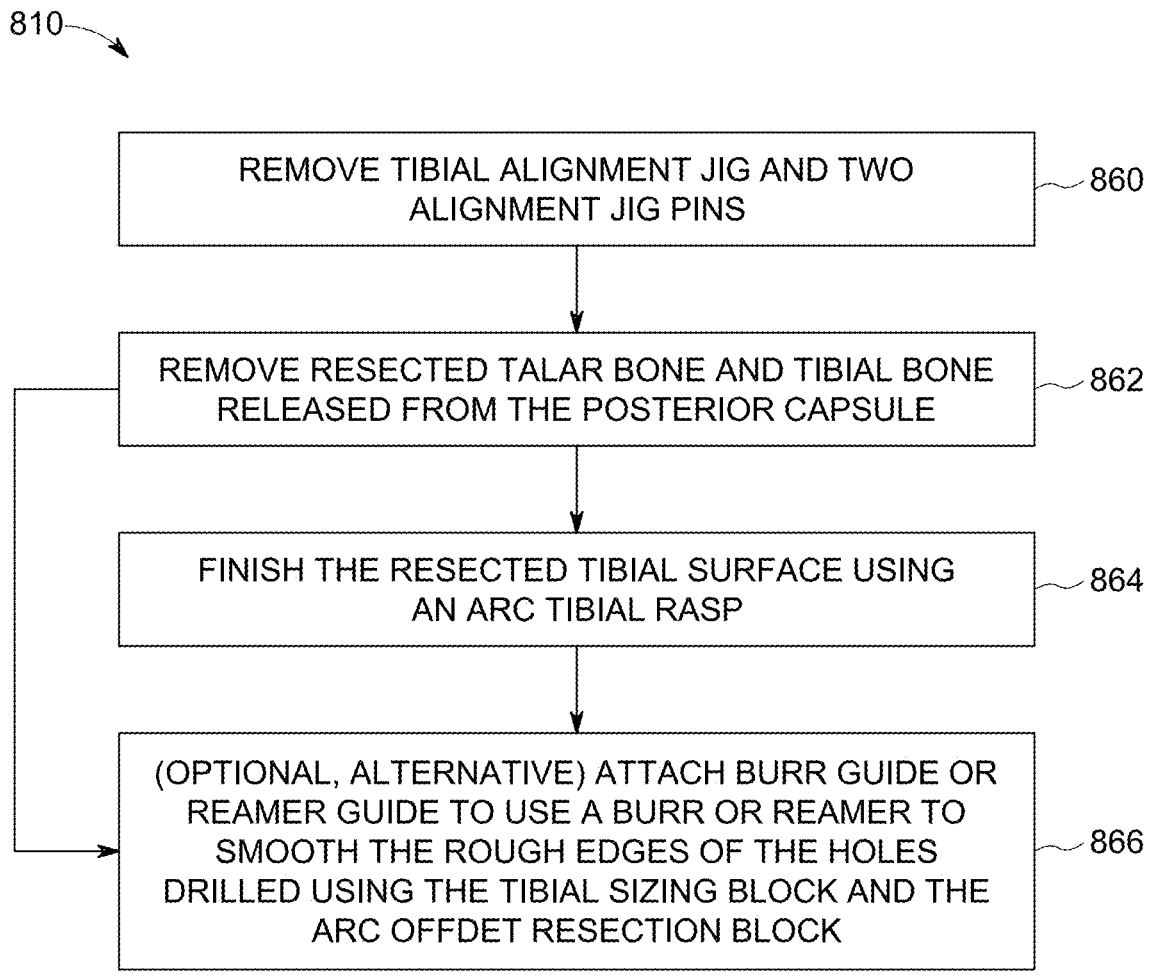
FIG. 15 is a flow chart illustrating a portion of the method of FIG. 1 for completing the tibia/talar resection, in accordance with an aspect of the present disclosure.

As shown in FIG. 15, the tibial and talar resections may then be completed 810 by removing the tibial alignment jig and the two alignment jig pins 860 inserted into the tibia. Next, the resected talar bone may be removed and the tibial bone released from the posterior capsule 862. The resected tibial bone may be split by, for example, using a small osteotome or a reciprocating saw blade. Then, the tibial bone may be removed. The resected tibial bone may be removed using, for example, an arc osteotome and a mallet or a reciprocating saw. If necessary, an arc tibial rasp may be used to finish the resected tibial surface 864. Alternatively, a burr guide or reamer guide may then optionally be coupled to the tibial alignment base 866. The burr guide allows for a burr or reamer to be inserted through a slot in the burr guide to smooth the rough edges of the holes drilled using the tibial sizing block and the arc offset block.

Figure 16:
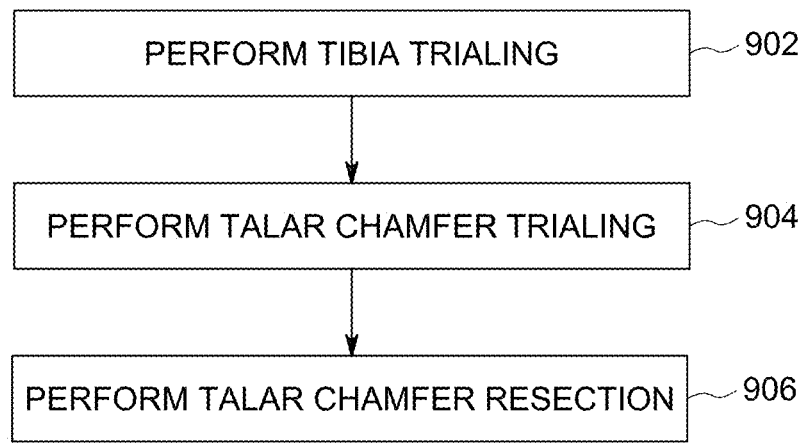
FIG. 16 is a flow chart illustrating a portion of the method of FIG. 1 for performing the trial and talar chamfer resection, in accordance with an aspect of the present disclosure.

As shown in FIG. 16, once the tibial and talar resections 800 are completed, a trialing and the talar chamfer resection 900 procedure may be performed. The trial and talar chamfer resection may include, for example, performing tibia trialing 902, performing talar chamfer trialing 904, and performing the talar chamfer resection 906, as described in greater detail below.

Figure 17:
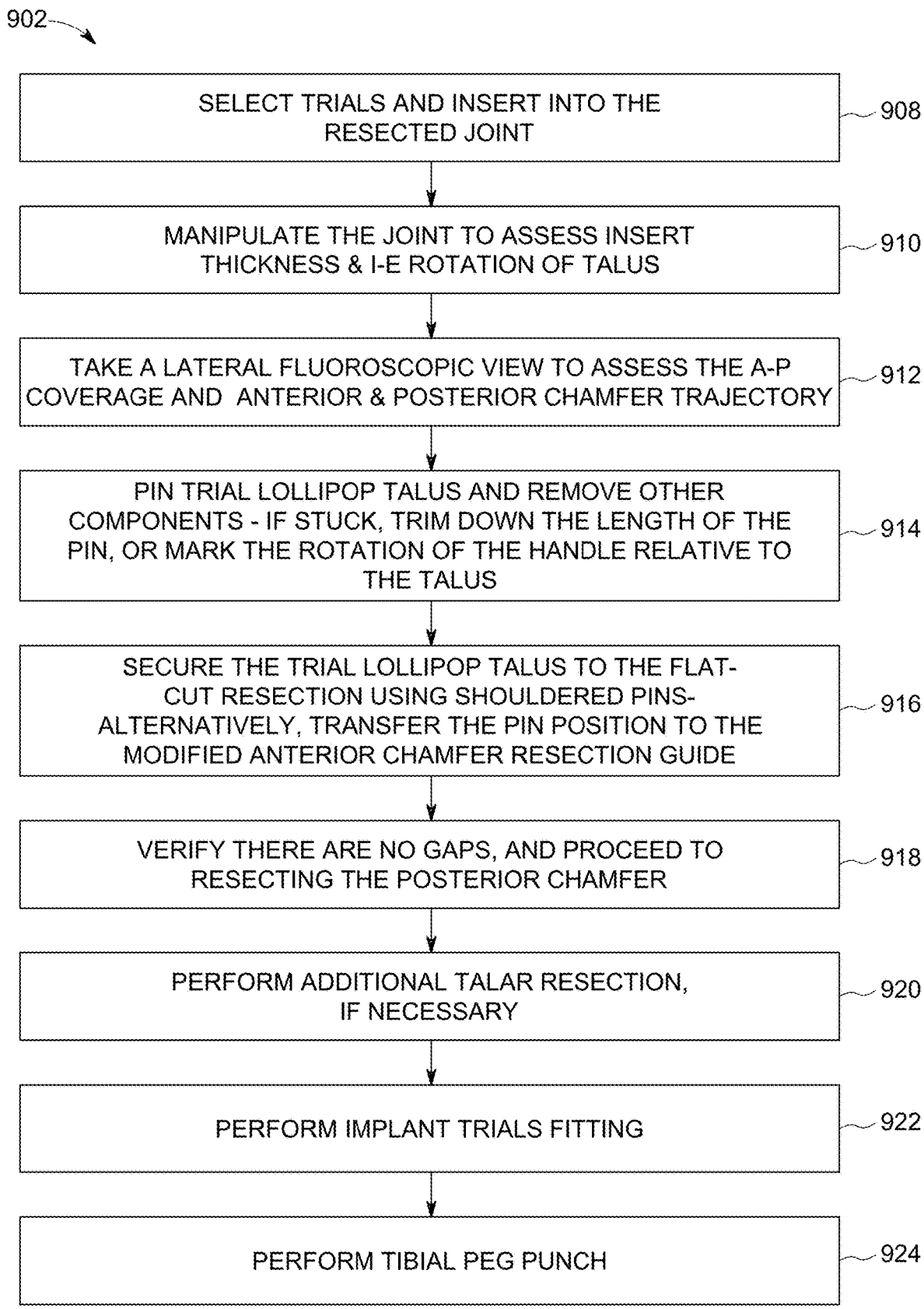
FIG. 17 is a flow chart illustrating a portion of the method of FIG. 16 for performing tibial trialing of FIG. 16, in accordance with an aspect of the present disclosure.

As shown in FIG. 17, the tibial trialing method 902 may include, for example, selecting the trials and inserting the trials into the joint 908 and manipulating the joint to assess thickness 910. The method may also include obtaining a fluoroscopic view to assess the anterior and posterior chamfer trajectory 912 and pinning the trial lollipop talus and removing other components 914. The tibial trialing method 902 may further include securing the trial lollipop to the resection surface 916, verifying there are no gaps and proceeding with the chamfer resection 918. If necessary, the method may also include performing additional resection of the tibia 920. In addition, the method includes performing implant trial fittings 922 and performing the tibial peg punch 924.

The method further includes, selecting the appropriate size resection gap trials and inserts 908 to check that the minimum thickness has been resected that is needed for the implant 910. In addition, the resection gap trials may be used to check that the tibial resection geometry is appropriate. A lateral fluoroscopic view may then be taken to assess the anterior-posterior coverage and anterior and posterior chamfer trajectory 912. The trial lollipop talus may be pinned and other components may be removed. If any of the components are stuck, the length of the pin may be trimmed down or the rotation of the handle may be marked relative to the talus 914. Next, the trial lollipop talus may be secured to the flat-cut resection using shouldered pins. Alternatively, the pin position may be transferred to the modified anterior chamfer resection guide 916. Next, the method may include verifying that there are no gaps and proceeding to resect the posterior chamfer 918.

Figure 18:
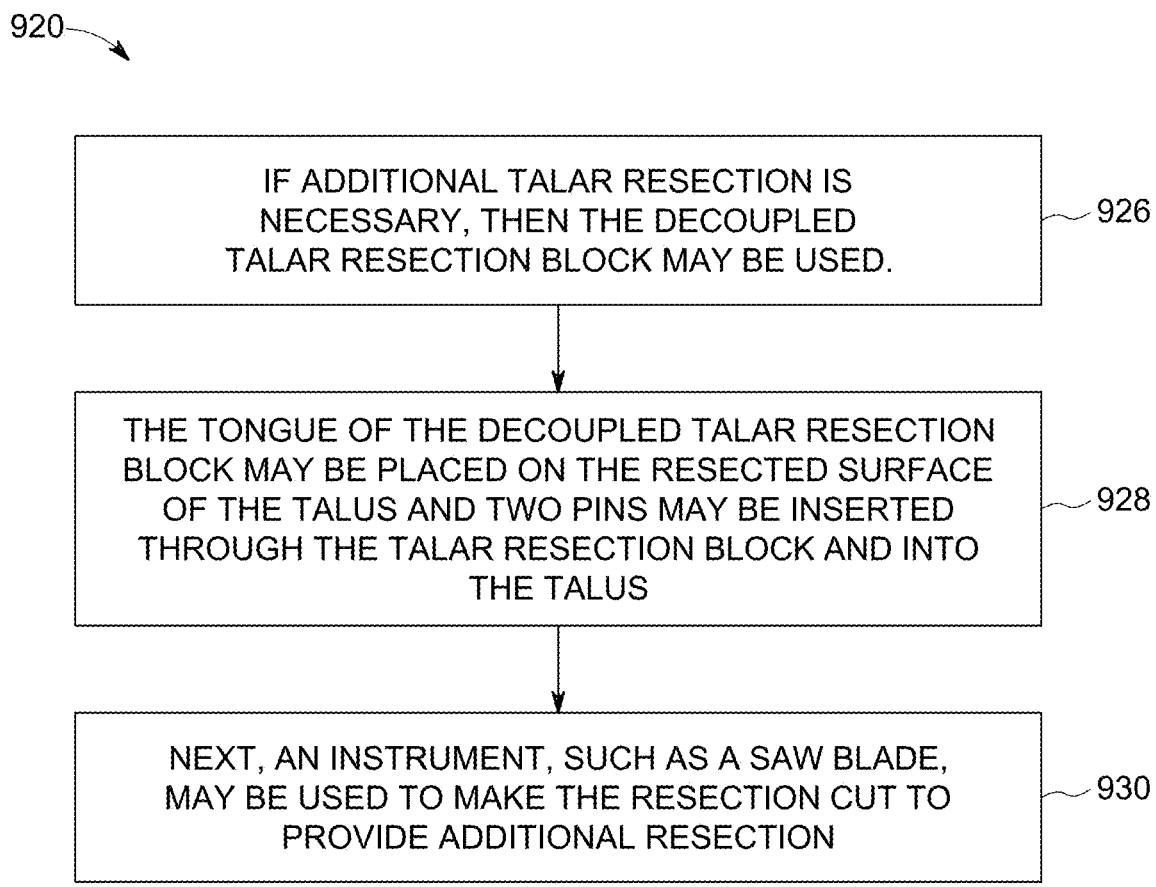
FIG. 18 is a flow chart illustrating a portion of the method of FIG. 17 for performing additional talar resections, in accordance with an aspect of the present disclosure.

As shown in FIG. 18, if additional talar resection is necessary 920, then the decoupled talar resection block may be used 926. The tongue of the decoupled talar resection block may be placed on the resected surface of the talus and two pins may be inserted through the talar resection block and into the talus 928. Next, an instrument, such as a saw blade, may be used to make the resection cut to provide additional resection 930. The additional resection using the talar resection block may be, for example, an additional 1 mm to 3 mm of resection and more preferably 2 mm of resection.

Figure 19:
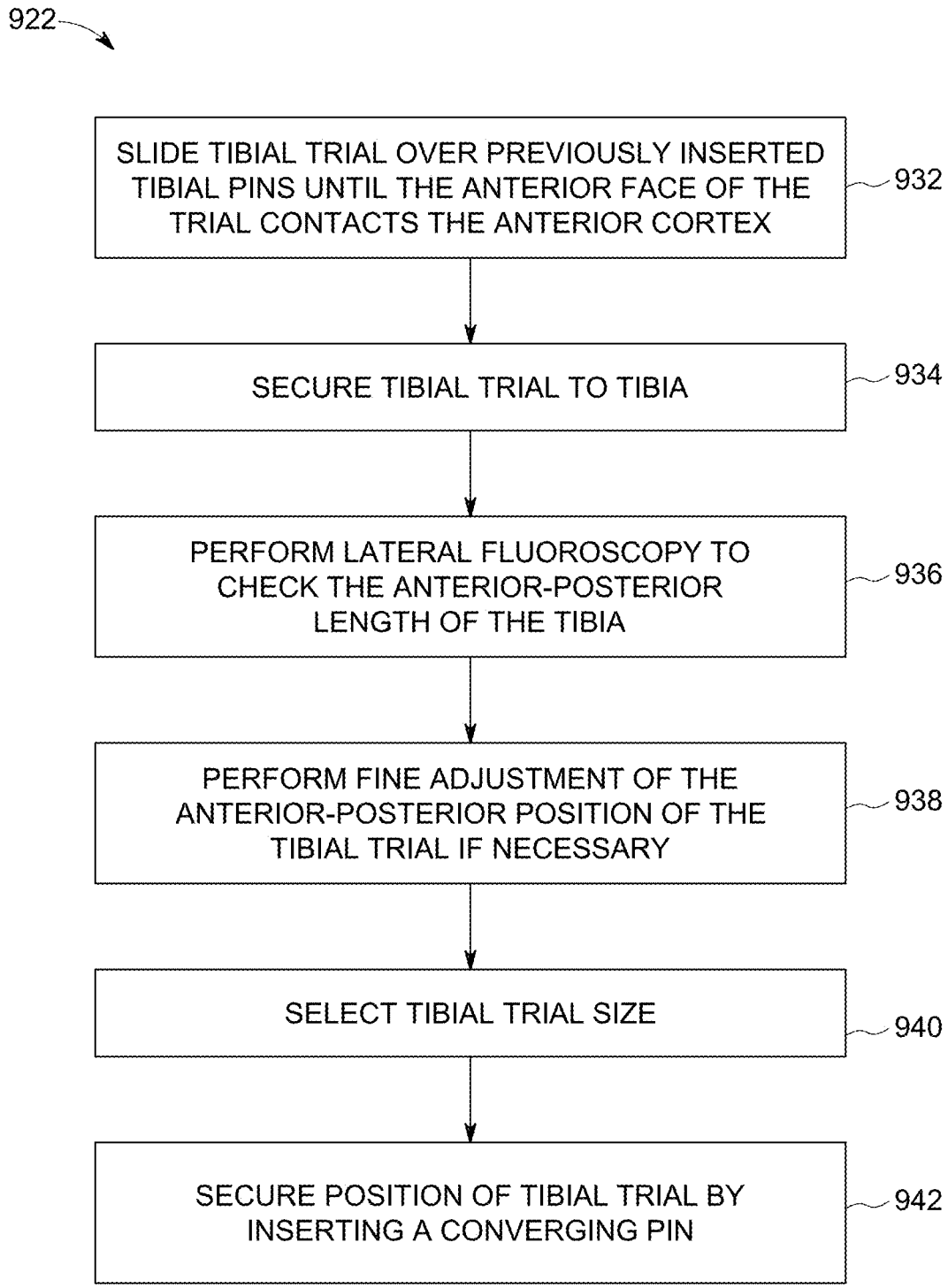
FIG. 19 is a flow chart illustrating a portion of the method of FIG. 17 for performing the implant trial fitting, in accordance with an aspect of the present disclosure.

As shown in FIG. 19, the method of fitting the implant trials 922 may include, for example, sliding the tibial trial over the previously inserted tibial pins until the anterior face of the trial contacts the anterior cortex 932. The method may also include securing the tibial trial to the tibia 934 and performing lateral fluoroscopy to check the anterior-posterior length of the tibia 936. In addition, the method includes performing fine adjustment of the anterior-posterior position of the tibial trial 938, if necessary, selecting the tibia trial size 940, and securing the position of tibial trial by inserting a converging pin 942. After the trials have been selected and fit into the resected joint, the implant trials may be fit into the joint. For example, the desired sized tibial trial may be slid over the previously inserted tibial pins and slid posteriorly until the anterior face of the trial contacts the anterior cortex. Once inserted, a lamina spreader may be used to securely hold the tibial trial to the tibia. Then, lateral fluoroscopy may be performed to check the anterior-posterior length of the tibia. The posterior notch represents a standard length tibia, while the full length of the tibial trial represents a long length tibia. If necessary, fine adjustment of the anterior-posterior position of the tibial trial may be performed using a screw on the anterior face of the trial to adjust the offset of the tibial trial. Once the desired size and position of the tibial trial are selected a converging pin may be inserted to secure the position of the tibial trial.

Figure 20:
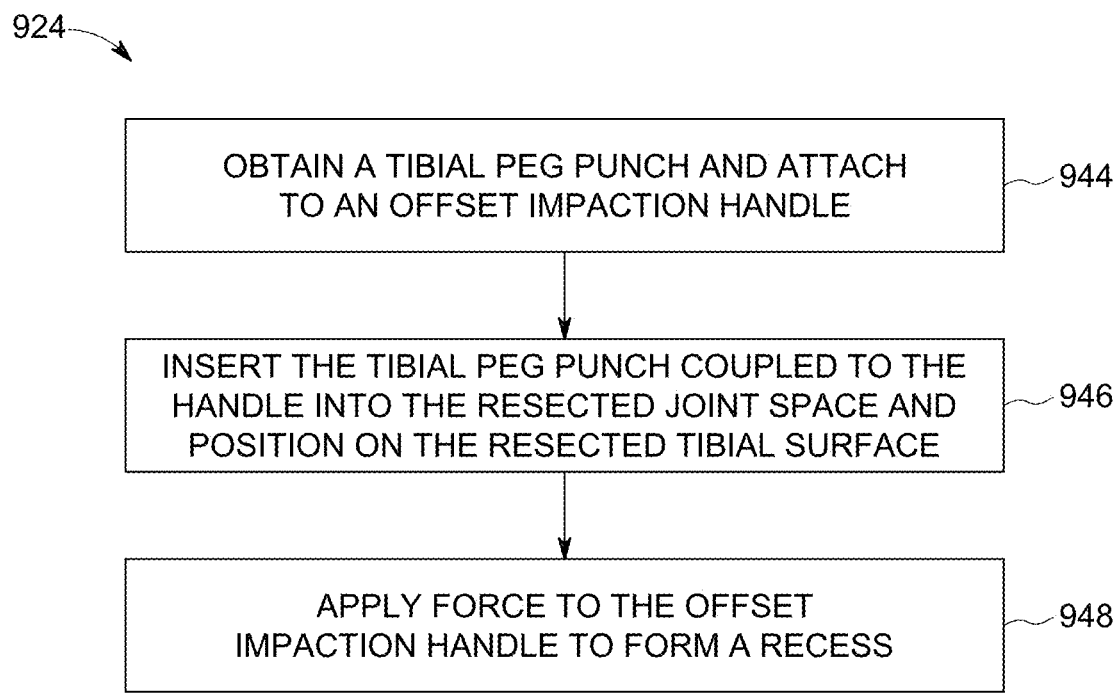
FIG. 20 is a flow chart illustrating a portion of the method of FIG. 17 for performing the tibial peg punch, in accordance with an aspect of the present disclosure.

As shown in FIG. 20, a tibial peg punch 924 process may be performed. After the size and position of the tibial implant are set, the tibial peg punch may be used to form the recesses for receiving the pegs on the tibial implant 924. The tibial peg punch may be performed by obtaining the desired tibial peg punch and attaching it to the offset impaction handle 944. The tibial peg punch coupled to the handle may then be inserted into the resected joint space and the tibial peg punch may be positioned on the resected tibial surface 946. Once positioned, the tibial pegs may be punched or recesses formed by applying force to the offset impaction handle 948. If necessary, a lamina spreader may be used to facilitate access to punch the posterior pegs. The tibial peg punch may be, for example, a left offset punch for right handed users or a right offset punch for left handed users. The tibial peg punch, offset impaction handle and lamina spreader may be of the type described in U.S. Provisional Application No. 62/898,854, entitled Distractors having Attachable Paddles, Impaction Devices, and Methods for Use in Total Ankle Replacement which is hereby incorporated by reference in its entirety.

Figure 21:
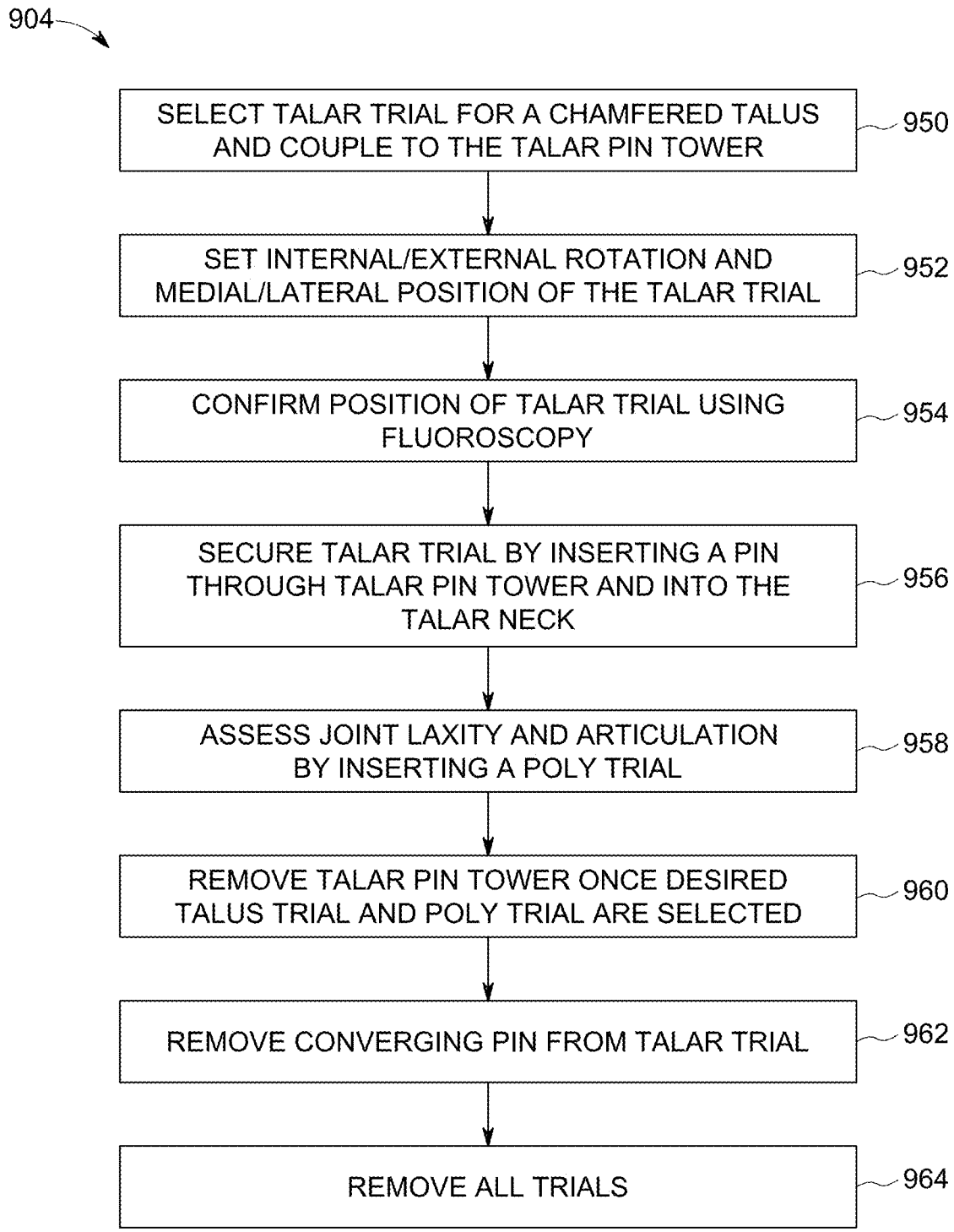
FIG. 21 is a flow chart illustrating a portion of the method of FIG. 16 for performing the talar chamfer trialing, in accordance with an aspect of the present disclosure.

As shown in FIG. 21, a talar chamfer trialing process 904 may include, for example, selecting a talar trial for a chamfered talus and coupling the talar trial to the talar pin tower 950. The talar chamfer trialing method may also include setting the internal/external rotation and medial/lateral position of the talar trial 952 and confirming the position of talar trial using fluoroscopy 954. In addition, the method may include securing the talar trial by inserting a pin through a talar pin tower and into the talar neck 956 and assessing the joint laxity and articulation by inserting a poly trial 958. Once the desired talus trial and poly trial are selected the talar pin tower may be removed 960, the converging pin may also be removed from talar trial 962, and all the trials may be removed 964.

More specifically, the talar chamfer trialing process 904 may include using the talar trials to select the desired size talar implant and determine the appropriate position of the talar implant. For a chamfered talus, the desired size talar trial may be selected and coupled to the talar pin tower. The internal/external rotation and medial/lateral position of the talar trial may be set and the position of the talar trial may be checked with fluoroscopy. The center notch may designate, for example, the center of the implant and may be used to align the implant lateral process. The anterior slot of the talar trial may represent, for example, the projected path of the talar anterior chamfer and the posterior slot may represent, for example, the posterior chamfer. After the desired position is confirmed using fluoroscopy, a pin may be inserted through the talar pin tower and into the talar neck to secure the talar trial in the desired positon. Next, a poly trial, for example, the thinnest poly trial may be inserted and the joint laxity and articulation may be assessed. If necessary, the first poly trial may be removed using a poly removal tool to disengage the poly trial from the tibial trial and additional poly trials, for example, thicker poly trials may be inserted until the desired joint laxity and articulation are achieved. After the desired talus trial and poly trial are selected, the talar pin tower may be removed by, for example, unthreading the tower from the talar trial. The converging pin may then be removed from the talar trial. Finally, all trials may be removed.

Figure 22:
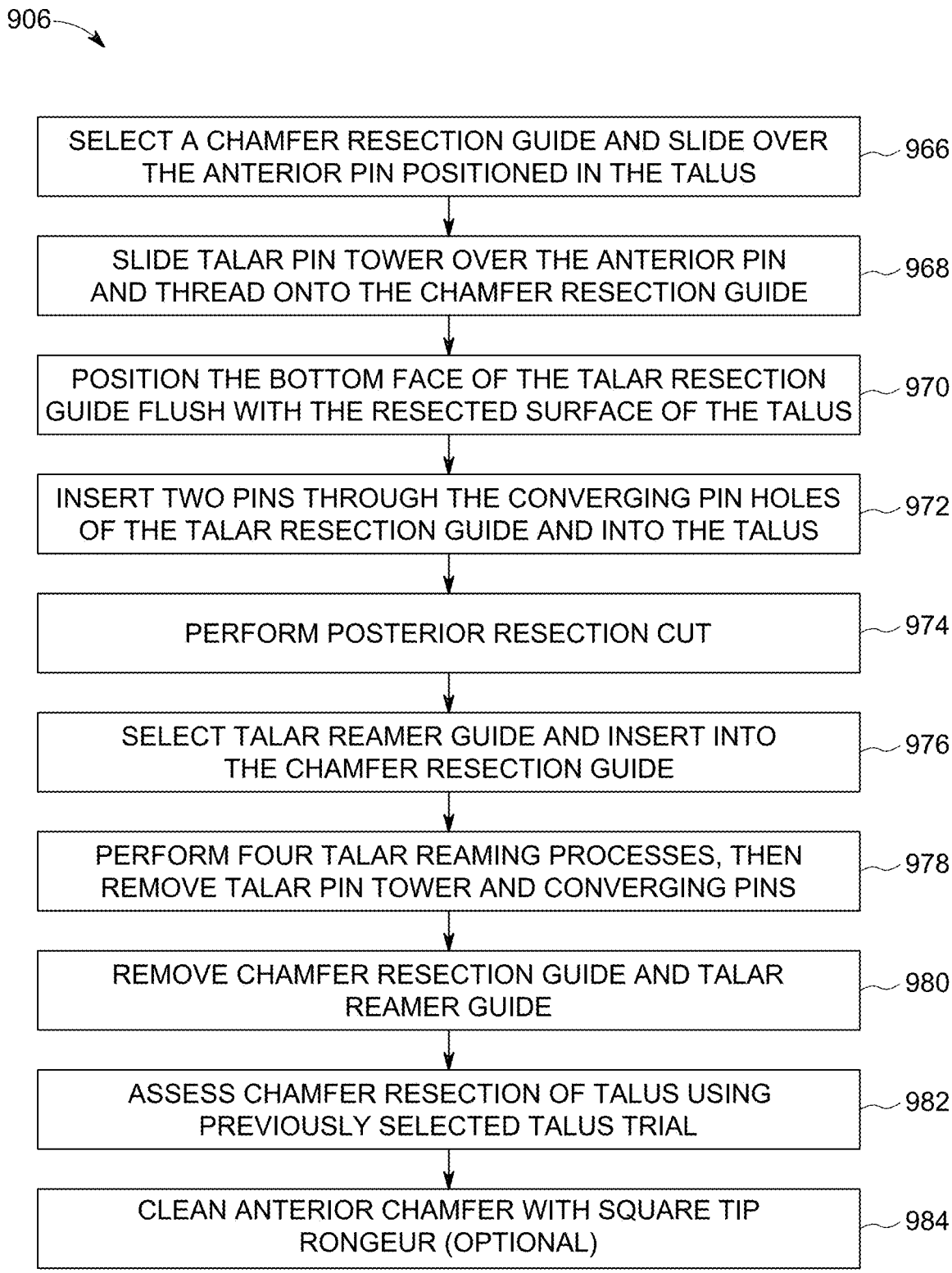
FIG. 22 is a flow chart illustrating a portion of the method of FIG. 16 for performing a talar chamfer resection, in accordance with an aspect of the present disclosure.

As shown in FIG. 22, a talar chamfer resection process 906 may include, for example, selecting a chamfer resection guide and sliding it over the anterior pin positioned in the talus 966 and sliding the talar pin tower over the anterior pin and threading it onto the chamfer resection guide 968. The talar chamfer resection process may also include positioning the bottom face of the talar resection guide flush with the resected surface of the talus 970 and inserting two pins through the converging pin holes of the talar resection guide and into the talus 972. In addition, the talar chamfer resection process may include performing the posterior resection cut 974. The talar chamfer resection process may further include selecting a talar reamer guide and inserting it into the chamfer resection guide 976, performing four talar reaming processes, and then removing talar pin tower and converging pins 978. The process may also include removing the chamfer resection guide and talar reamer guide 980 and assessing the chamfer resection of talus using previously selected talus trial 982. Finally, the process may optionally include cleaning the anterior chamfer with, for example, a square tip rongeur 984.

More specifically, the talar chamfer resection process 906 removing all of the trials, then selecting and sliding a chamfer resection guide over the anterior pin positioned in the talus. Then, the talar pin tower may be slid over the anterior pin and threaded into the chamfer resection guide. The bottom face of the talar resection guide may be positioned flush with the resected surface of the talus. Once the talar resection guide is positioned on the resected surface, two pins, for example, threaded shouldered pins may be inserted through the converging pin holes of the talar resection guide and into the talus. Next, an instrument, for example, a blade may be inserted through the posterior saw slot to make the posterior resection cut. After the posterior resection cut is complete, a talar reamer guide is selected and inserted into the chamfer resection guide. The talar reamer guide may be inserted, for example, with the letter "A" facing upright. An anterior chamfer reamer may then be used to ream through the holes in the face of the talar reamer guide. The talar reamer guide may include, for example, three holes although alternative numbers of holes are also contemplated. The talar reamer guide may then be rotated to position the letter "B" so that it is facing up and the reaming process may be repeated. Next, the talar reamer guide may be again rotated, this time to positon the letter "C" in the upright position and the reaming process may be repeated. Finally, the talar reamer guide may be rotated for third time to positon the letter "D" in the upright position and the reaming process once again repeated. After the four reaming processes are complete, the talar pin tower and the converging pins may be removed. Then, the chamfer resection guide and talar reamer guide may also be removed, leaving the anterior pin positioned in the talus. The previously selected talus trial may then be used to check for complete chamfer resections of the talus. If necessary, the anterior chamfer may then be cleaned up with a square tip rongeur. The talar chamfer trialing process 904 and the talar chamfer resection process 906 may be as described in greater detail in U.S. Provisional Application No. 62/779,092 entitled Instruments, Guides and Related Methods for Total Ankle Replacement, which is hereby incorporated by reference in its entirety.

Figure 23:
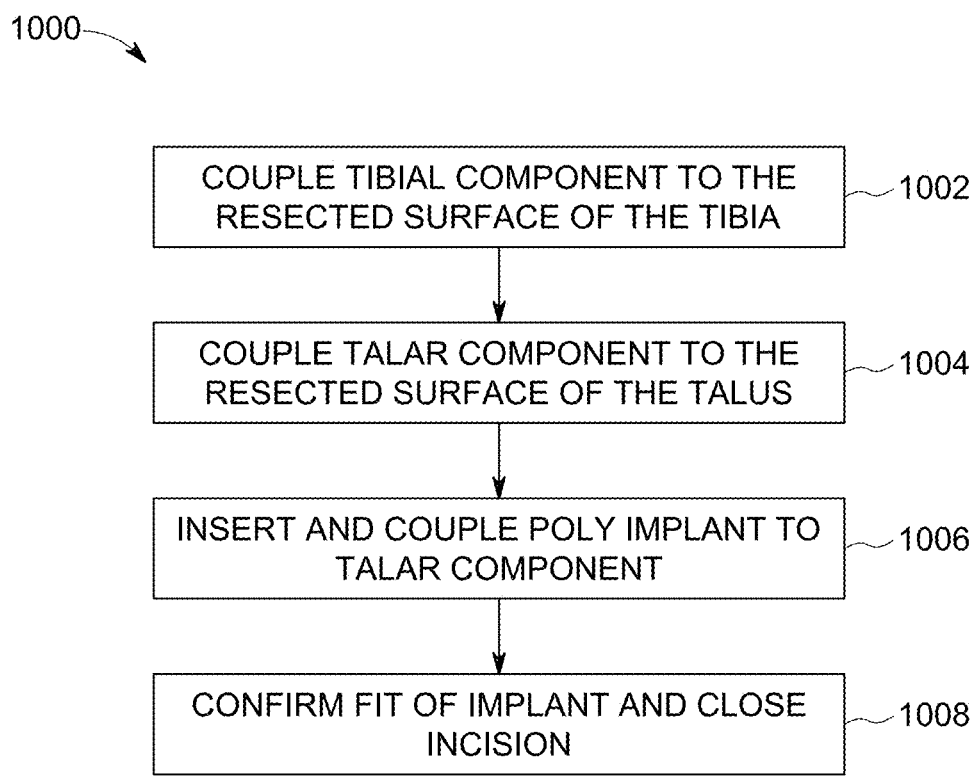
FIG. 23 is a flow chart illustrating a portion of the method of FIG. 1 for performing the implantation of components, in accordance with an aspect of the present disclosure.

As shown in FIG. 23, the method of implanting the components 1000 may include, for example, coupling the tibial component to the resected surface of the tibia 1002 and coupling the talar component to the resected surface of the talus 1004. Next, the method may include inserting and coupling the poly implant to the talar component 1006. The method may also include confirming the fit of the implant and closing the incision(s) 1008. The implant components may be as described in greater detail in International Application No. PCT/US2019/029009 entitled Implants and Methods of Use and Assembly, which is hereby incorporated by reference in its entirety.

Figure 24:
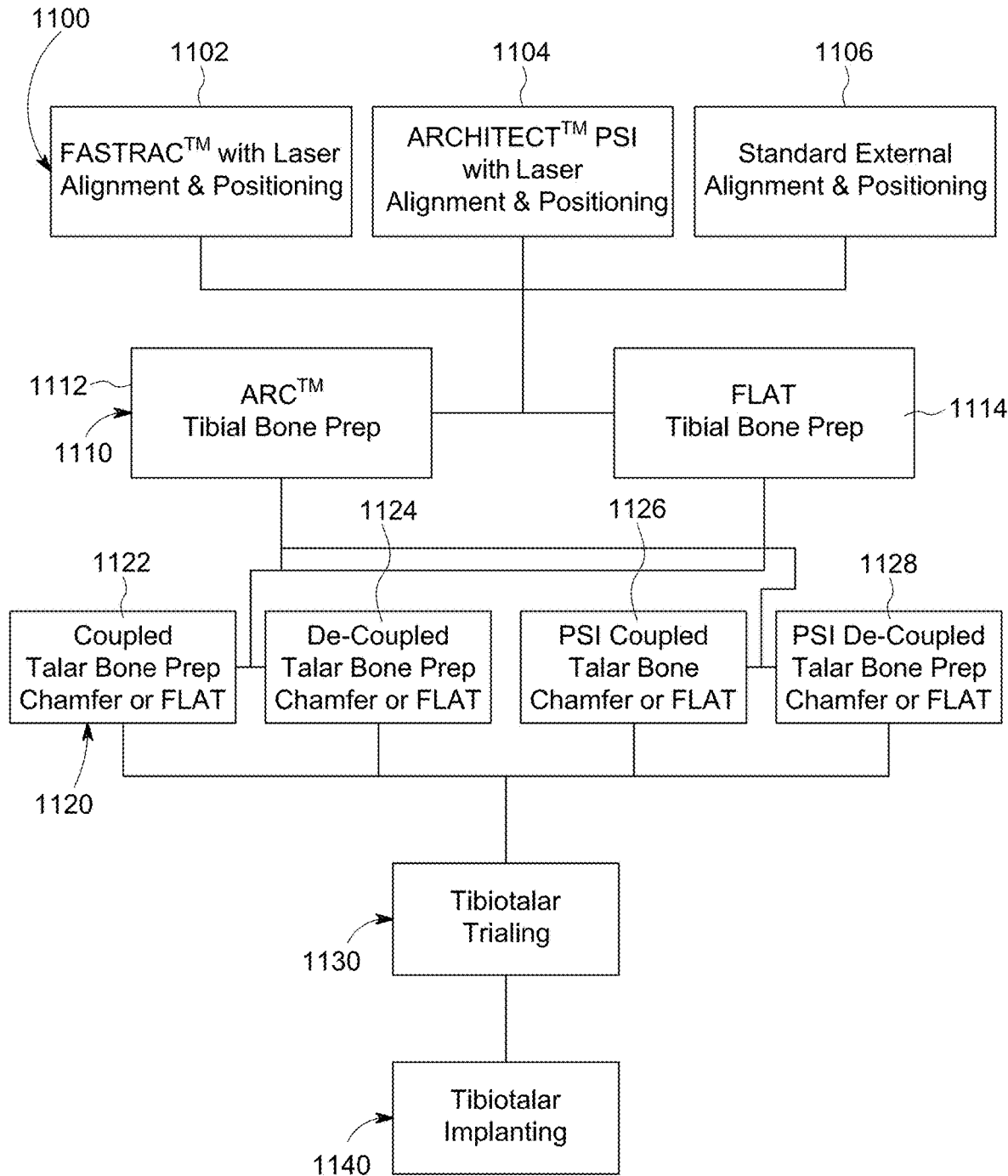
FIG. 24 is another flow chart illustrating an embodiment of a method for total ankle replacement, in accordance with an aspect of the present disclosure.
Figure 161:
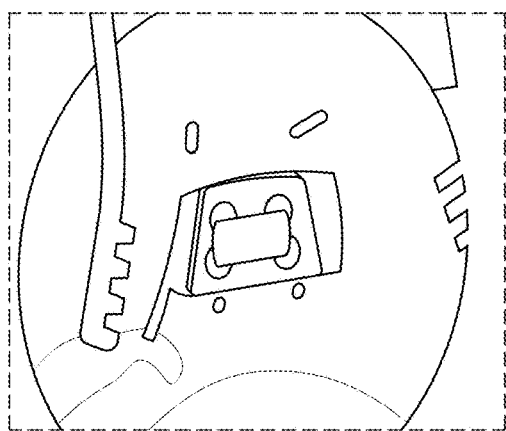

Referring now to FIGS. 24-161, additional methods of a TAR procedure are shown. As shown in FIG. 24, this surgical method includes aligning and positioning a guide on a patient's ankle 1100, preparing the tibial bone 1110, preparing the talar bone 1120, trialing the tibiotalar joint components 1130, and implanting the tibiotalar joint components 1140. The aligning and positioning of a guide on the patient's ankle 1100 may be performed using a fast track alignment guide with or without a laser 1102, a patient specific instrument with or without a laser 1104, and a full alignment guide 1106. The preparation of the talar bone may include preparing an arc surface 1112 or a flat surface 1114. The talar bone may be prepared, for example, using a coupled procedure to form a chamfered or flat surface 1122, a de-coupled procedure to form a chamfered or flat surface 1124, a patient specific instrument coupled procedure to form a chamfered or flat surface 1126, and a patient specific instrument de-coupled to form a chamfered or flat surface 1128.

When using the fast track alignment guide the method may include assembling the alignment guide 1150, 1200 as shown in FIG. 27. The fast track alignment guide 1150 may be assembled and the alignment guide may be set to a neutral and locked position. The locked position may be set by securing a first screw 1152, a varus-valgus knob 1154, medial-lateral knobs 1156, and internal-external lock screw 1158. The first screw or proximal/distal control 1152 may be rotated clockwise to raise the second translation mechanism or counterclockwise to lower the second translation mechanism until the proximal aspect of the control block is flush with the laser marked lines on the two vertical tracks. Once in the neutral position the second translation mechanism may be locked by rotating the screw 1160 until fully tightened. The method may include inserting the distal mating connection into the proximal end of the alignment guide, with the nose of the FASTRAC Alignment Jig facing either left or right, rotating the jig 90° to seat into place, ensuring the nose is facing anteriorly. Once seated, rotate the proximal most central screw on the control block clockwise until fully tightened. Now center the proximal turn knob and rotate clockwise by hand to tighten. The medial-lateral knobs 1156 may be rotated by hand, on either side of the construct to center the distal receiving dovetailed connection to 0. Then lock the position by rotating the distal most screw clockwise with the hex driver. The internal-external lock screw 1158 may be used to adjust internal/external rotation, insert the hex driver into the proximal most central screw and unlock by turning counter clockwise, allowing for rotational adjustments, then re-lock position by rotating the proximal most central screw clockwise with the hex driver.

Once the fast track guide 1150 is prepared an incision may be made over the ankle. Specifically, a longitudinal midline incision is made over the anterior ankle, beginning approximately 10 cm proximal to the ankle joint and terminating just distal to the talonavicular joint. The incision will start approximately 1 cm lateral to the tibial crest and will course just lateral to the tibialis anterior tendon. The initial incision should penetrate skin only, but no direct tension should be placed on the skin margins until full-thickness retraction is possible. Identify the superficial peroneal nerve and retract it laterally. Continue exposure to the extensor retinaculum. Identify the extensor hallucis longus (EHL) tendon below the retinaculum and divide the retinaculum longitudinally over the EHL tendon. Care should be taken to leave the sheath of the tibialis anterior (TA) tendon intact. Retract the EHL tendon laterally and the TA tendon medially. Identify the neurovascular bundle and retract it laterally with the EHL tendon. Continue exposure until the anterior capsule is visualized. Perform an anterior capsulotomy via a longitudinal incision. Elevate the capsule and periosteum over the anterior tibia and talus to expose the anterior ankle joint, the tibial plafond, the medial and lateral gutters and the anterior and dorsal talus.

The method may also include removing any anterior osteophytes over the tibiotalar joint line, allowing for exposure to the joint and to facilitate entry of instrumentation. The removal of anterior osteophytes includes removing any tibial osteophytes from the joint line extending to 1 cm proximal to the joint line and removing any talar osteophytes which may impede instrumentation entry and placement. If a dorsal boss is noted on the talus, removal of this boss should be performed with a wide, flat osteotome to provide a flush surface.

Figure 25:
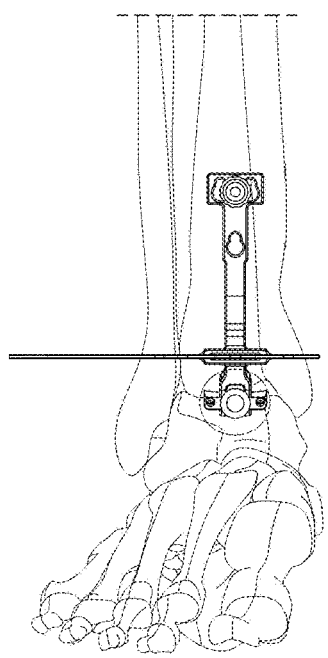
FIGS. 25-127 is a portion of the method of FIG. 24 using a fast track alignment guide, in accordance with an aspect of the present disclosure.
Figure 26:
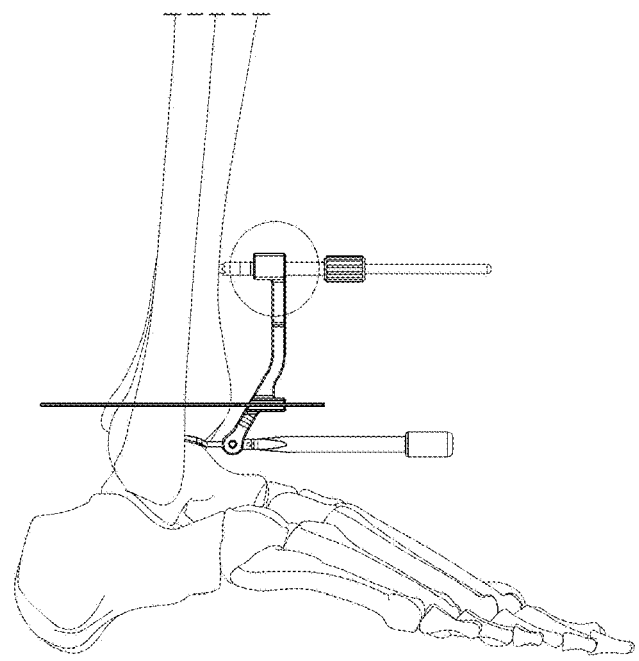

Referring now to FIGS. 25 and 26, the figures show provisional fixation and gross joint line height (JLH) processes being performed. Once the distal tibiotalar joint has been exposed, proceed to approximate JLH by gently inserting the flat posterior portion of the Joint Line Referencing (JLR) Pin Guide into the tibiotalar joint. Insert the Pin Tube Drill Guide into the distal most portion of the JLR Pin Guide, selecting one of the three slotted holed options. Then, under power, provisionally establish JLH by placing a 3.0×160 mm Fluted Pin into the selected proximal hole of the JLR Pin Guide. Repeat the process for the single slot just distal to the three slotted options, removing the Pin Tube Drill Guide once completed. To further assess and confirm JLH, take a lateral fluoroscopy, utilizing the Tibial Alignment Angel Wing and optional Lateral Rod to verify placement is parallel to the long access of tibial shaft by inserting the Angel Wing into the horizontal slot on the anterior face of the JLR Pin Guide, then inserting the JLR Rod into the posterior lateral receiving end of the Angel Wing, rotating the distal portion of the JLR Rod until tightly fixed to the alignment construct. Then compare the long axis of the tibia with the joint linc axis.

Alternatively, provisional fixation and gross joint line height (JLH) processes may be performed once the plafond and joint have been exposed, proceed to approximate the Joint Line Height (JLH) by gently inserting the flat posterior portion of the Joint Line Referencing (JLR) Pin Guide into the tibiotalar joint. Insert the Pin Tube Drill Guide into the single slotted hole, of the JLR Pin Guide, just distal to the three holed slotted options, targeting the flat portion of the anterior tibia, taking care to avoid the tibial crest. Under power, provisionally establish JLH by placing either a 3.0×(100/160) mm Fluted Pin into the selected proximal hole of the JLR Pin Guide. Repeat the process for the three holed slotted options, selecting the most appropriate option, then removing the Drill Guide once completed.

Figure 27A:
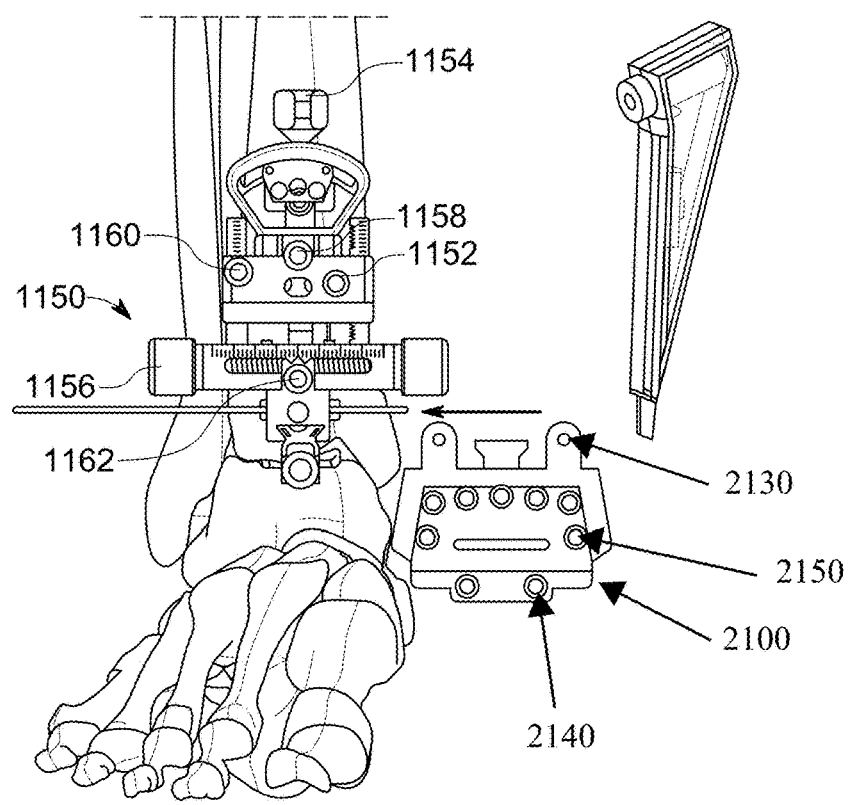
Figure 27B:
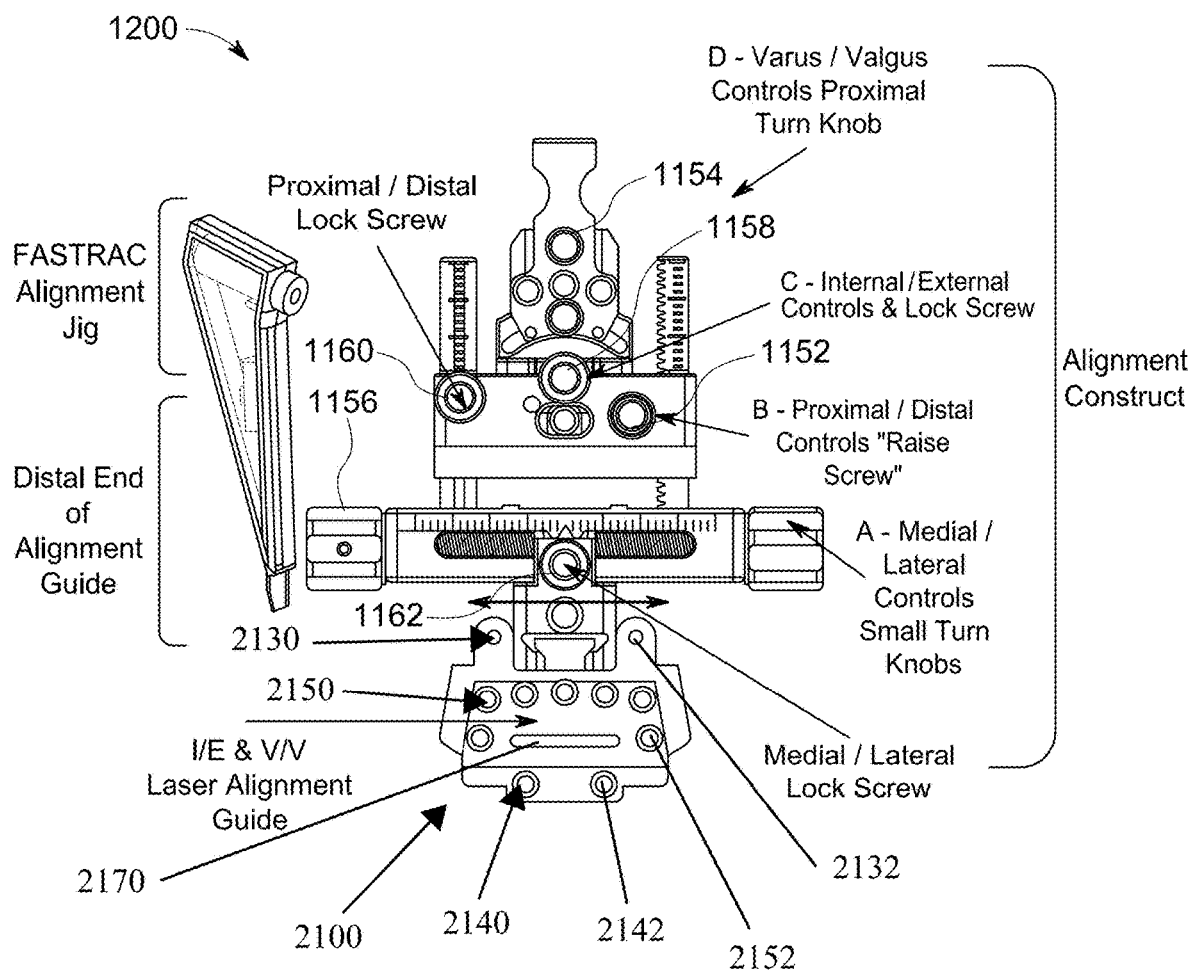

Referring now to FIG. 27A, the method may then include gross rotational and translational adjustments. Remove the JLR Pin Guide and attach the FASTRAC™ Alignment Construct by sliding one of the previously selected three holed options over the 3.0×160 mm fluted pins. Prepare to attach the Tibial Sizing Resection Block or resection guide 2100 based on estimated tibial sizing requirements. Based on preference, select from the ARC/Chamfer or FLAT/Flat guide options, then using the hex driver rotate the distal most "OPEN" screw counterclockwise allowing for insertion of the male dovetail portion of the receiving end of the FASTRAC Alignment Construct and locking by tightening the "OPEN" screw in a clockwise direction.

Alternatively, remove the JLR Pin Guide, then based on preference, position the FASTRAC™ Alignment Construct with either the Joint Line Pointer or desired ARC/Chamfer, FLAT/Flat, ARC/Flat, FLAT/Chamfer Tibial Sizing Resection Block options attached. Based on the selected option, use hex driver to secure it to the Alignment Construct by rotating the distal most "OPEN" screw counterclockwise allowing for insertion of the male dovetail portion of the receiving end of the FASTRAC Alignment Construct and locking by tightening the "OPEN" screw in a clockwise direction. Then slide the proximal most portion of the construct over the established 3.0 mm fluted pins. To further assess and confirm JLH, take a lateral fluoroscopy, utilizing the Tibial Alignment Joint Line Wing and optional Lateral Rod to verify placement is parallel to the long access of tibial shaft by inserting the Wing into the horizontal slot on the anterior face of the JLR Pin Guide, then inserting the JLR Rod into the posterior lateral receiving end of the Wing, rotating the distal portion of the JLR Rod until tightly fixed to the alignment construct. Then compare the long axis of the tibia with the joint line axis.

Figure 28:
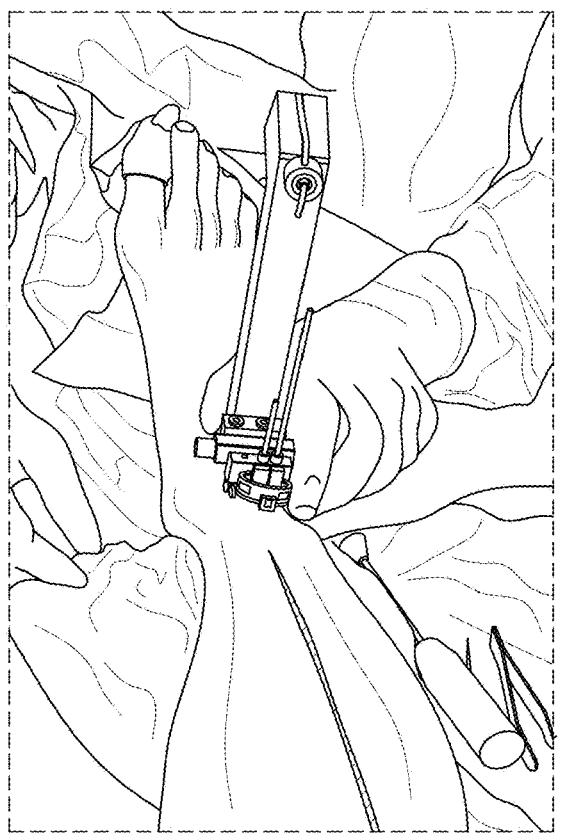
Figure 29:
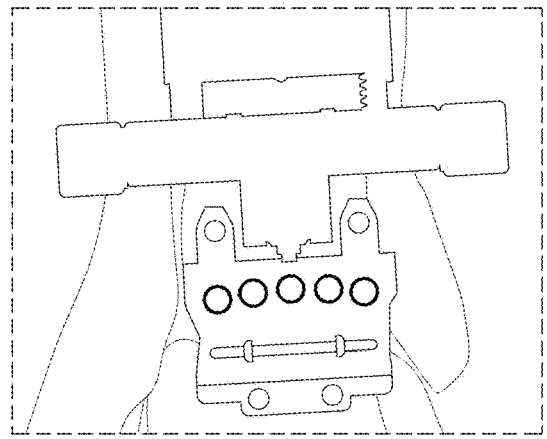

The method may also include gross positioning with a tibial alignment laser, as shown in FIGS. 28 and 29. Once the FASTRAC Alignment Construct is in place, verify the proximal turn knob, located on the FASTRAC Alignment Jig is fully tightened to help re-establish the initial alignment position. Insert the Alignment Gutter Tool into the medial gutter to evaluate medial/lateral position. Then with the Sizing Resection Block in place, evaluate proximal/distal positioning. To evaluate varus/valus alignment, retrieve the Tibial Alignment Laser and insert the distal self activating portion into the horizontal slot on the anterior face of the selected Tibial Sizing Resection Block, ensuring the laser window is pointed proximally, towards the operative limb then verify the green beam is targeting the tibial crest, roughly 10 cm distal from the tubercle. To assess Internal/External (I/E) rotation, verify the green beam is targeting the tibial crest, roughly 10 cm distal from the tubercle. Laser can be used to determine I/E rotation by inserting it into the joint line slot located in the center of the sizing resection block such that the green laser aligns between the second—third metatarsal respectively or by inserting an osteotome in the medial gutter to gauge position. Using fluoroscopy, shoot an AP image that confirms positioning prior to setting the position with two 2.4×110 mm Smooth Steinmann pins utilizing the radiolucent alignment markers within the Sizing Resection Block to help evaluate positioning. Lock in M/L alignment by rotating the center most distal most screw clockwise until the threads are fully seated.

Figure 30:
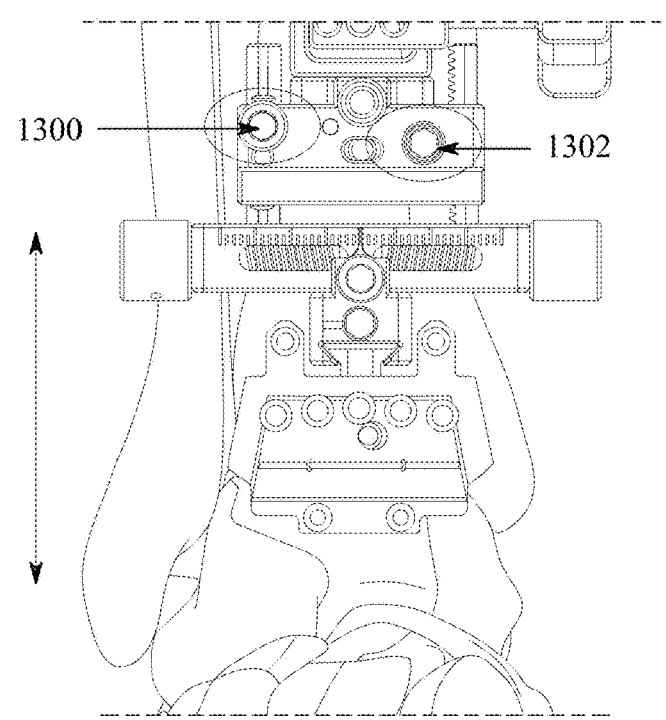

Referring to FIG. 30, the method may then include setting the fine distal-proximal positioning. Unlock the left screw 1300 on the FASTRAC Alignment Construct Control Block by rotating it counterclockwise until fully open. Using fluoroscopy under an AP view, evaluate and adjust gross joint line height by rotating the "RAISE" screw 1302 on the right side of the control block clockwise (to raise) or counterclockwise (to lower). Once appropriate positioning has been determined, establish fine joint line height by rotating the left gold screw clockwise until the threads are fully seated.

Figure 31:
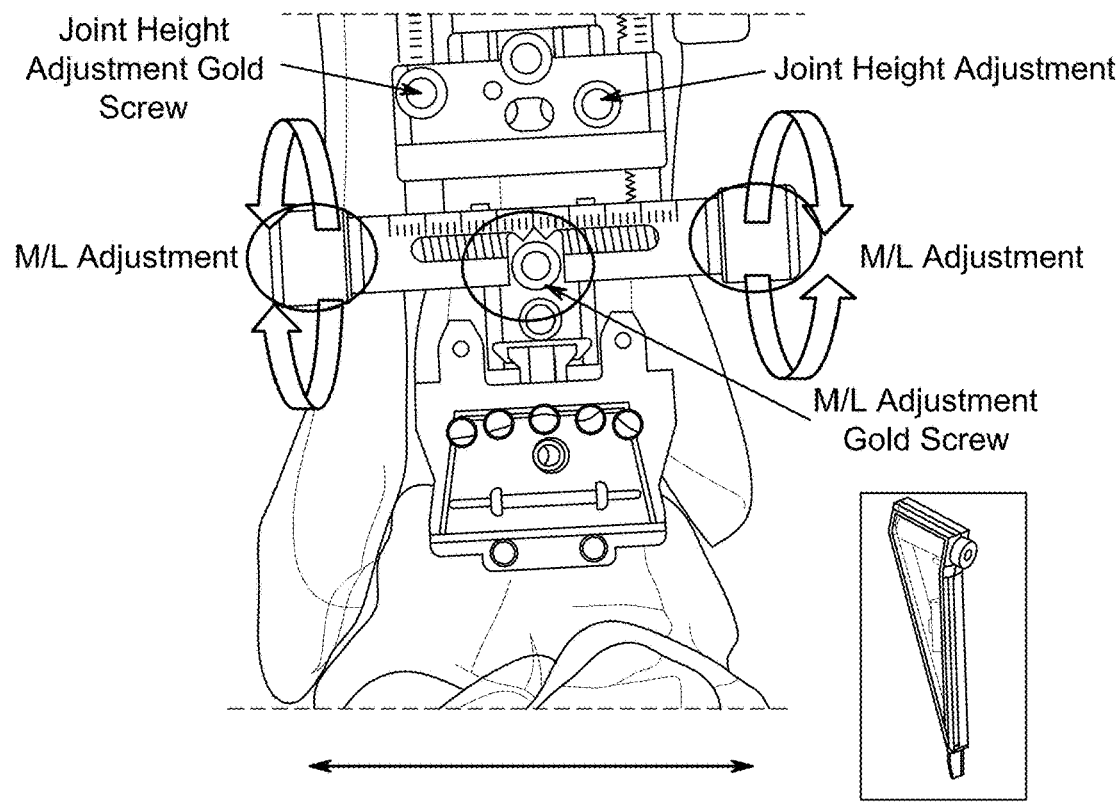

Next, the method may include setting the fine medial-lateral alignment, as shown in FIG. 31. Adjust medial/lateral (M/L) alignment by rotating the smaller turn knobs counterclockwise (to shift left) or clockwise (to shift right), using fluoroscopy in an AP view to verify the sizing resection block is appropriately aligned with the medial and lateral gutters. Lock in M/L alignment by rotating the center most distal screw clockwise until the threads are fully seated.

Figure 32:
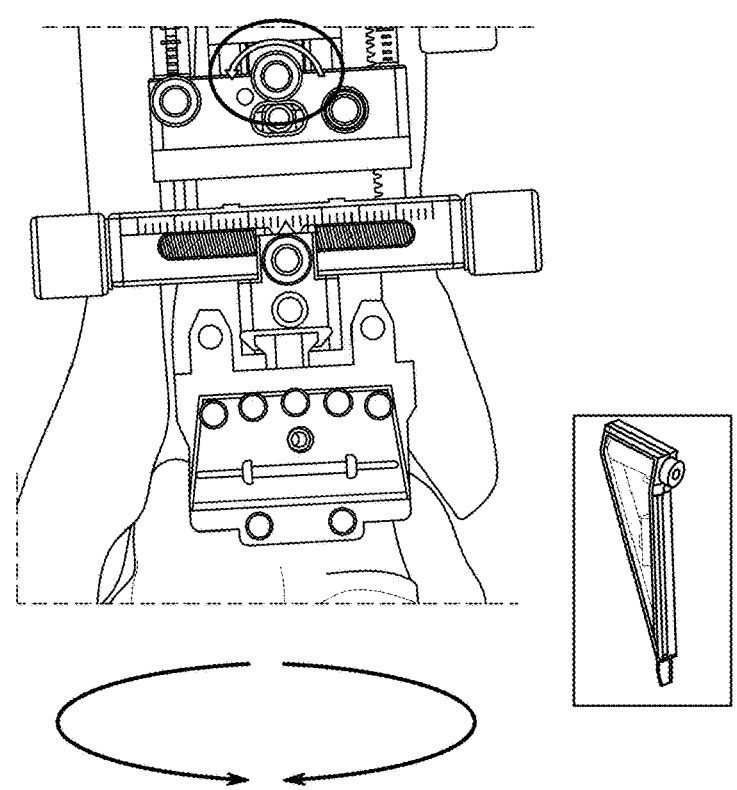

Then, as shown in FIG. 32, the method may include setting the fine internal-external rotation. Confirm internal/external (I/E) position visually by inserting the hex driver into the proximal most central screw and checking the position of the driver against the second metatarsal. If minor adjustments are needed at this time, remove the sizing resection block by unlocking the "OPEN" screw, and attach the Lateral Alignment Rod. Then unlock the proximal most center screw by rotating it counterclockwise and complete micro adjustments as needed. Once final I/E position is established, lock the distal most screw by rotating clockwise with hex driver. Laser can be used to determine I/E rotation by inserting it into the joint line slot located in the center of the sizing resection block such that the laser aligns with second metatarsal or by inserting an osteotome in the medial gutter.

As shown in at least, FIGS. 27A-27B and 30-44, the resection block or guide 2100 includes a body 2110 having a first side and an opposite second side. The body 2110 having a plurality of alignment pin through-holes 2130, 2140 extending from the first side to the second side of the body 2110 with openings 2132 on the first side of the body 2110 and openings 2134 on the second side of the body 2110. The body 2110 having a plurality of guide through-holes 2150 extending from the first side to the second side to define a first pattern of guide through-holes with openings 2152 on the first side of the body 2110 and openings 2154 on the second side of the body 2110. When the plurality of alignment pin through-holes 2130, 2140 of the body 2110 are support on a plurality of alignment pins attached to the first tibia bone, the openings 2154 of the guide through-holes 2150 on the second side of the body 2110 face the first tibia bone and the openings 2152 of the guide through-holes 2150 on the first side face away from the first tibia bone so that the first pattern of guide through-holes 2150 is operable for receiving a drill for use in resecting the at least a portion of the first tibia bone. A second resection guide 2100, such as shown in FIG. 41, includes a second pattern of guide through-holes 2150 offset from the first pattern. The resection guide 2100 includes a slot 2170 for guiding a cutting tool in the slot 2170 and into the talus of a patient.

Figure 37:
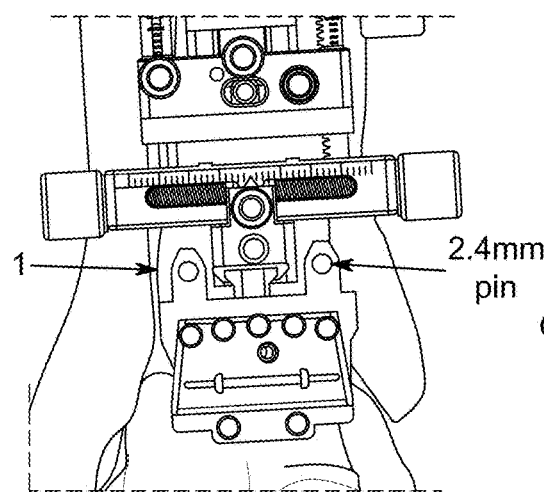
Figure 38:
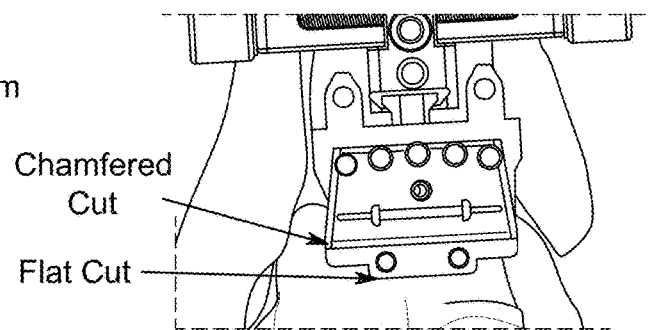

Referring now to FIGS. 33-35, the method may include setting the fine joint line height position. Perform final joint line height adjustments at this time. With either the Sizing Resection Block or Lateral Alignment Rod in place, insert the Angel Wing 1304 into the horizontal slot on the anterior face, then rotate the screw near the "RAISE" laser marking clockwise (to raise) or counterclockwise (to lower) until the radiopaque projection of the Angel Wing is at the joint line or desired joint line. Lock in joint line height by rotating the lateral screw in a clockwise direction. To ensure a true AP view of the ankle, ensure the Angel Wing projection is overlapping the posterior fluoroscopy marker of the Sizing Resection Block. FIGS. 36-38 illustrate the portion of the method for locking the medial-lateral alignment. Perform medial/lateral micro adjustment by rotating the small turn knobs on either side of the Alignment Construct in a clockwise/counterclockwise direction such that the medial corner of the drill holes is above the medial gutter. The lateral corner of the drill holes should be on the tibia near the syndesmosis. If a smaller or larger tibial implant size is necessary, remove the Sizing Resection Block and select the appropriate size and re-insert. Re-adjust the medial/lateral position of the Sizing Resection Block, if necessary. Lock in medial/lateral position by rotating the central distal screw in a clockwise direction. To lock final position against the tibia, place two 2.4×110 mm Smooth Steinmann Pins into the most proximal M/L holes of the Sizing Resection Block. Cut M/L tibia Steinmann Pins flush with provided Pin Cutters to offset pin depth to allow for easier transfer of tibial sizing resection block during subsequent steps. The talar cut height can be assessed at this point, using the Sizing Resection Block. If a chamfered talar cut is preferred, the cut height can be referenced from the proximal slot located on the distal aspect of the Sizing Resection Block. If a flat talar cut is preferred, the cut height can be referenced from the distal edge of the flat cutout between the distal most pin holes.

Figure 39:
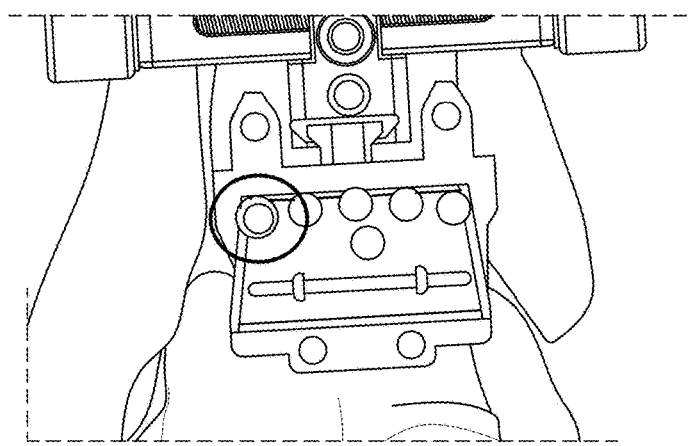
Figure 40:
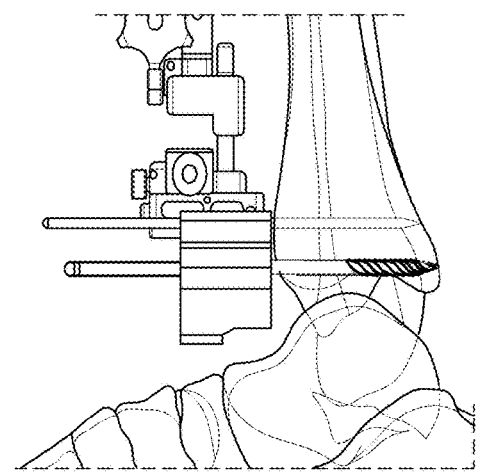
Figure 41:
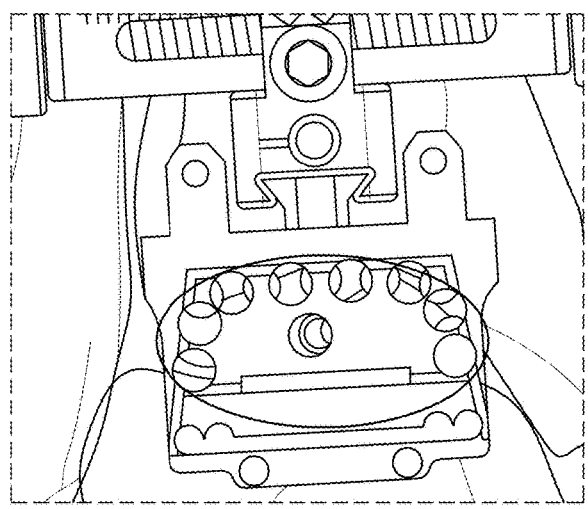

Next, a resection drill may be used for tibial joint preparation, as shown in FIGS. 39-41, such as a Bi-cortical ARC™ Resection Drill. Retrieve the 3.5 mm Tibial ARC Resection Drill. Under power, drill bi-cortically into the medial most corner hole of the Sizing Resection Block. Remove the drill and place the 3.5 mm Top Hat in the drilled hole to help secure the position of the block as the remaining holes are drilled. Laser markings on the ARC Resection Drill should be noted and are for reference only. The markings indicate the shortest likely distance the drill will need to travel to achieve bi-cortical drilling. Perform sequential bi-cortical drilling of the additional holes, using a pecking technique when nearing the posterior cortex to ensure that drilling occurs through the posterior cortex, but does not penetrate beyond. Then remove the Sizing Resection Block by rotating the "OPEN" screw counterclockwise and pulling the Sizing Resection Block off anteriorly. Prior to placing the ARC Tibiotalar Resection Block, ensure that the appropriate tibiotalar resection block is selected based on desired talar cut. Once the Tibiotalar Resection Block has been selected, slide the distal portion of the block over the two previously trimmed M/L 2.4 mm guide pins and into the dovetail connection on the Alignment Construct and tighten the "OPEN" screw clockwise to lock in place. Note the overlapping holes. As described above, perform sequential drilling with the 3.5 mm ARC Resection Drill, removing the remaining cortical bone, using a pecking technique when nearing the posterior cortex to ensure that drilling occurs through the posterior cortex, but does not penetrate beyond.

Figure 42:
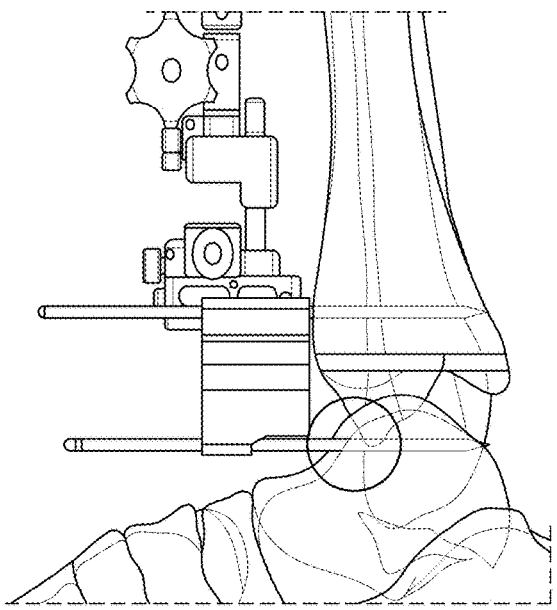

Referring to FIG. 42, the position is set into a neutral plantigrade tibiotalar position. If desired, position of the tibiotalar joint may be held with provisional fixation. Place two 2.4×110 mm Smooth Steinmann Pins into the distal holes of the Tibiotalar Resection Block into the talus. Cut the provisional 2.4 mm talar Steinmann pins flush with provided Pin Cutters, to offset pin depth, allowing for easier access of the saw blade in subsequent steps.

Figure 43:
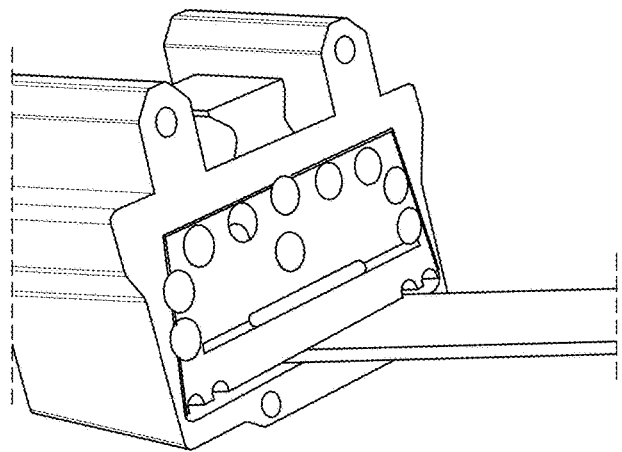

Then, a preliminary talar bone preparation may be performed, as shown in FIG. 43. With the 2.4 mm Smooth Steinmann Pins cut flush to the Resection Block, clearance for the saw blade has been achieved. Retrieve the provided 8×90 mm Oscillating Saw Blade to complete the initial talar dorsal cut. Cut the superior aspect of the talus through the cutting slot from a medial to lateral direction, then verify accuracy under a lateral fluoroscopy view. Take care to avoid contact of the saw with the medial malleolus and the fibula. Verify all Alignment Construct screws and knobs are still tight after the cut is completed.

Figure 44:
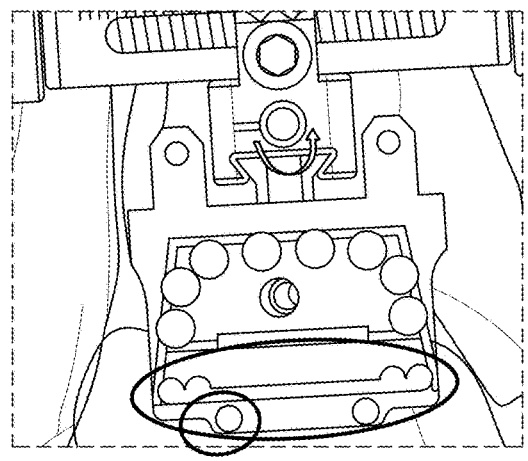

Next, the method may include resection block removal, as shown in FIG. 44. Remove the Tibiotalar Resection Block by rotating the "OPEN" screw counterclockwise and pulling the block anteriorly. Remove the 2.4 mm talar pins with the provided Pin Puller. For larger patients, the saw blade may not fully complete the posterior talar dome cut with Tibiotalar Resection Block in place. In this case, the 13×90 mm Oscillating Saw Blade can be utilized. Insert the saw into the cut portion, and finish the talar cut freehand, ensuring the entire posterior surface is cut from medial to lateral. Remove the talar cut bone from the operative site with the Square Tip Ronguer.

Figure 45:
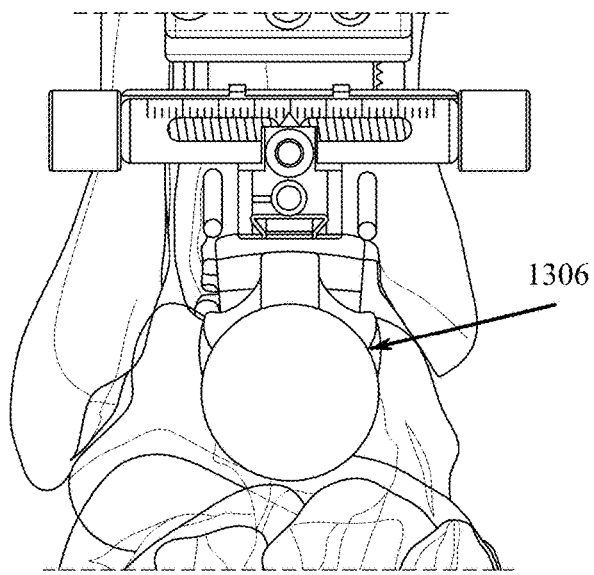

FIG. 45 shows another process in preparing the tibial joint preparation. Retrieve the ARC™ Osteotome 1306, align the leading edge against the ruffled cortical surface of the tibia, with slight pressure, advance the osteotome 1306 forward in a posterior direction, using a light upward pressure to ensure the tibial bone is evenly planed completely from medial to lateral and anterior to posterior. Striking the anterior aspect of the ARC Osteotome 1306 with a mallet during this process is not recommended. Fine rasping in subsequent steps will help achieve a smooth even surface. Once the appropriate tibiofibular ligaments have been completely released, retrieve the curved curette and Kocher forcep. Insert the curved curette lengthwise between the tibia and talus such that the curved portion is parallel to the cut surface of the tibia and talus. Once the curved curette has passed beyond the bone, rotate the curved curette 90° pointing superiorly behind the tibia fragment. Retrieve the Kocher forcep. Insert one side of the Kocher forcep between the tibia and talar cut surfaces and the second side into the tibia cut surface. Ensure that the posterior aspect of the bone is grasped by the Kocher forcep. Using the non-dominant hand, place counter pressure on the central aspect of the lower leg. Using the dominant hand, grip the Kocher forcep and curette. Pull the Kocher forcep and curette together directly anteriorly to retrieve the tibia bone fragment from the tibiotalar joint. Retrieve the 6 mm curved osteotome. Use the osteotome to release the Anterior Inferior Tibiofibular Ligament (AITFL), the Interosseous Ligament (IOL) and Posterior Inferior Tibiofibular Ligament (PITFL).

Figure 46:
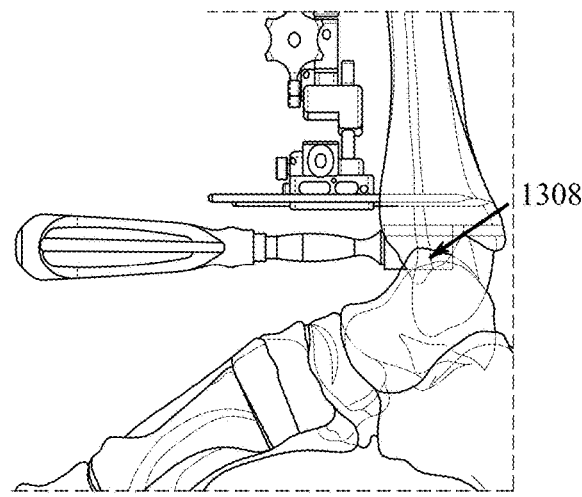

Referring now to FIGS. 46, the tibia may then be cleaned using, for example, a rasp tool 1308. After any remaining posterior fragments from the tibia and talus have been removed, confirm complete bone removal on a lateral view using fluoroscopy. Retrieve the corresponding sized Tibial ARC Rasp 1308. Rasp the tibial surface to ensure that no ridges remain between the drill portions, and that the posterior surface has been fully drilled. Gently push the tibial rasp 1308 posteriorly and pull anteriorly to smooth cortical surface, ensuring the rasp 1308 remains parallel with the resected distal tibial cortices. Then manually verify with finger sweep to check for any remaining bone or ridges. For softer bone, using a push only technique is recommended.

Figure 47:
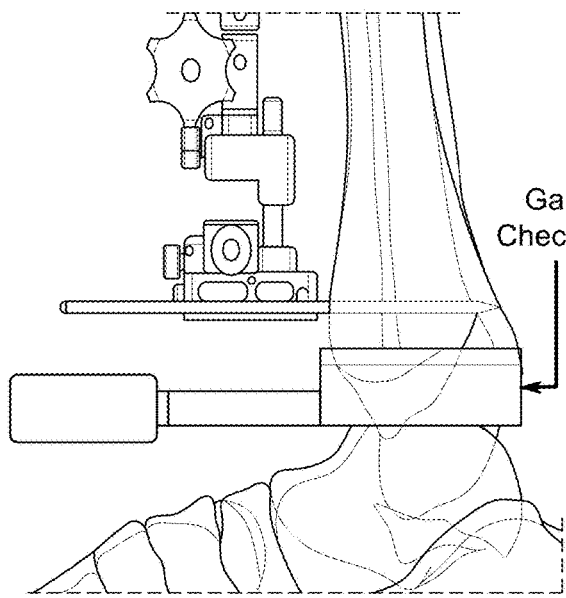
Figure 48:
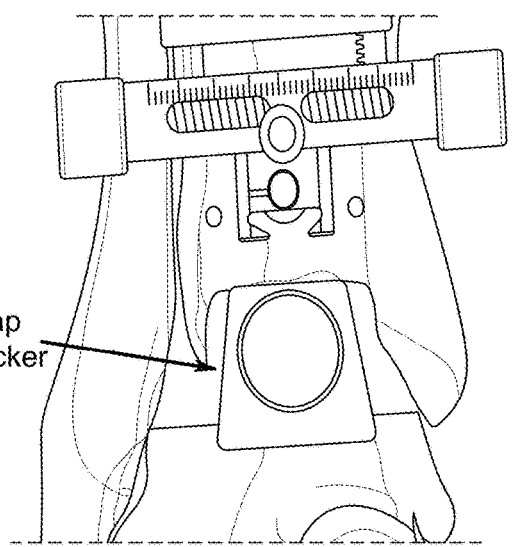
Figure 49:
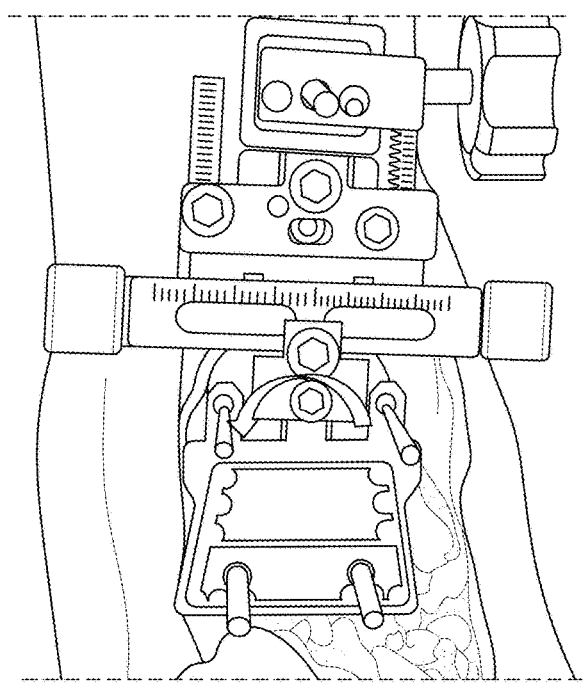
Figure 50:
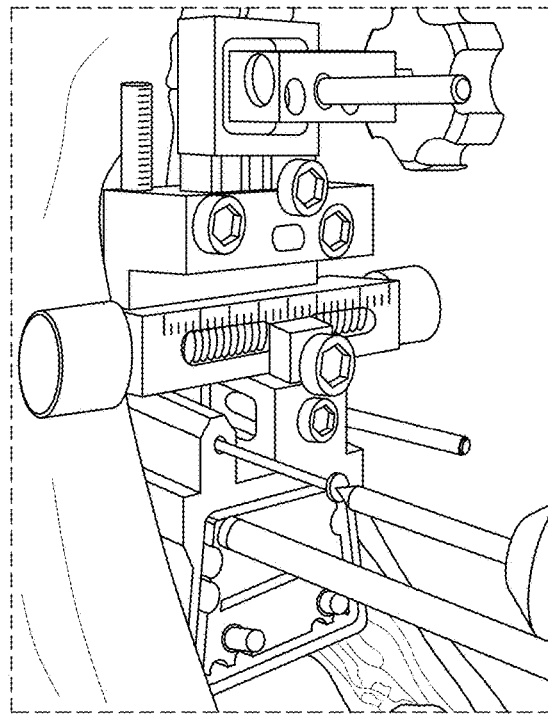

Next, as shown in FIGS. 47-48, the gap between the resected tibia and the talar surface is checked. Retrieve the corresponding cut style Tibiotalar Resection Gap Checker, and insert into the resected tibiotalar joint (i.e. Arc/Chamfer, Flat/Flat, etc cut style indicator is reflected by laser marking). Ensure the gap checker reaches the posterior aspect of the tibia and that no irregularity exists on fluoroscopy between the bone and the device. If necessary, remove any residual bone fragments that may be contributing to irregularity. Re-insert the Gap Checker to confirm congruent surface between the tibia, Gap Checker and the talus. Lateral and AP fluoroscopy views are helpful to evaluate and determine appropriate tibiotalar joint preparation.

Figure 51:
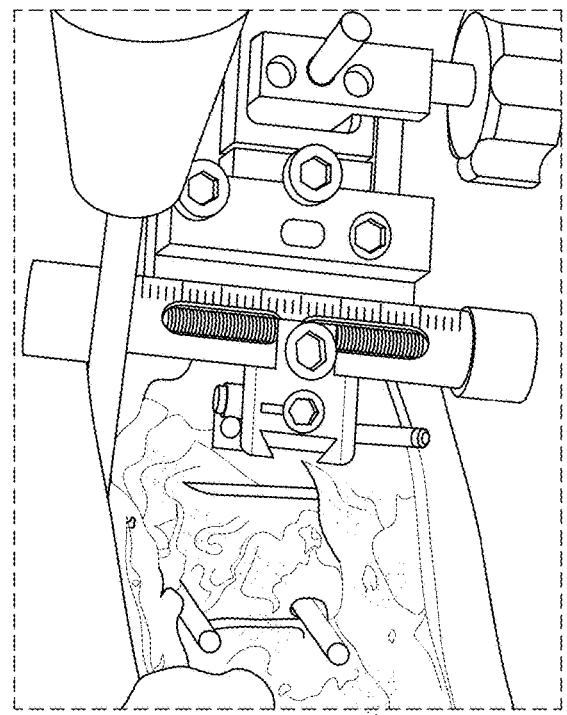
Figure 52:
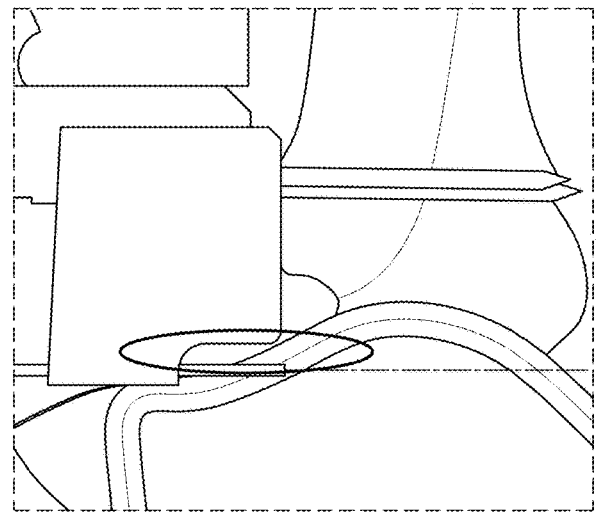

An alternative tibial joint preparation process for forming flat cuts is shown in FIGS. 49-53. Once fine positioning has been confirmed and locked, remove the Sizing Resection Block by rotating the "OPEN" screw counterclockwise fully and pulling the sizing resection block anteriorly. Retrieve the Tibial FLAT Cut Resection Block slide the distal portion of the block over the two previously trimmed M/L 2.4 mm Smooth Steinmann Pins and into the dovetailed connection on the Alignment Construct and tighten the "OPEN" screw clockwise to lock the flat tibia cutting block in. Place two 2.4 mm Steinmann Pins into distal talar Resection Block holes while compressing the tibiotalar joint space, prior to tibial drilling. Retrieve a Tibia Resection Drill. Using the Resection Drill, drill the medial and lateral holes in the Tibia Flat Resection Block. As shown in FIG. 51, a proximal cut and medial-lateral cuts may be made. Retrieve the provided 13×90 mm Oscillating Saw Blade. Perform the flat cut across the top of the FLAT Cut Resection Block starting medially and working laterally. Then, using either the provided Oscillating Saw Blade or 8×50 mm Reciprocating Saw Blade, cut through the medial and lateral slots on the FLAT Cut Resection Block starting distally and walking the saw blade up proximally. Next, as shown in FIG. 52, a distal cut may be made. Cut the 2.4 mm Steinmann talar pins flush to the Resection Block to allow for clearance of the saw blade. Place gutter pins (optional) around the talar cut. Retrieve the provided 8×90 mm Oscillating Saw Blade to make the talar dorsal cut. Cut the superior aspect of the talus through the cutting slot, taking care to avoid contact of the saw with the medial malleolus and the fibula. Then verify accuracy under a lateral fluoroscopy view.

Figure 53:
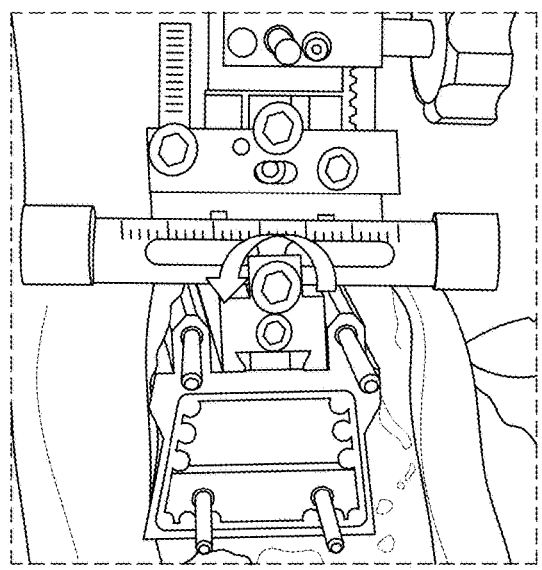
Figure 54:
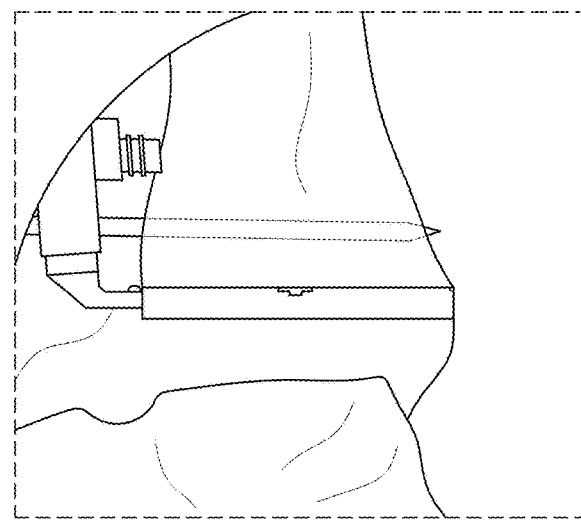

Finally, the resection block may be removed, as shown in FIG. 53. Remove the Resection Block by rotating the "OPEN" screw counterclockwise and pulling the Resection Block off anteriorly. Remove provisional Talar Pins with provided Pin Puller. Once initial cuts have been completed using the resection block as a guide, remove the block and complete any necessary or remaining free hand cuts, taking care to not cut past the existing cortical boundaries. Use of an osteotome or rongeurs is recommended to remove bone fragments.

Tibial trialing may be performed next, as shown in FIGS. 54-57. Retrieve the Tibial Trial size corresponding to the Sizing Resection Block. By hand, slide the Tibial Trial over the two medial/lateral 2.4 mm Smooth Steinmann Pins on the anterior aspect of the distal tibia and insert such that the anterior surface of the Tibial Trial is approximately flush to the anterior tibia. Center the pins in the slots to ensure appropriate varus/valgus and superior/inferior placement against the inferior surface of the tibia. Using lamina spreaders, distract the tibiotalar joint and confirm provisional tibial trial position using AP and lateral fluoroscopy. Tighten the tibial trial against the anterior tibia by rotating the distal most set screw on the tibia trial clockwise until the tibia trial and anterior tibia are flush. Using a lateral fluoroscopy view, determine tibia implant length. Ensure that the notch of the tibial trial comes into view on the lateral view. If the notch is located beyond the posterior tibia, a regular tibia size should be used. If the notch is located within the tibia, a long tibia size should be used, per surgeon preference. The center of the tibial trial notch should be aligned with the posterior tibia wall. It is recommended to use a long tibia size if uncertain whether the notch of the tibia trial is located within the tibia or not. Full anterior/posterior coverage with minimal overhang is preferred.

Figure 55:
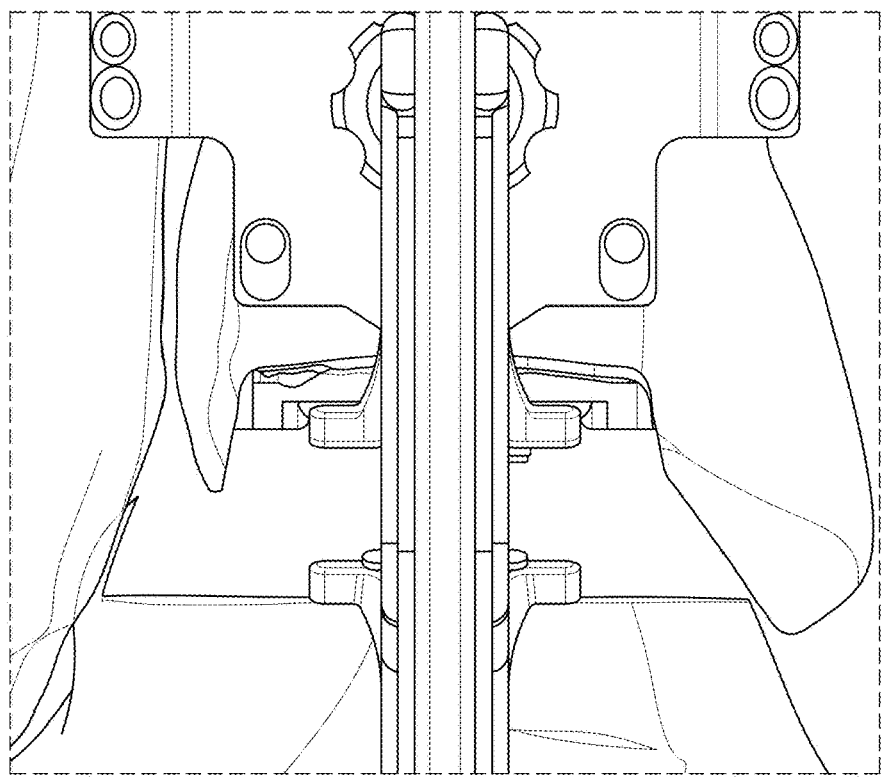
Figure 56:
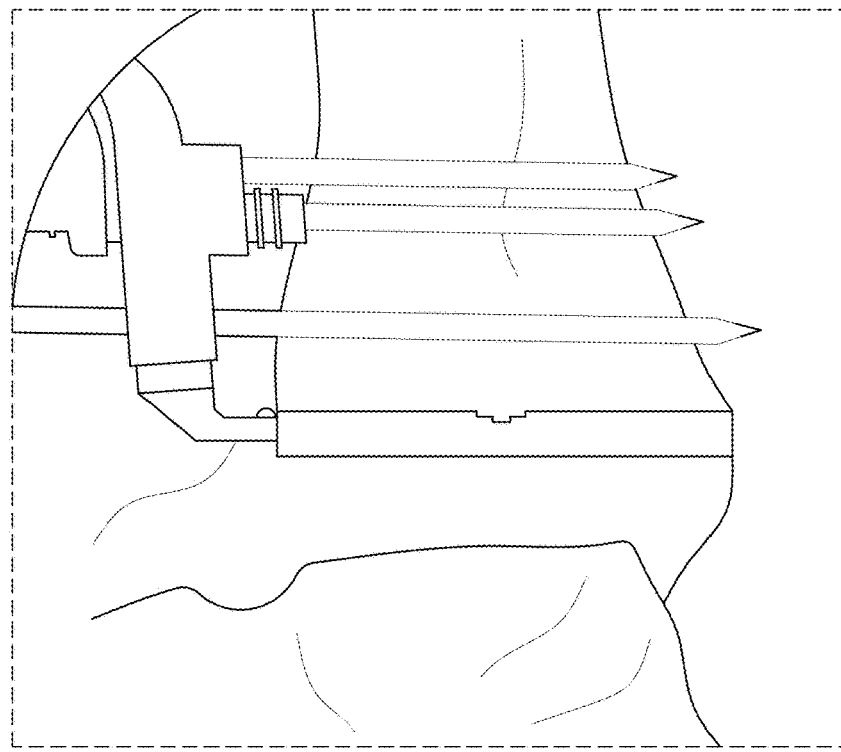
Figure 57:
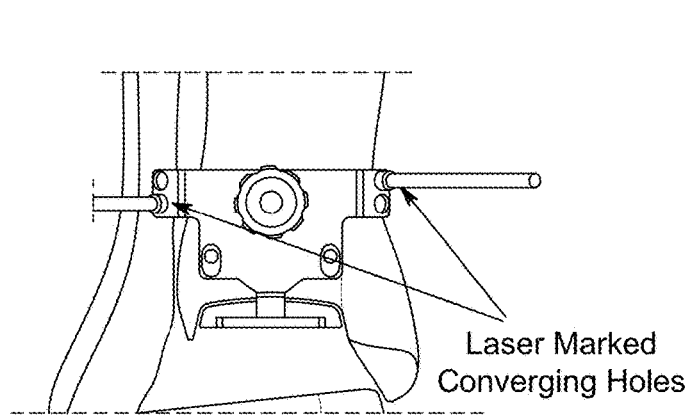

Referring now to FIG. 55, once sizing has been evaluated, retrieve the 4-Bar Parallel Distractor and attach the modular Tibial Trial Paddles. Insert the Parallel Distractor into the resected tibiotalar joint matching the superior paddle's dovetail connection to the inferior aspect of the trial. Distract the joint by squeezing down on the parallel distractor's handle, this will apply even pressure against the Tibial Trial and the talar cortical surface fully seating the tibial trial into position. Check Tibial Trial position on AP and lateral fluoroscopy views to ensure position and fit of the trial, for example, as shown in FIG. 56. In some embodiments, the tibial trial position may be checked by imaging while the distractor is still inserted within the joint. Next, as shown in FIG. 57, with the Parallel Distractor in place, insert two 2.4×50 mm Threaded Shoulder Pins into two of the 4 proximal converging pin holes, ensuring that either both laser marked holes are used together, or two non-laser marked holes are used together.

Figure 58:
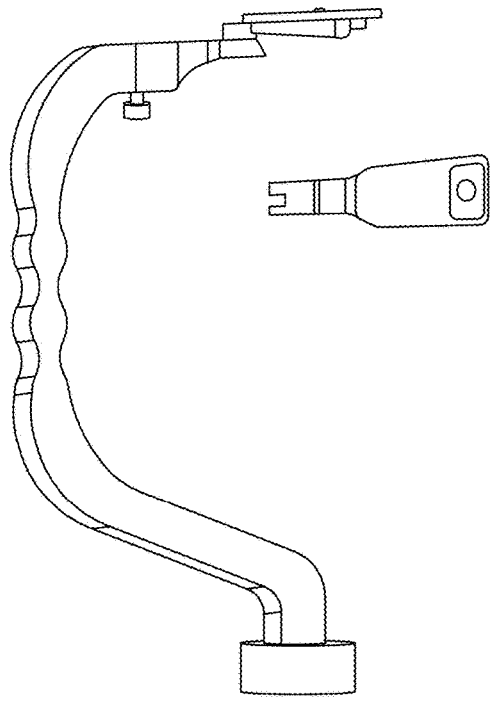
Figure 59:
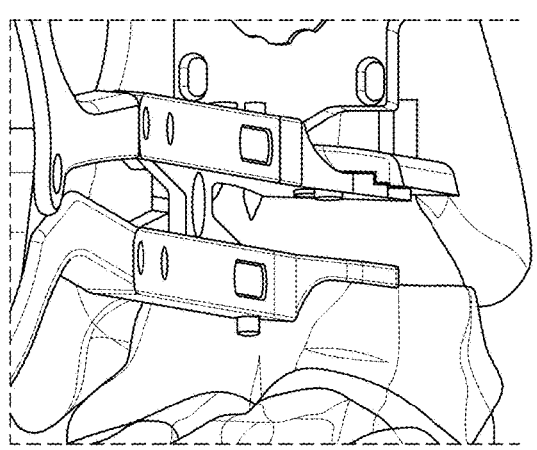
Figure 60:
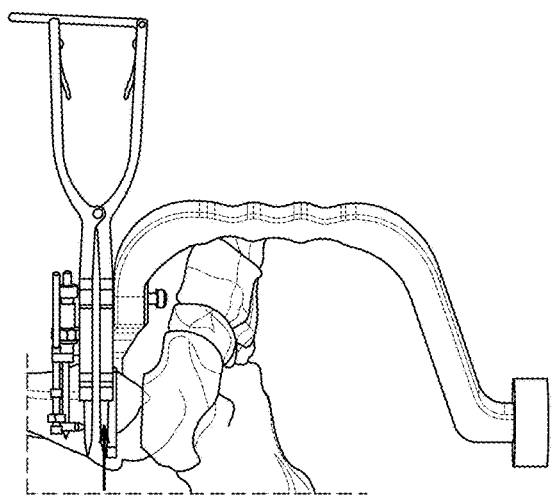

After the tibial trial has been correctly positioned, the method may include the tibial peg punch process. One peg punch process is shown in FIGS. 58-60. The first peg punch process may include, as shown in FIG. 58, Vertical Tibial Peg Preparation with a 4-Bar Distractor. Now that the converging shoulder pins have been put in place, remove the Parallel Distractor from the tibiotalar joint. Replace the corresponding proximal paddle of the Parallel Distractor with a Distractor Viper Tip Peg Punch Paddle, corresponding to the selected Tibial Trial size. In one embodiment, Retrieve the Tibia Impaction Tool and attach the (right or left) Tibia Impaction Dimpled Tool and have this modular tool construct available. FIG. 59 shows the Vertical Tibial Peg Punch with a 4-Bar to Impaction Tool. Insert the 4-Bar Parallel Distractor into the resected tibiotalar joint, ensuring that the Viper Tip Peg Punch Paddle is facing superiorly. Align the pegs with the inferior holes in the Tibial Trial, verifying position using AP and lateral fluoroscopy as well as visually. Begin to distract the Parallel Distractor under lateral fluoroscopy. FIG. 60 shows using the previously assembled Tibia Impaction Tool construct, insert the Impaction Dimple underneath the Viper Tip Peg Punch Paddle. Impact the distal end of the Impaction Handle, still under 4-Bar distraction until the Peg Punch Paddle is fully seated.

Figure 61:
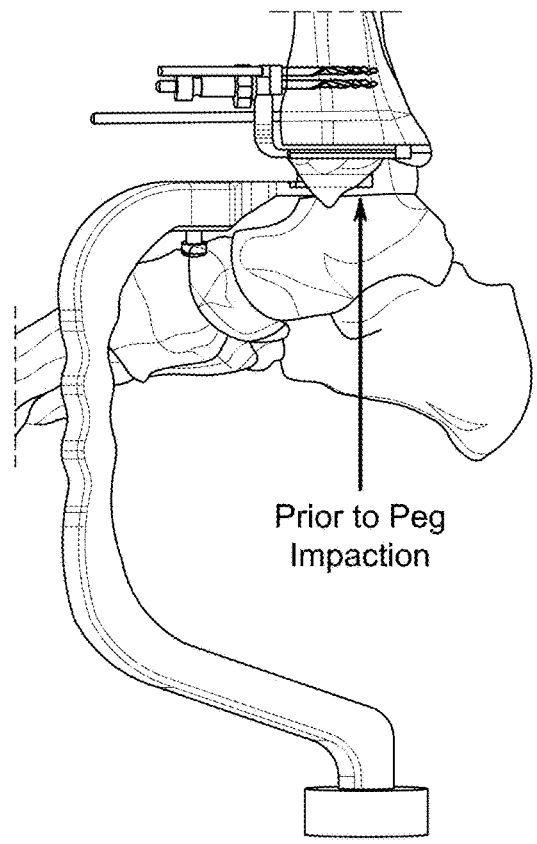
Figure 62:
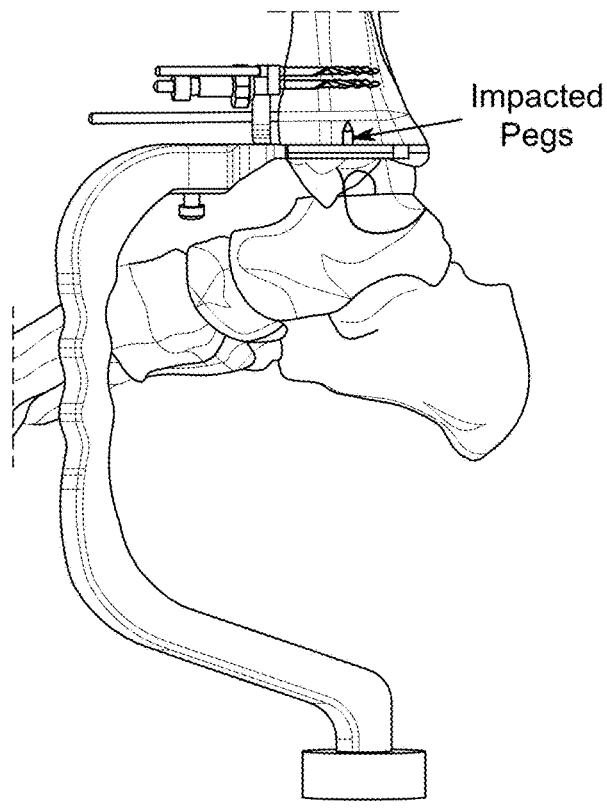

A second peg punch process is shown in FIGS. 61-62 and includes as shown in FIG. 61, a Vertical Tibial Peg Preparation with Impaction Handle. Now that the converging shoulder pins have been put in place, remove the Parallel Distractor from the tibiotalar joint. Retrieve the (right or left) modular Impaction Peg Punch corresponding to the size of the Tibial Trial. Place the Impaction Peg Punch such that the projections align with the holes on the inferior aspect of the tibial trial. Now attach the Impaction Handle Tool to the Impaction Peg Punch. Both visually and under fluoroscopy, ensure that the Impaction Peg Punch is perpendicular to the long axis of the tibia verifying position using AP and lateral view. FIG. 62 shows under fluoroscopy, using a mallet on the distal end of the Impaction Handle construct to impact the pegs into the tibia. Confirm that complete seating of the pegs has occurred relative to the Tibial Trial by direct visualization under fluoroscopy. In one embodiment, care should be taken, over impaction of the peg punching spikes should be avoided if possible. Two to four moderate strikes on the distal end of the impaction handle construct are sufficient.

Figure 63:
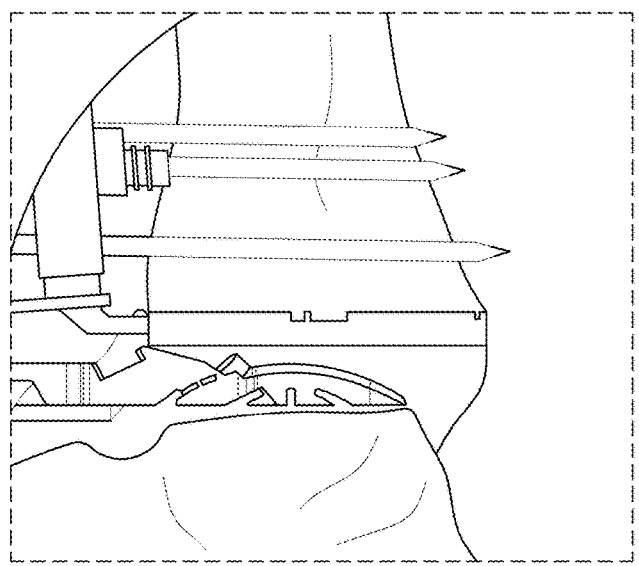

Next, the method may include talar trial positioning for chamfer cutting, as shown in FIGS. 63 and 64. FIG. 63 shows a Chamfer-Cut Talar Trial Positioning Retrieve the estimated 4-Bar Talar Trial Lollipop Sizing Resection Guide option. By hand, initially place the modular guide into the joint to evaluate coverage. Visually and under fluoroscopy, confirm the guide size by assessing coverage on talus, ensuring that the lollipop adequately covers the medial and lateral aspect of the dorsal cut without impinging on the gutters and vertical line on trial aligns with the lateral process. Once sizing has been evaluated, retrieve the 4-Bar Parallel Distractor and attach the selected modular Talar Trial Sizing Resection Guide. Re-insert the guide into the resected tibiotalar joint, matching the superior paddle's dovetail connection to the inferior aspect of the Tibial Trial and the inferior aspect of the Talar Trial Sizing Resection Guide to the resected talar bone. Referring now to FIG. 64, distract the joint by squeezing down on the 4-Bar Parallel Distractor Handle, applying even pressure against the Tibial/Talar Trial Guides and the tibiotalar cortical surfaces preparing to fully seat the Talar Trial Resection Guide into position. With the Parallel Distractor in place, re-check the Talar Sizing Resection Guide position under a lateral fluoroscopy view to ensure position and fit before setting into place with shoulder pins. The selected Talar Trial Guide can be sized up or down by 1 to achieve appropriate coverage. Plantarflexing the tibiotalar joint to achieve appropriate visualization before setting in place is recommended.

After the tibial trial is positioned, the method may include talar trial placement as shown in FIGS. 65-67. FIG. 65 shows Chamfer-Cut Talar Trial Placement. Under the same view, ensure that the cutting slots for the anterior and posterior chamfers are resecting an appropriate amount of talus. With the Talar Trial Sizing Resection Guide attached to the 4-Bar Parallel Distractor and positioned in place, prepare to insert a 2.4×110 mm Smooth Steinmann Pin into the medial anterior pin hole and two 2.4×25 mm Threaded Shoulder Pins into the slightly converging medial/lateral pin holes as described below in the subsequent steps. In one embodiment, the subsequent pin fixation steps are critical. Care should be taken to establish an appropriate position. FIGS. 66 and 67 show Chamfer-Cut Talar Trial Guide Pin Fixation. For example, place a 2.4 mm Smooth Steinmann Pin into the medial anterior hole in the Talar Sizing Resection Guide and retrieve two Threaded Shoulder Pins. Plantarflex the foot to expose the converging pin holes located more posteriorly on the guide. Under power, place the medial anterior pin into the guide, stopping pin insertion prior to touching the shoulder against the guide. Under power, place first shoulder pin into the medial hole of the Sizing Resection Guide. Place a second shoulder pin into the lateral hole of the guide. Advance the shoulder pins slowly using a ream setting. Disconnect the 4-Bar Parallel Distraction Handle, then using the supplied Pin Cutters, trim the medial anterior 2.4 mm Smooth Steinmann Pin. Also, if not previously cut, now trim the central pins on the Tibial Trial flush to the anterior surface to provide clearance for Talar Plunging Reamer.

The method may then include resection of the talar bone, as shown in FIGS. 68-70. FIG. 68 shows the Posterior Talar Chamfer Cut including evaluating access to the posterior cut slot within the Talar Sizing Resection Guide. If access to the posterior cut slot is favorable, retrieve the provided 8×90 mm Oscillating Saw Blade used for the dorsal talar cut, and prepare to complete the posterior chamfer cut. Insert the saw blade into the posterior cut slot of the Talar Sizing Resection Guide. Now, under power, perform the posterior saw cut, taking care to avoid contact with the medial malleolus and fibula. FIG. 69 shows the Chamfer-Cut Talar Bone Resection including placing the anterior Talar Lollipop Chamfer 2-Holed Resection Insert, corresponding to the size of the Sizing Resection Guide, into the anterior window of the guide. Place the corresponding sized Plunging Reamer into one of the two anterior holes, holding it perpendicular to the 2-Holed Resection Insert. Wait to start the reamer until lightly pressed against the cortical bone. Under power, ream until the Plunging Reamer bottoms out against the 2-Holed Resection Insert. Then, repeat this reaming step for the second anterior hole. FIG. 70 shows removing the 2-Holed Resection Insert or sweeping reamer 2300. The sweeping reamer 2300 having an elongated slot 2350. Place the Talar Lollipop Chamfer Single-Slotted Resection Insert into the same anterior face of the Sizing Resection Guide. Using the Plunging Reamer, slide the reamer 2390 from left to right until the bridge between the two reamed holes is resected, then remove the Single-Slotted Resection Insert.

Figure 71:
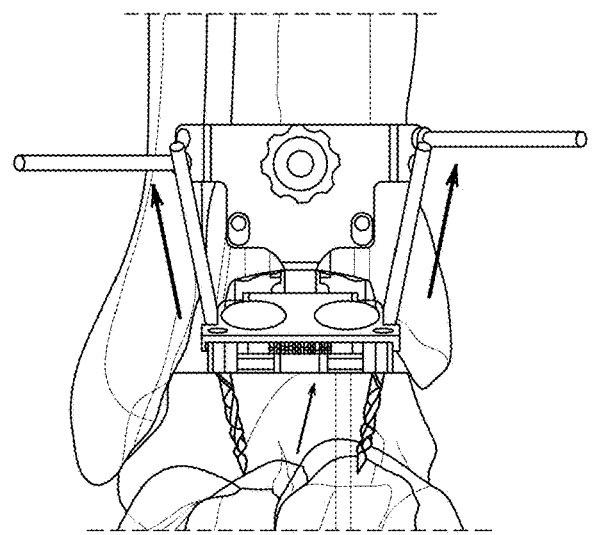
Figure 72:
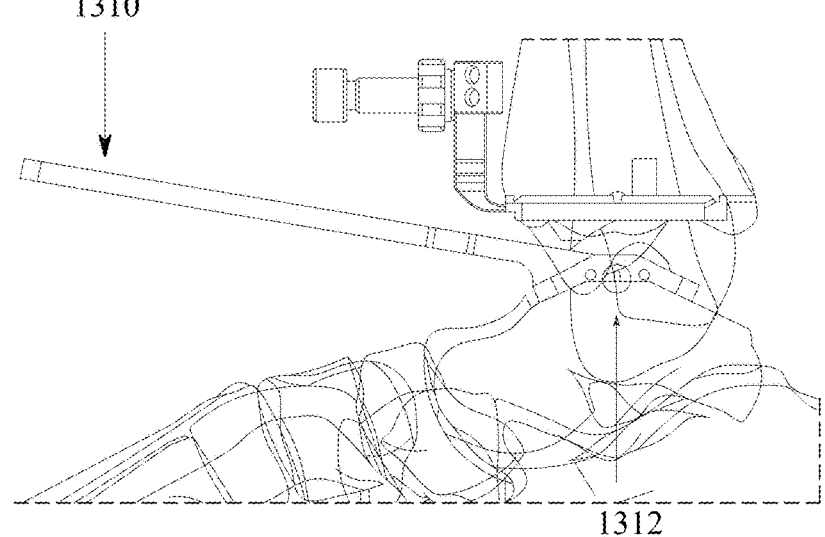

After the initial talar bone resection is complete, the final talar bone preparation is performed, as shown in FIG. 71. The Chamfer-Cut Talar Bone Resection Final Preparation includes removing the Threaded Shoulder Pins from the Talar Sizing Resection Trial. Remove the medial anterior pin from the Sizing Resection Trial as well, then remove the Sizing Resection Trial. In one embodiment, using a sagittal or reciprocating saw in a freehand manner, finish the posterior talar chamfer cut, if necessary. Once the talar bone preparation is complete, the chamfer cut may be verified, as shown in FIG. 72. Verify Chamfer-Cut by removing the posterior talar bone using a pituitary rongeur. Palpate or visually review talar cuts. Check the anterior cut for any residual bone. Use the Square Tipped Rongeur to finish the anterior cut, ensuring that the medial and lateral edges of the cut are completely resected. Retrieve the all-in-one Chamfer Checker 1310 to evaluate chamfer cuts. Insert into the tibiotalar joint and review the central fluoroscopic marker 1312 of the Chamfer Checker 1310 to ensure that a perfect lateral view is obtained. If any incongruencies are present anteriorly or posteriorly under fluoroscopy, correct any incongruencies at this time.

Figure 73:
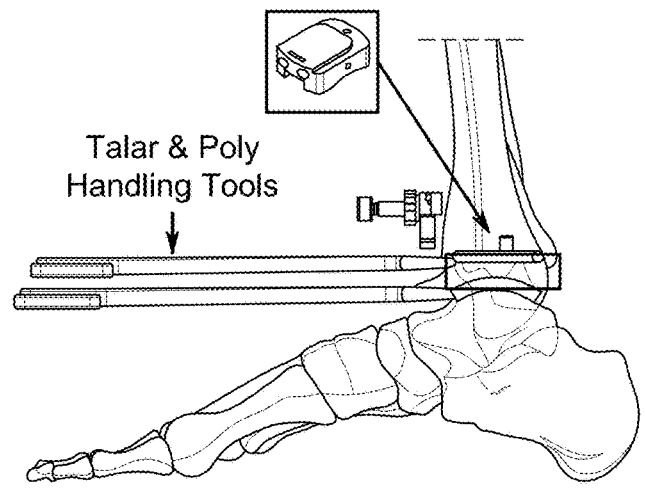

As shown in FIG. 73, the method also includes talar and poly trial placement. The Chamfer-Cut Talar and Poly Trial method includes using the Talar Trial Handling Tool and placing the corresponding Talar Chamfer Trial into the resected tibiotalar joint. Attach the selected Poly Trial to the Poly Trial Handling Tool and insert the Poly Trial into the joint such that the dovetail on the Poly Trial connects with the dovetail of the Tibial Trial, a click will be felt or heard. Then, check the Talar Trial placement and size using AP and lateral fluoroscopy. Put the tibiotalar joint through gentle range of motion evaluation to ensure adequate placement and correct poly trial thickness. In one embodiment, ensure that the fluoroscopic notch on the talar trial is visible on lateral fluoroscopy to ensure that a perfect lateral radiograph is taken when checking talar cuts. Also, poly trial is equipped with M/L Fluoroscopy markers to help determine fit and placement.

Figure 74:
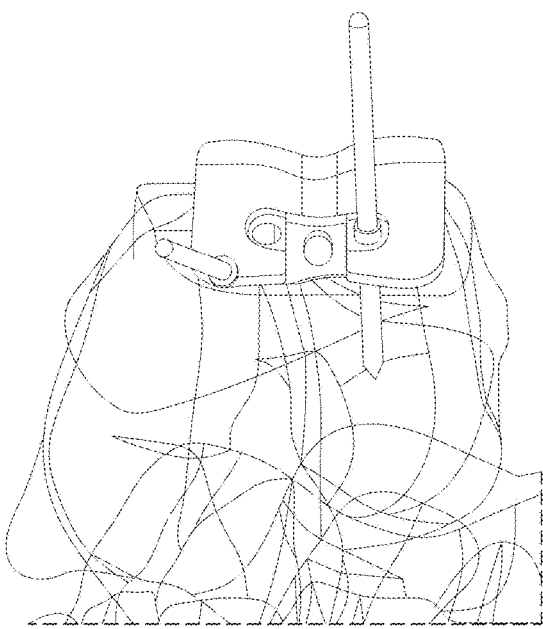
Figure 75:
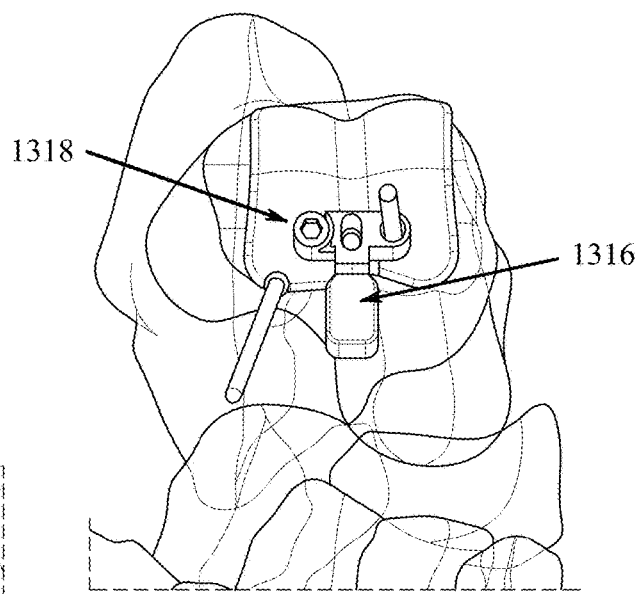
Figure 76:
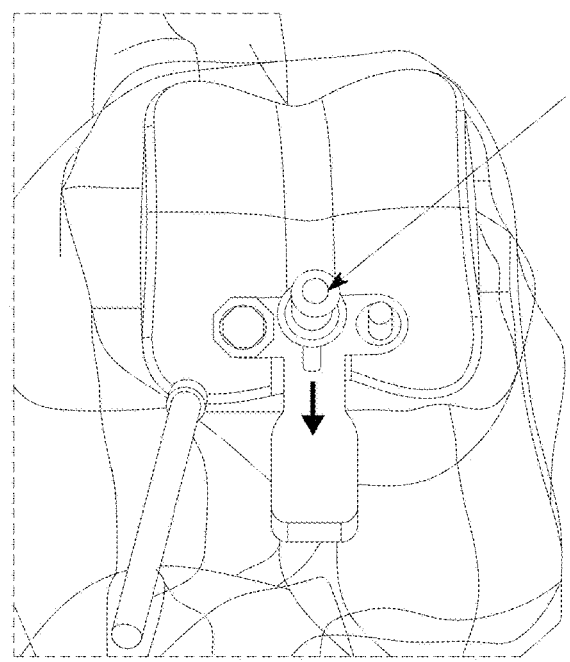
Figure 77:
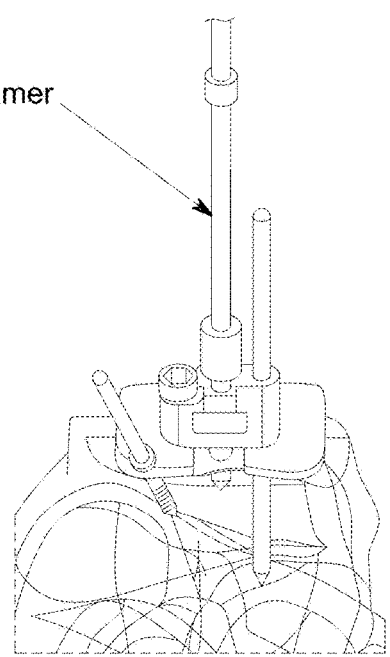
Figure 78:
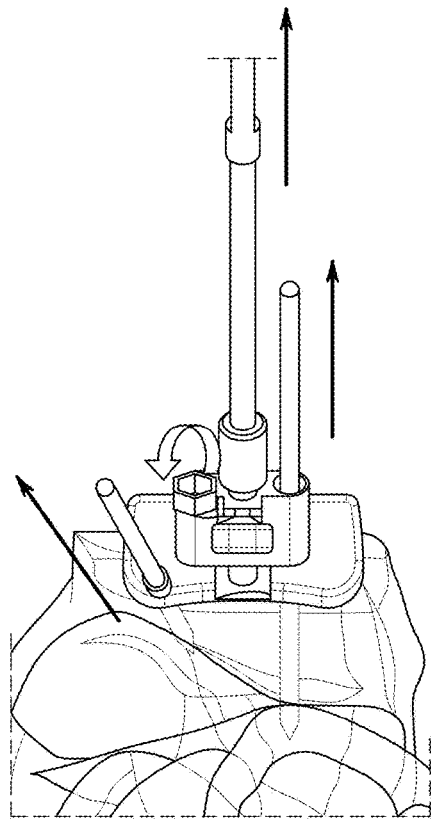

Next, the shoulder pins are placed in the talar trial, as shown in FIG. 74. Placing the shoulder pins includes under power, place a 2.4×25 mm Threaded Shoulder Pin into the medial hole of the Talar Trial. Place a second threaded Shoulder Pin into the lateral hole of the Talar Trial. In one embodiment, do not seat the medial shoulder pin until the lateral shoulder pin is placed.

Referring now to FIGS. 75-78, talar fin preparation may then be performed for a chamfer cut. The Chamfer-Cut Talar Fin Preparation includes retrieving the corresponding sized Talar Reaming Tower 1316. Attach the Reaming Tower 1316 to the anterior portion of the Talar Trial 1318, aligning the boss of the Reaming Tower 1316 with the hole in the Talar Trial 1318. Once aligned, rotate the set screw on the Reaming Tower 1316 in a clockwise manner to seat the Reaming Tower 1316 against the Talar Trial 1318. Retrieve the Talar Fin Reamer that mates with the Reaming Tower 1316. Use the Fin Reamer to punch superiorly and punch inferiorly. Translate the Fin Reamer between the superior and inferior holes while maintaining the undersurface of the Fin Reamer flush to the Reaming Tower until the Fin Reamer is completely seated across the length of the Reaming Tower. Remove the Reaming Tower by rotating the set screw counterclockwise to release from the Talar Trial. Once completed, remove the Shoulder Pins from the Talar Trial as well.

Figure 79:
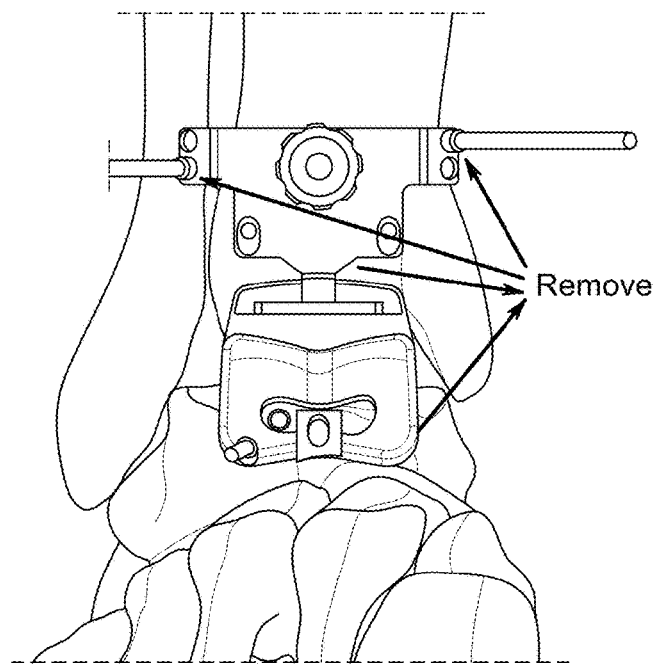
Figure 80:
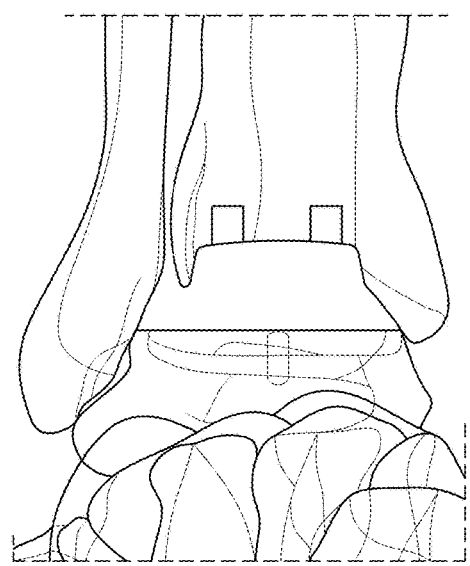

Then, the method may include removal of the trial construct, as shown in FIGS. 79-80. Trial Construct Removal includes removing the poly trial using the poly handling tool. Remove the talar trial using the talar handling tool. Remove the shoulder pins on the tibial trial. Remove the tibial trial pulling the tibial trial anteriorly. Remove the two smooth 2.4 mm Steinmann pins from the anterior tibia using the pin puller, if necessary. Now you're prepared for tibial and talar implant placement.

Figure 81:
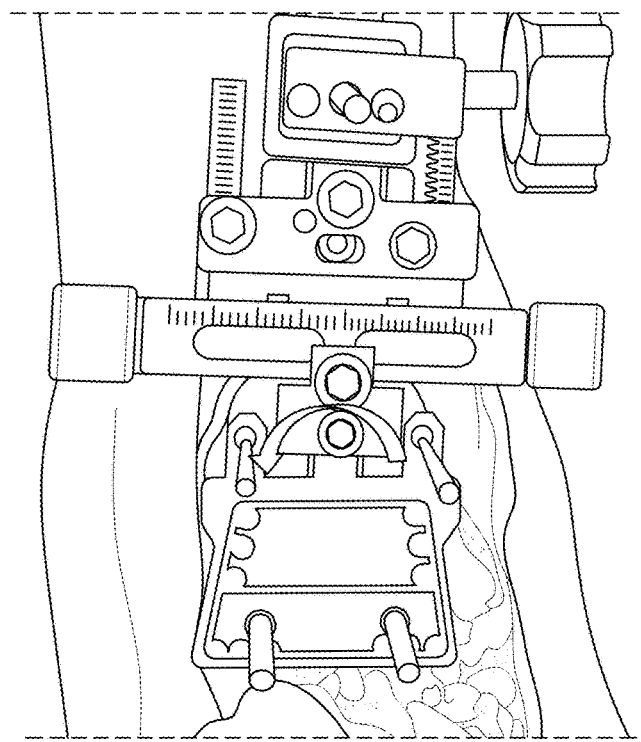
Figure 82:
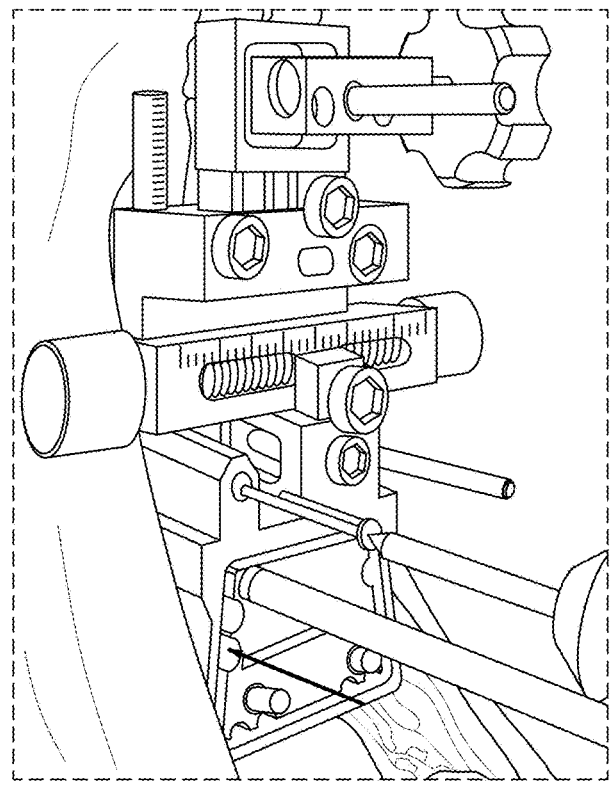

Referring now to FIGS. 81-97, an alternative method of tibial joint preparation is shown for a flat cut. The method includes tibial bone preparation, as shown in FIGS. 81 and 82. With reference to FIG. 81, FLAT-Cut Tibial Bone Preparation is shown. Once fine positioning has been confirmed and locked, remove the Sizing Resection Block by rotating the "OPEN" screw counterclockwise fully and pulling the sizing resection block anteriorly. Retrieve the Tibial FLAT Cut Resection Block slide the distal portion of the block over the two previously trimmed M/L 2.4 mm Smooth Steinmann Pins and into the dovetailed connection on the Alignment Construct and tighten the "OPEN" screw clockwise to lock the flat tibia cutting block in. Optionally, place two 2.4 mm Steinmann Pins into distal talar Resection Block holes while compressing the tibiotalar joint space, prior to tibial drilling. FIG. 82 shows the FLAT-Cut Tibial Bone Preparation including retrieving a Tibia Resection Drill. Using the Resection Drill, drill the medial and lateral holes in the Tibia Flat Resection Block utilizing the 3.5 mm Top Hat to secure position after the first hole has been drilled.

Figure 83:
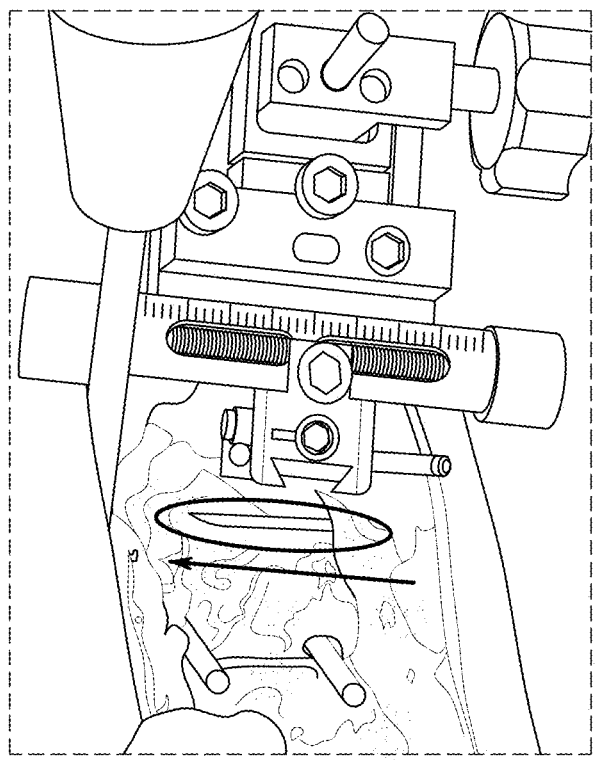

FIG. 83 shows the FLAT-Cut Tibial Bone Resection with a Proximal Cut. Retrieve the provided 13×90 mm Oscillating Saw Blade. Perform the flat cut across the top of the FLAT Cut Resection Block starting medially and working laterally.

Figure 84:
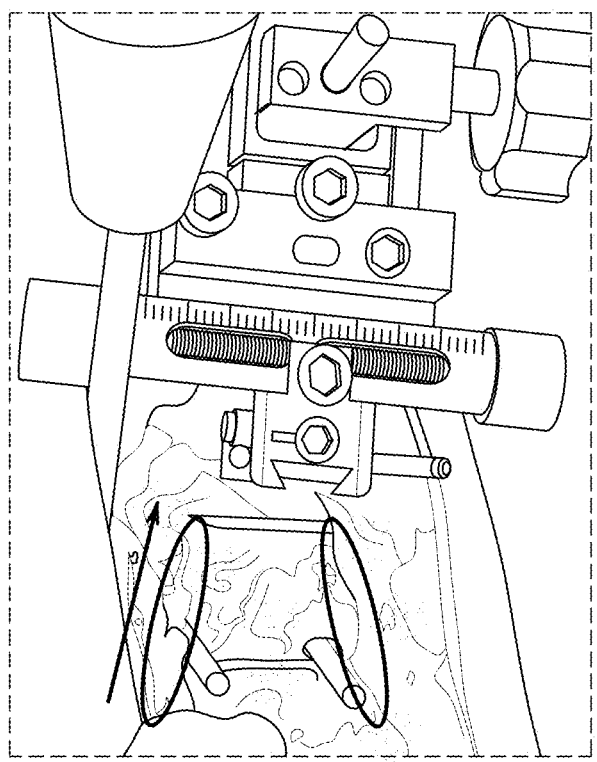

FIG. 84 shows the FLAT-Cut Tibial Bone Resection with Medial/Lateral Cuts. Using either the provided Oscillating Saw Blade or 8×50 mm Reciprocating Saw Blade, cut through the medial and lateral slots on the FLAT Cut Resection Block starting distally and walking the saw blade up proximally.

Figure 85:
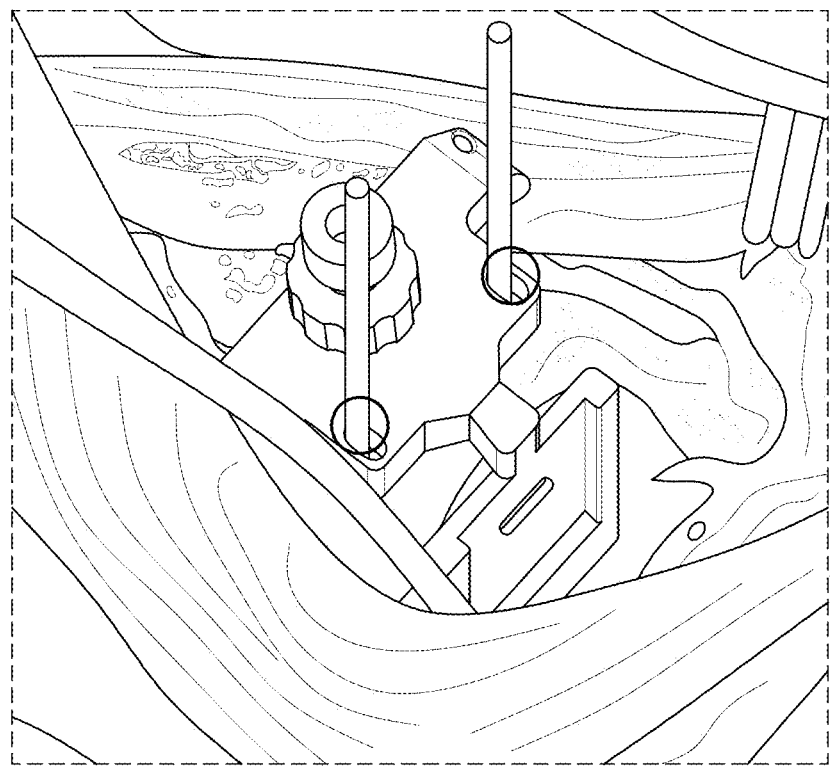

FIG. 85 shows Provisional Tibial Trial Positioning. Retrieve the Tibial Trial size corresponding to the Sizing Resection Block. By hand, slide the Tibial Trial over the two medial/lateral 2.4 mm Smooth Steinmann Pins on the anterior aspect of the distal tibia and insert such that the anterior surface of the Tibial Trial is approximately flush to the anterior tibia. Center the pins in the slots to ensure appropriate varus/valgus and superior/inferior placement against the inferior surface of the tibia. Using the 4-Bar Distractor, distract the tibiotalar joint and confirm provisional tibial trial position using AP and lateral fluoroscopy.

Figure 86:
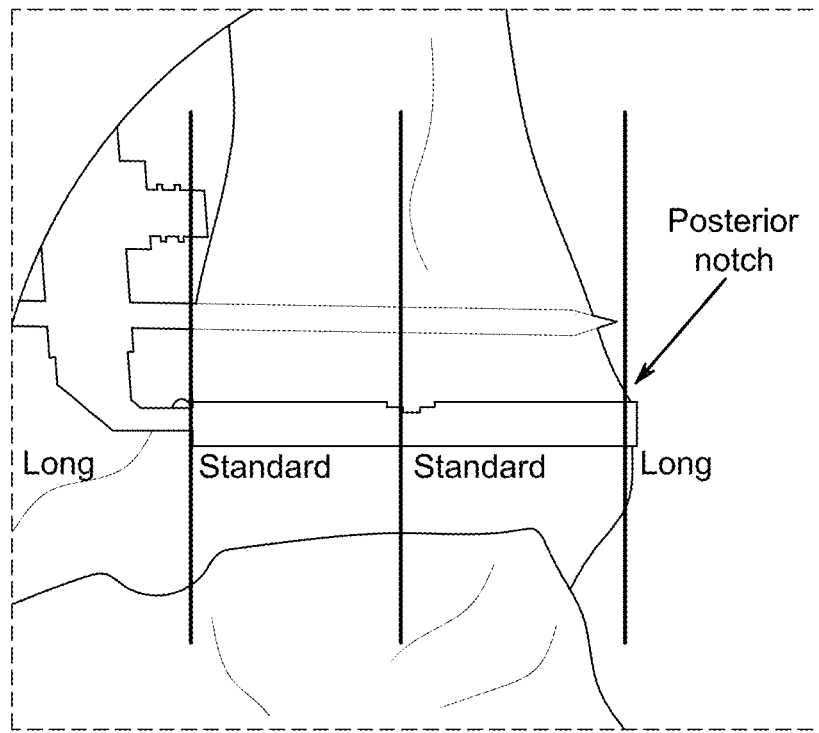
Figure 87:
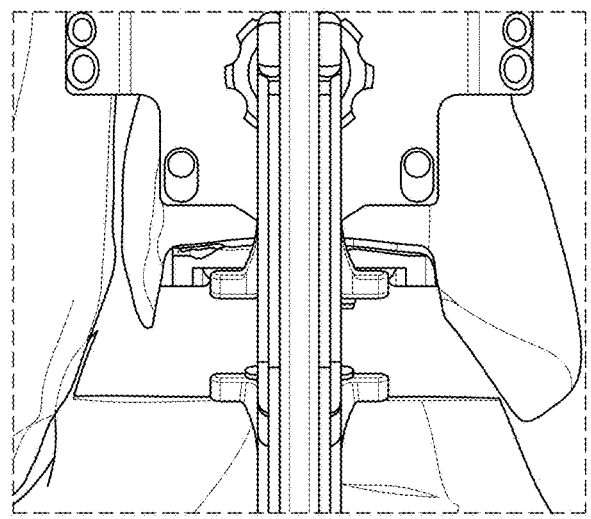
Figure 88:
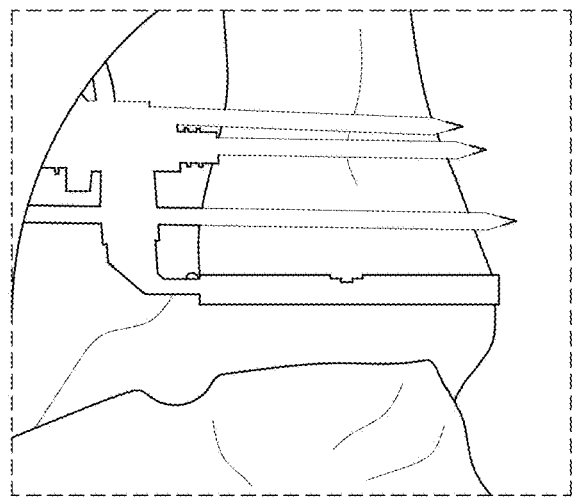
Figure 89:
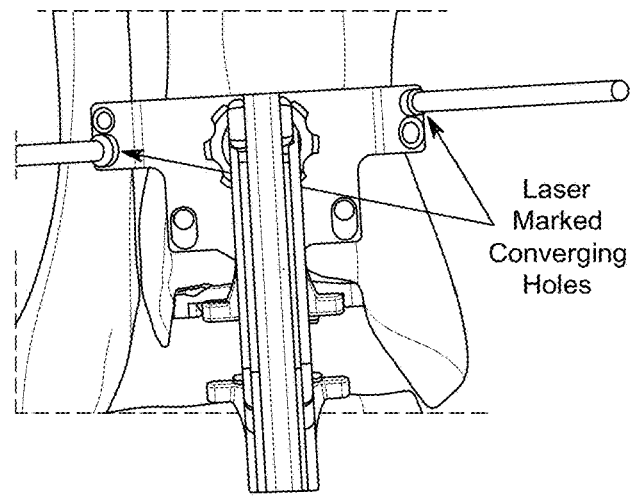

FIG. 86 shows Tibial Trial Sizing Evaluation. Tighten the Tibial Trial against the anterior tibia by rotating the locking nut on the Trial clockwise until the trial and anterior tibia are flush. Using a lateral fluoroscopy view, determine tibia implant length. Ensure that the notch of the tibial trial comes into view on the lateral view. If the notch is located beyond the posterior tibia, a regular tibia size should be used. If the notch is located within the tibia, a long tibia size should be used, per surgeon preference. The center of the tibial trial posterior notch should be aligned with the posterior tibia wall. It is recommended to use a long tibia size if uncertain whether the notch of the tibia trial is located within the tibia or not. Full anterior/posterior coverage with minimal overhang is preferred. FIG. 87 illustrates that once sizing has been evaluated, retrieve the 4-Bar Parallel Distractor and attach the modular Tibial Trial Paddles. Insert the 4-Bar Distractor into the resected tibiotalar joint matching the superior paddle's dovetail connection to the inferior aspect of the Trial's. Distract the joint by squeezing down on the 4-Bar distractor's handle to apply even pressure against the Tibial Trial and the talar cortical surface fully seating the tibial trial into position. FIG. 88 shows re-checking Tibial Trial position on AP and lateral fluoroscopy views to ensure position and fit. FIG. 89 illustrates that with the 4-Bar Distractor in place, inserting two 2.4×50 mm Threaded Shoulder Pins into two of the 4 proximal converging pin holes, ensuring that either both laser marked holes are used together, or two non-laser marked holes are used together.

Figure 90:
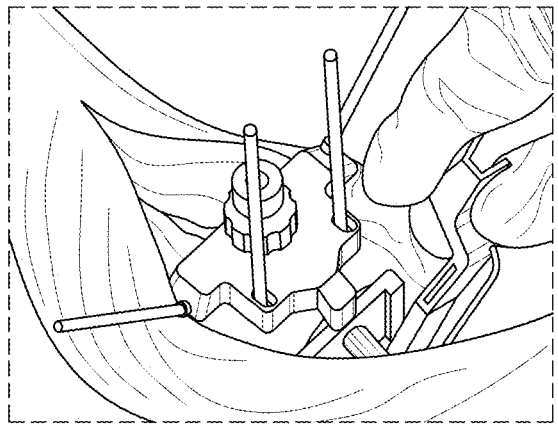
Figure 91:
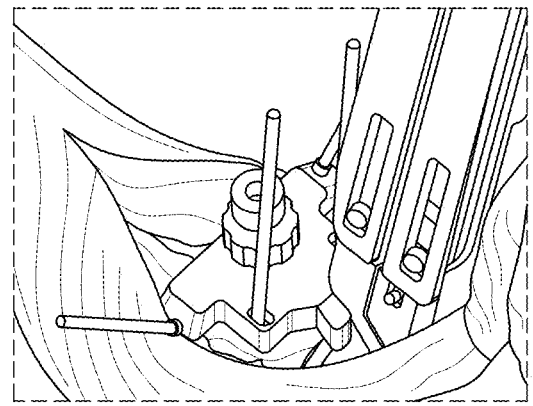
Figure 92:
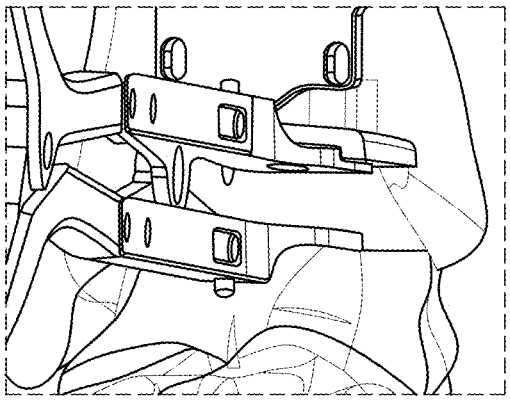
Figure 93:
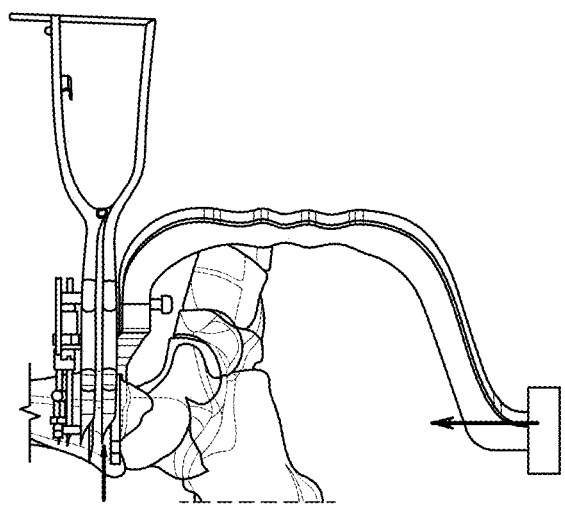

Referring now to FIGS. 90 and 91, the method includes a vertical tibial peg punch procedure. The peg punch procedure may include removing the 4-Bar Distractor from the tibiotalar joint after the converging shoulder pins have been put in place and inserting the Distractor Viper Tip Peg Punch Paddle into the joint by hand to assess placement against tibial trial peg holes. Then connect the 4-Bar Distractor to the corresponding Distractor Viper Tip Peg Punch Paddle corresponding to the selected Tibial Trial size. Retrieve the Tibia Impaction Tool and attach the (right or left) Tibia Impaction Dimpled Tool and have this modular tool construct available. As shown in FIGS. 92 and 93, the vertical tibial peg punch process may include inserting the 4-Bar Distractor into the resected tibiotalar joint, ensuring that the Viper Tip Peg Punch Paddle is facing superiorly. Align the pegs with the inferior holes in the Tibial Trial, verifying position using AP and lateral fluoroscopy as well as visually. Begin to distract the 4-Bar Distractor under lateral fluoroscopy. Using the previously assembled Tibia Impaction Tool construct, insert the Impaction Dimple underneath the Viper Tip Peg Punch Paddle. Impact the distal end of the Impaction Handle, still under 4-Bar distraction until the Peg Punch Paddle is fully seated.

Figure 94:
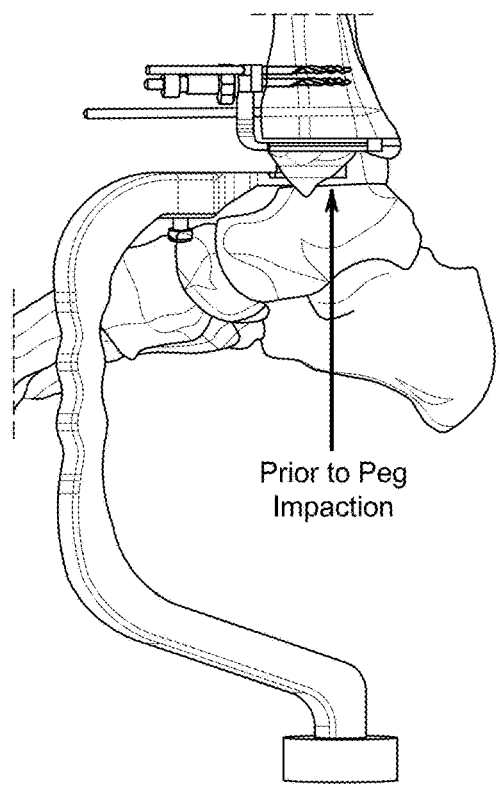
Figure 95:
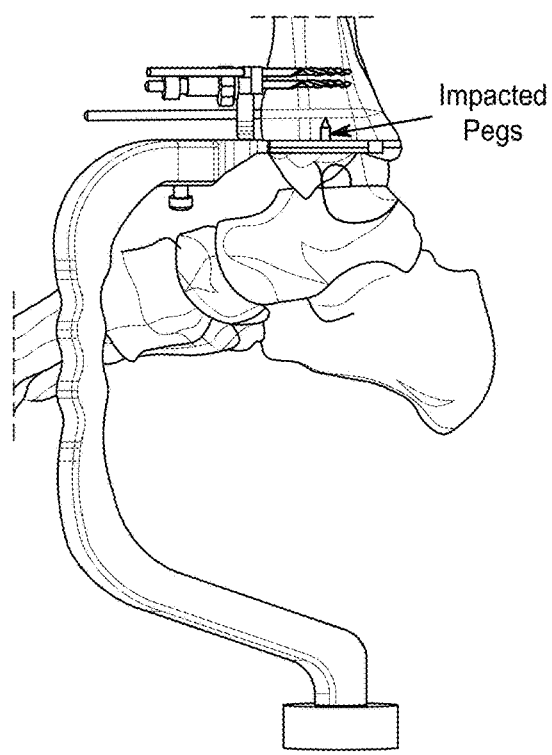

Referring now to FIGS. 94 and 95, an alternative vertical tibial peg punch procedure is shown. The procedure may include, as shown in FIG. 94, Vertical Tibial Peg Preparation using an Impaction Handle+Now that the converging shoulder pins have been put in place, remove the 4-Bar Distractor from the tibiotalar joint. Retrieve the (right or left) modular Impaction Peg Punch corresponding to the size of the Tibial Trial. Prior to attaching, orient the Impaction Peg Punch such that the projections align with the holes on the inferior aspect of the Trial. Now attach the Impaction Handle Tool to the Impaction Peg Punch. Both visually and under fluoroscopy, ensure that the Impaction Peg Punch is perpendicular to the long axis of the tibia verifying position using AP and lateral view. FIG. 95 shows under fluoroscopy, use of a mallet on the distal end of the Impaction Handle construct to impact the pegs into the tibia. Confirm that complete seating of the pegs has occurred relative to the Trial by direct visualization under fluoroscopy. Care should be taken, over impaction of the Peg Punch should be avoided if possible. Two to four moderate strikes on the distal end of the impaction handle construct with counter pressure on the limb should be sufficient.

Figure 96:
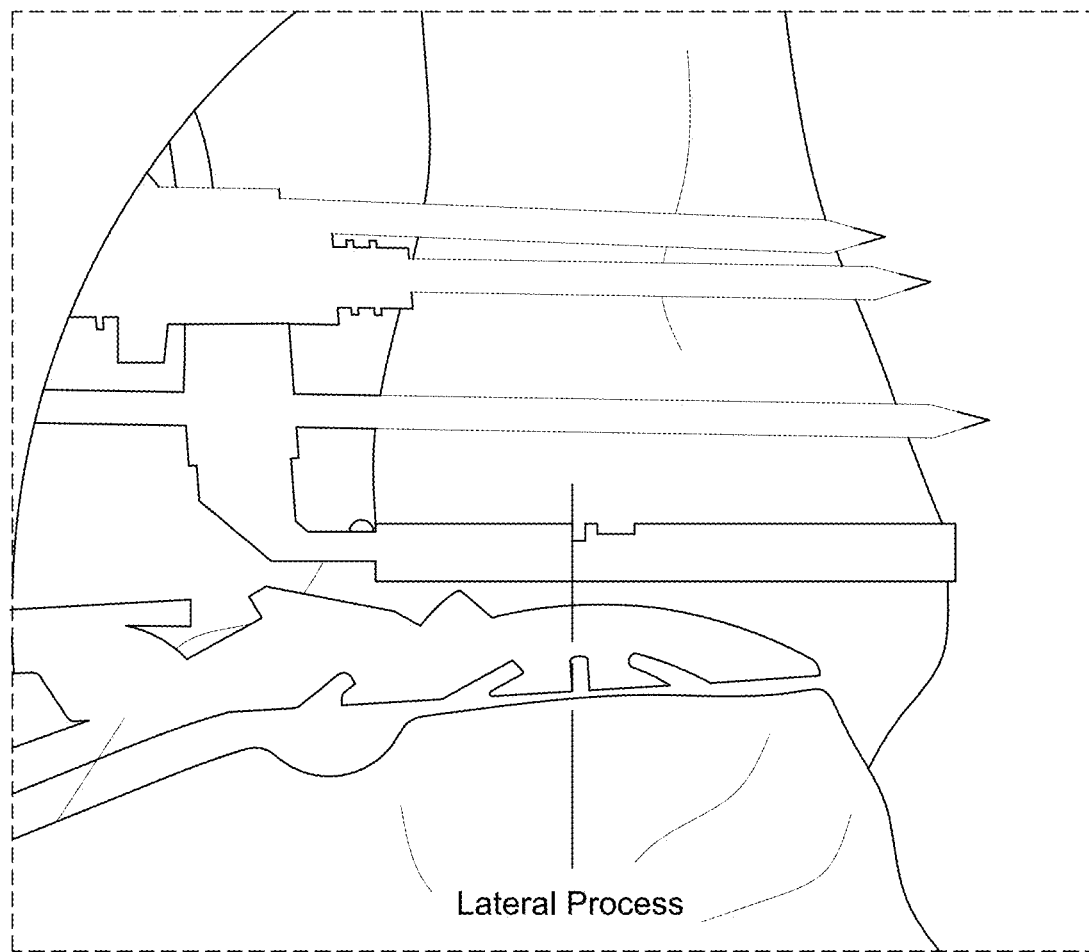
Figure 97:
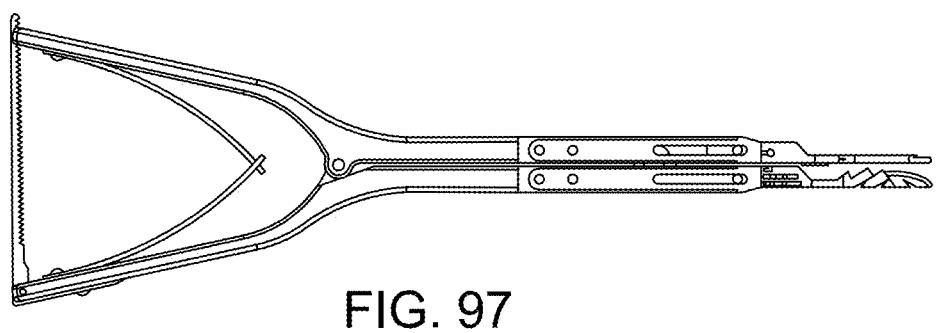
Figure 98:
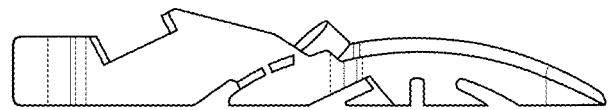

Referring now to FIGS. 96-98, the method may also include a talar trial positioning procedure. FIG. 96 shows Chamfer-Cut Talar Trial Positioning. Retrieve the anticipated 4-Bar Talar Trial Lollipop Sizing Resection Guide option. By hand, initially place the modular Resection Guide into the joint to evaluate coverage. Visually and under fluoroscopy, confirm the Resection Guide size by assessing coverage on talus, ensuring that the Resection Guide adequately covers the medial and lateral aspect of the dorsal table top cut without impinging on the gutters and vertical line on Resection Guide aligns with the lateral process. Once sizing has been evaluated, retrieve the 4-Bar Distractor and attach the selected modular Sizing Resection Guide. Re-insert the Resection Guide into the tibiotalar joint, matching the superior paddle's dovetail connection to the inferior aspect of the Tibial Trial and the inferior aspect of the Talar Trial Sizing Resection Guide to the resected talar bone surface. FIGS. 97 and 98 show distracting the joint by squeezing down on the 4-Bar Distractor Handle, applying even pressure against the Tibial/Talar Trial Guides and the tibiotalar cortical surfaces preparing to fully seat the Talar Trial Resection Guide into position. With the 4-Bar Distractor in place, re-check the Talar Sizing Resection Guide position under a lateral fluoroscopy view to ensure position and fit before setting into place with shoulder pins. The selected Talar Trial Guide can be sized up by 1 or down by 2 to achieve appropriate coverage. Plantarflexing the tibiotalar joint to achieve appropriate visualization before setting in place is recommended. After this alternative vertical tibial peg punch procedure is completed, the method may proceed through the steps discussed in greater detail above with reference to FIGS. 65-80.

Figure 99:
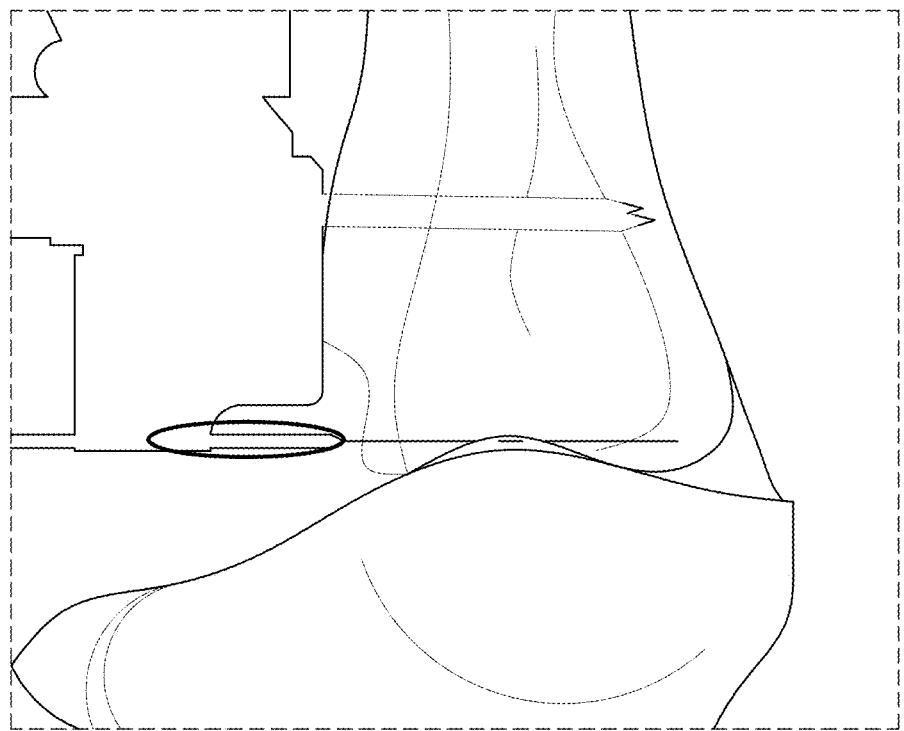
Figure 100:
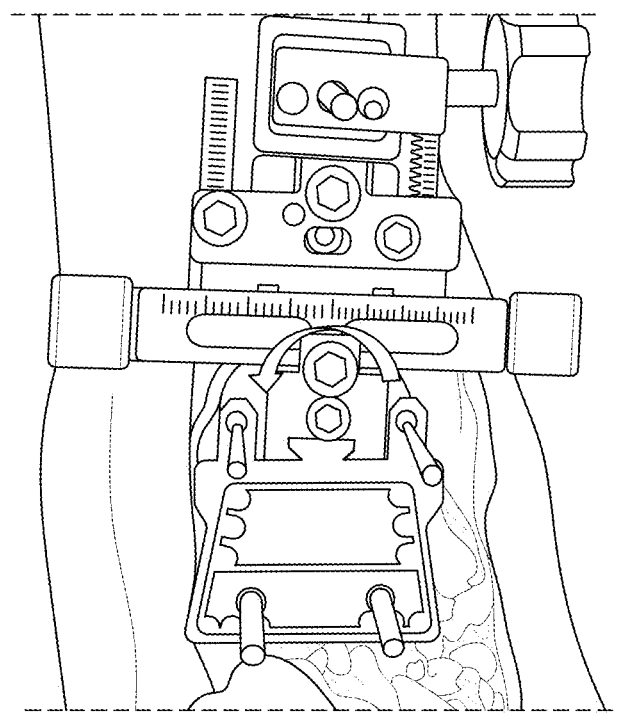

Referring now to FIGS. 99-116, an alternative flat cut talar preparation is shown. FIG. 99 shows a Talar Bone Resection with a Dorsal Cut. Cut the 2.4 mm Steinmann talar pins flush to the Resection Block to allow for clearance of the saw blade. Optionally, place gutter pins around the talar cut guide prior to completing bone resection. Retrieve the provided 8×90 mm Oscillating Saw Blade to make the talar dorsal cut. Cut the superior aspect of the talus through the distal cutting slot, taking care to avoid contact of the saw with the medial malleolus and the fibula, then verify accuracy under a lateral fluoroscopy view. FIG. 100 shows Resection Block Removal. Remove the Resection Block by rotating the "OPEN" screw counterclockwise and pulling the Resection Block off anteriorly. Remove provisional Talar Pins with provided Pin Puller. Once initial cuts have been completed using the Resection Block as a guide, remove the Block and complete any necessary or remaining free hand cuts, taking care to not cut past the existing cortical boundaries. Use of an osteotome or rongeurs is recommended to remove bone fragments.

Figure 101:
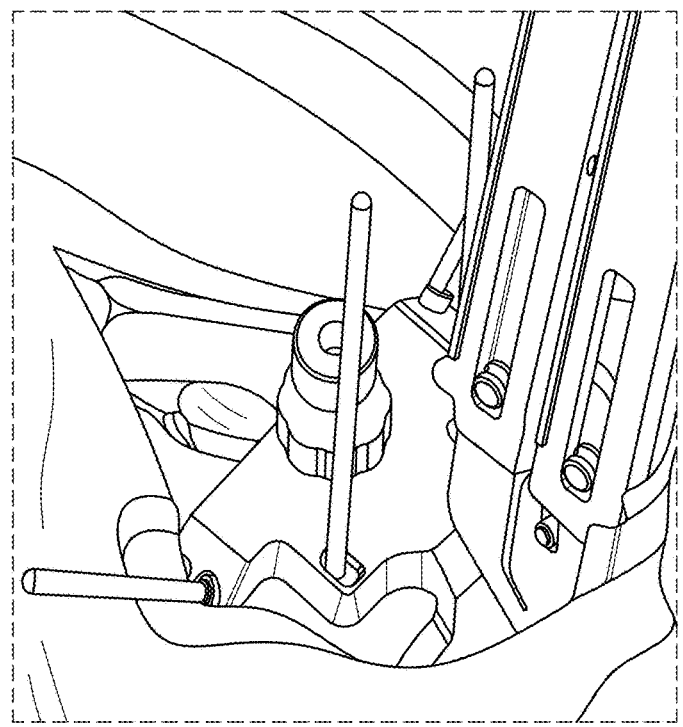

FIG. 101 shows Talar Trial Provisional Placement with a FLAT-Cut. Retrieve the anticipated 4-Bar FLAT Cut Talar Trial size. By hand, initially place the modular Trial into the joint to evaluate coverage. Visually and under fluoroscopy confirm the Trial size by assessing coverage on talus, ensuring that the trial adequately covers the medial and lateral aspect of the dorsal cut without impinging on the gutters and the vertical line on trial aligns with the lateral process. Ensure that appropriate anterior to posterior coverage is achieved using lateral fluoroscopy as well. Once initial sizing has been evaluated, retrieve the 4-Bar Parallel Distractor and attach the selected modular Talar Trial.

Figure 102:
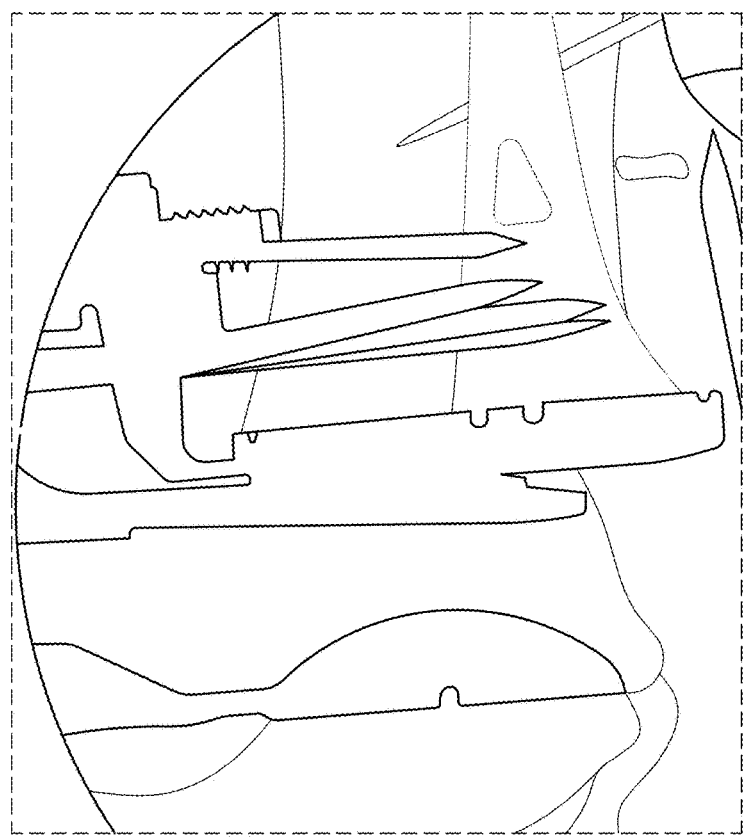

FIG. 102 shows Talar and Poly Trial Provisional Placement with a FLAT-Cut. With the Talar Trial attached to the 4-Bar Distractor, re-insert the trial into the resected tibiotalar joint, matching the superior paddle's dovetail connection to the inferior aspect of the Tibial Trial and the inferior aspect of the Talar Trial to the resected talar bone surface. Distract the joint by squeezing down on the 4-Bar Distractor Handle, applying even pressure against the Tibial/Talar Trials and the cortical surfaces. Then retrieve and insert the estimated Poly Trial size by hand into the tibiotalar joint. Using an AP and lateral fluoroscopy view, evaluate the Tibia/Poly/Talar Trial size relationship and anatomic placement of the selected Trials. Ensure that the fluoroscopic notch, located on the distal aspect of the Talar Trial is visible on lateral fluoroscopy to ensure that a perfect lateral is taken when verifying appropriate Talar Trial position.

Figure 103:
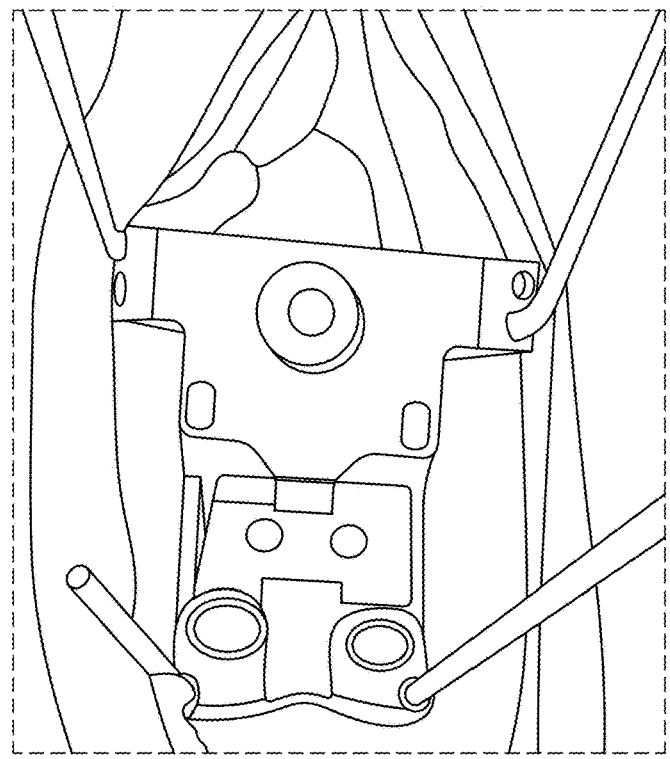

FIG. 103 shows Secure Talar Trial Placement with a FLAT-Cut. With the 4-Bar distracted and selected Poly Trial in place, secure the FLAT Talar Trial position by placing two 2.4×25 mm Threaded Shoulder Pin into the anterior most medial/lateral holes of the Trial until securely seated against the talar cortical surface. Put the tibiotalar joint through a gentle range of motion evaluation to ensure adequate placement and correct Poly Trial thickness, then re-check the talar trial position under a lateral fluoroscopic view to ensure appropriate position.

Figure 104:
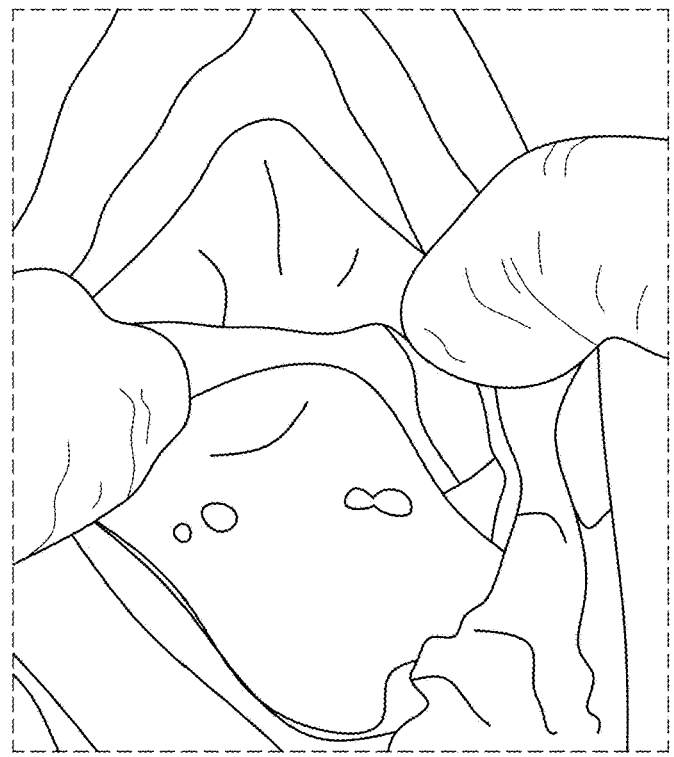
Figure 105:
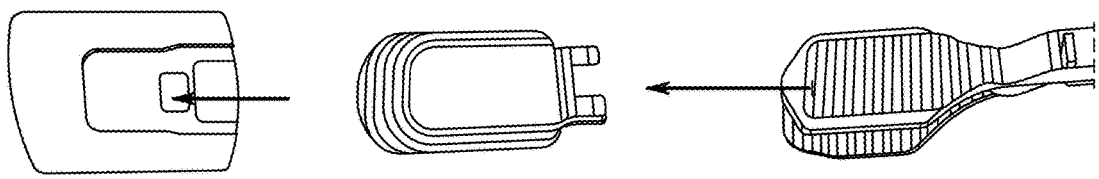
Figure 106:
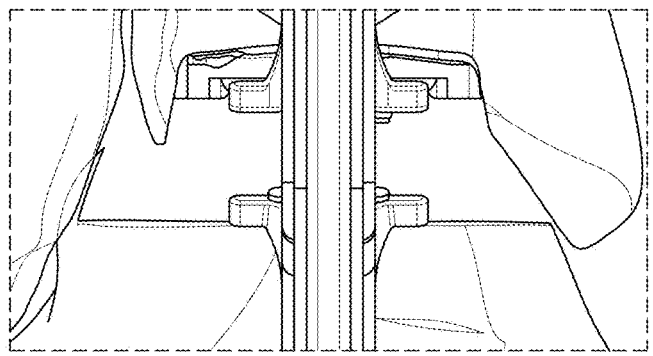
Figure 107:
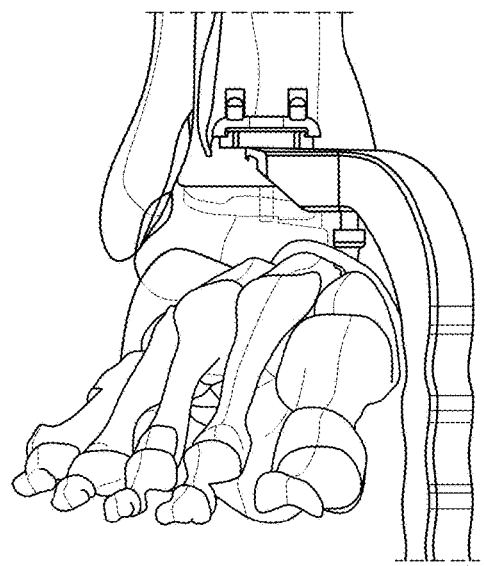
Figure 108:
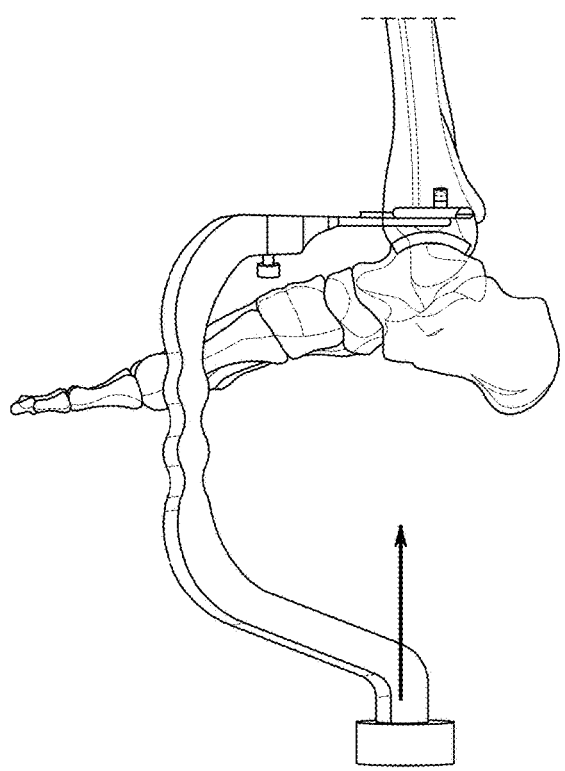
Figure 109:
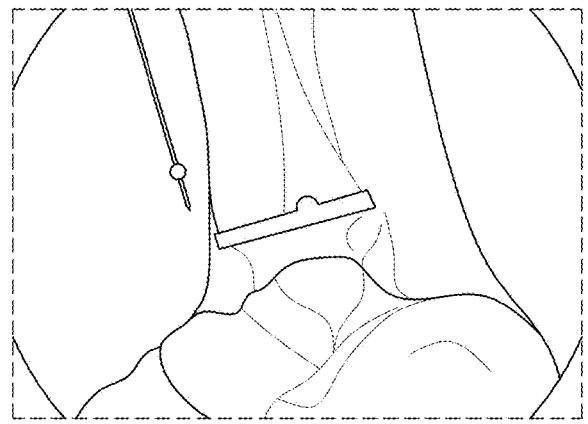
Figure 110:
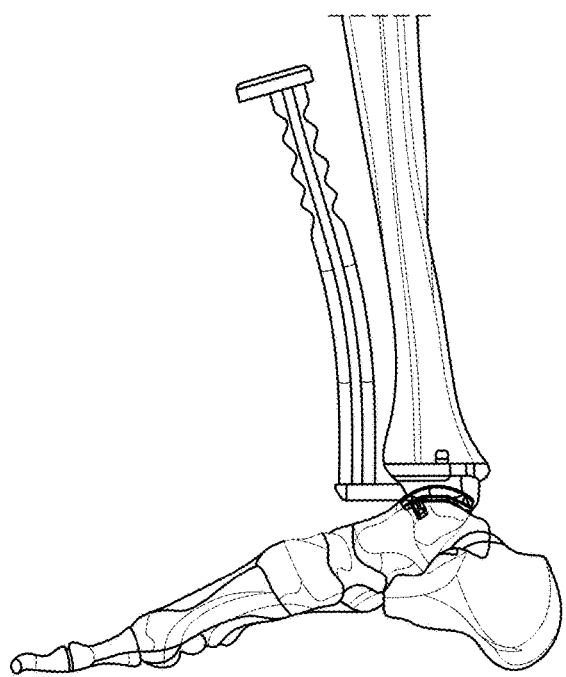
Figure 111:
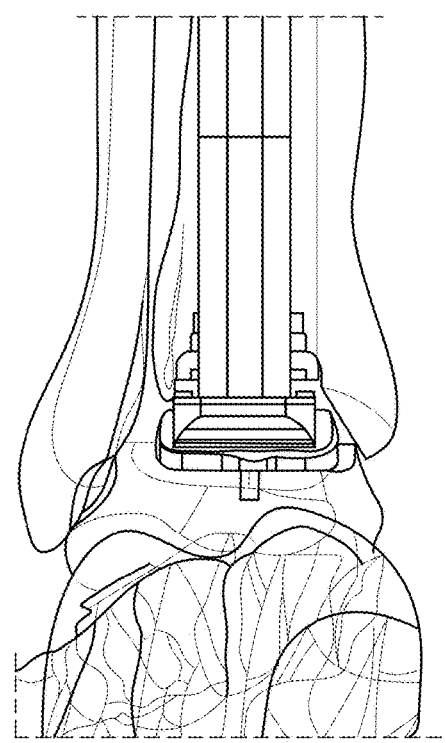
Figure 112:
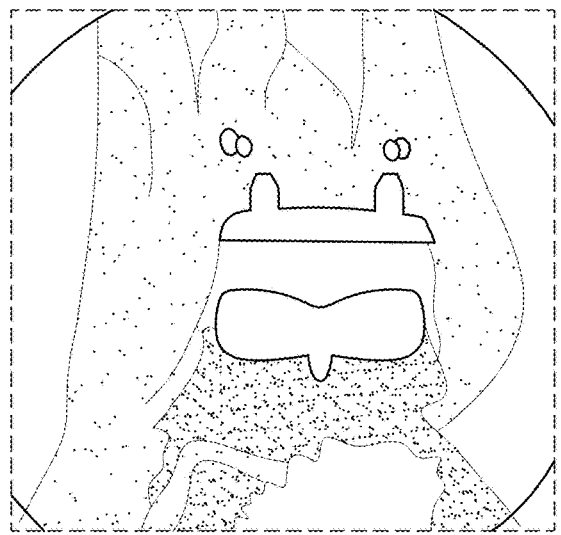
Figure 113:
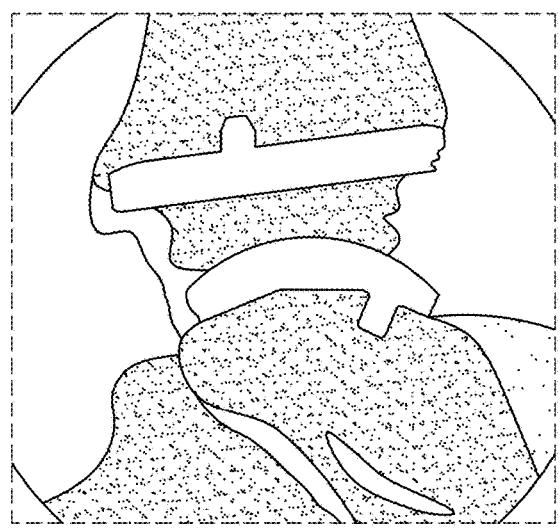

FIG. 104 shows Talar Peg Drill Holes and Bone Preparation with a FLAT-Cut. Place the tibiotalar joint in plantarflexion to gain access to the drill hole guides on the anterior face of the FLAT Talar Trial. Retrieve the Talar Peg Drill. Under power, drill the medial and lateral Talar Trial peg holes until the drill shoulder bottoms out on the proximal surface of the Talar Trial. Trial Removal includes removing the Poly Trial using the Poly Handling Tool. Remove the two Shoulder Pins from the anterior Tibial Trial using the provided Pin Puller. Then remove the Tibial Trial by pulling anteriorly, if necessary, re-examine joint.

The method may also include a final tibia implant placement procedure, as shown in FIGS. 105-109. Final Tibial Implant Placement (Similar for ARC or FLAT tibial components) includes selecting the appropriate tibia implant style and size. (1) Retrieve the appropriately sized Tibia Impaction Protector and attach to the tibia implant by sliding the Impaction Protector into the dovetail connection of the implant. Apply bone cement to the superior surface of the tibia implant. Do not apply bone cement to the vertical pegs. (2a) Attach the tibia implant/tibia Impaction Protector to the 4-bar distractor and guide insertion such that the tibial pegs align with the punched holes, then distracting the 4-bar with two finger strength. (2b) Retrieve the Centering Tibia Impaction Coin or Dimple and attach to Tibia Impaction Handle or 4-Bar Distractor. Place the Centering Impaction Coin into the tibiotalar joint while ensuring that the boss on the centering impaction tool fits within the recess on the Tibia Impaction Protector. (3) Use a mallet to strike the distal end of the Tibia Impactor to fully seat the tibial implant using lateral fluoroscopy to verify process.

The method may further include a final talar implant placement, as shown in FIGS. 110-113. Final Talar Implant Placement (Similar for Chamfer or Flat tibial components) includes retrieving the appropriate talar implant style and size. Apply bone cement to the inferior surfaces of the talar implant. Do not apply bone cement to the fin or vertical pegs. Insert the talar implant into the tibiotalar joint and align it over the chamfered (or flat) cut until the fin (or pegs) fits into the reamed slot(s). Confirm placement on lateral fluoroscopy view to ensure that the fin (or pegs) is/are seated within the talus. Retrieve the Talus Impactor. Press the Talus Impactor against the talar implant. Use a mallet to impact the talus implant against the talus. Confirm talar implant placement using fluoroscopy. For the flat talus, align the flat talar implant such that the pegs fit within the drilled peg holes on the talus. During talus impaction, ensure the foot is in plantarflexion.

Figure 114:
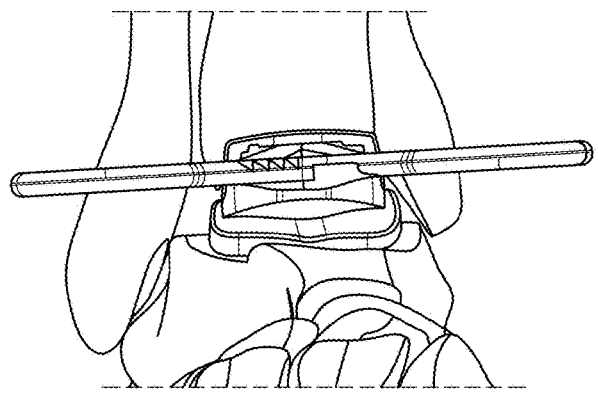
Figure 115:
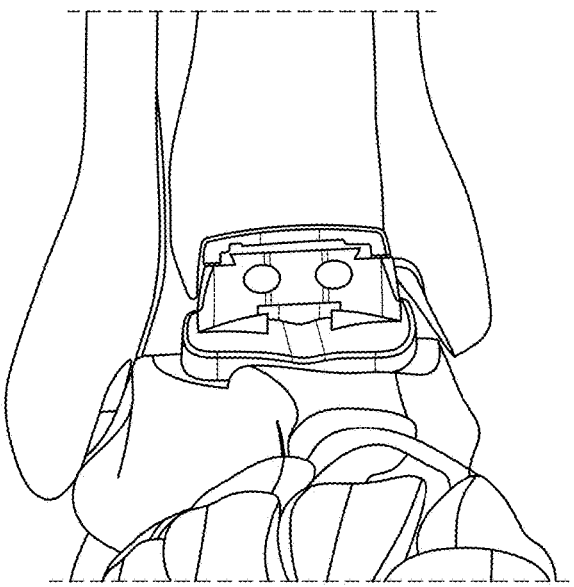
Figure 116:
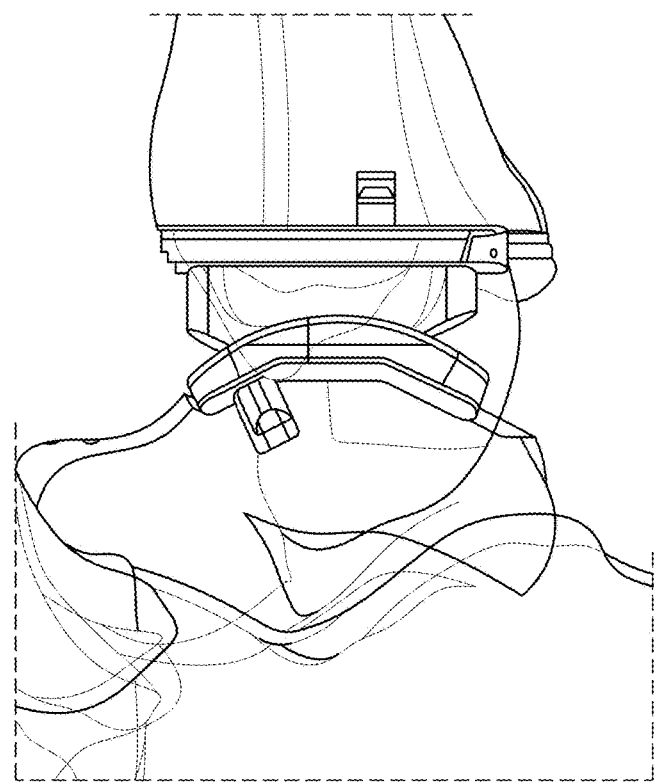
Figure 117:
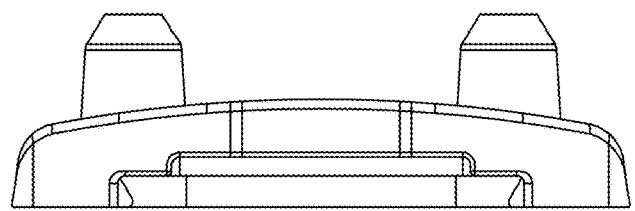
Figure 118:
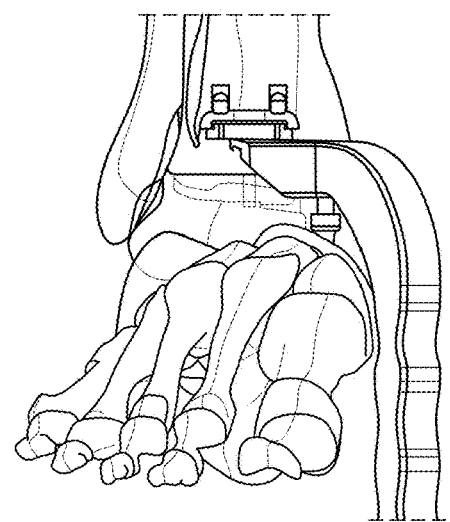
Figure 119:
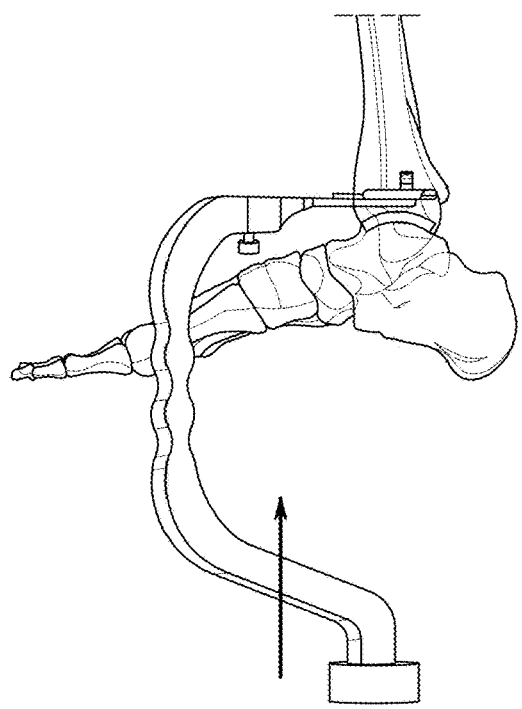
Figure 120:
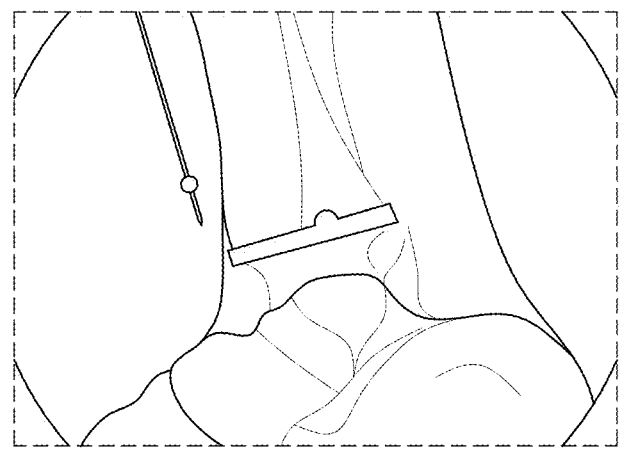
Figures 121, 122:
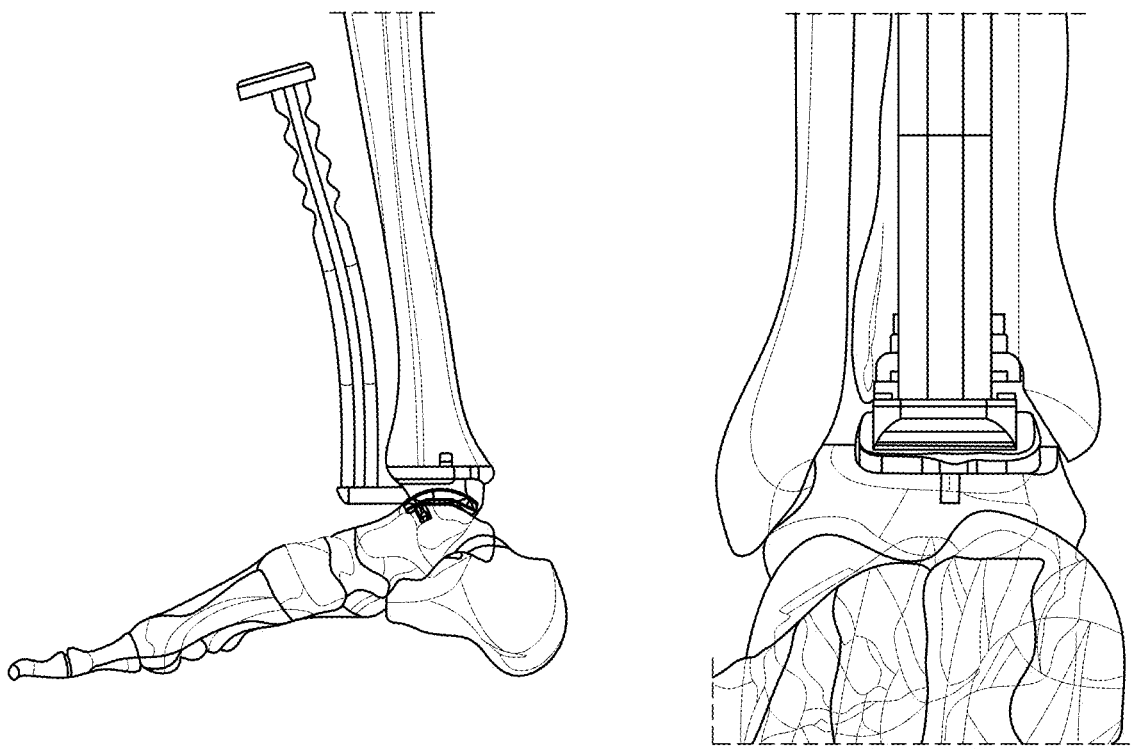
Figure 123:
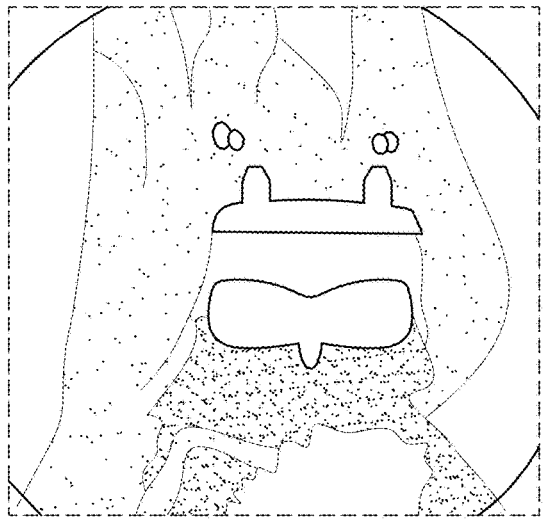
Figure 124:
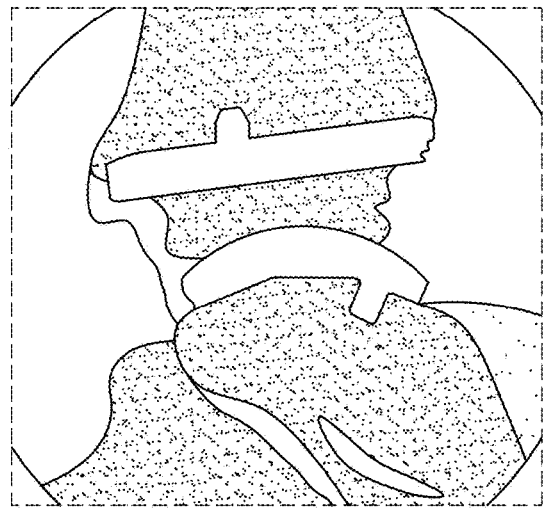

In addition, the method may include a final poly implant placement procedure, as shown in FIGS. 114-116. Final Poly Implant Placement includes retrieving the correct poly implant size. Attach the poly implant to the Poly Placement Handle. Insert the poly implant between the tibia and talus such that the poly mates with the dovetail connection on the tibia implant until a click is heard or felt between the poly and tibia implant. Remove the Poly Placement Handle. Closure includes proceeding to final fluoroscopic images and incision closure at this time.

Next, the method may include a final implant placement procedure, as shown in FIGS. 117-127. FIGS. 117-120 show the final tibial implant placement procedure, which may be used for both ARC and FLAT tibial components. Select the appropriate tibia implant. Retrieve the appropriately sized Tibia Impaction Protector and attach to the tibia implant by sliding the Impaction Protector into the dovetail of the implant. Apply bone cement to the superior surface of the tibia implant. Do not apply bone cement to the pegs. Insert the tibia implant/tibia Impaction Protector by gripping the anterior handle of the Tibia Impaction Protector and guiding insertion by handle. Retrieve the Centering Tibia Impaction Coin and attach to Tibia Impaction Handle. Place the Centering Impaction Coin into the tibiotalar joint while ensuring that the boss on the centering impaction tool fits within the recess on the Tibia Impaction Protector. Use a mallet against the Tibia Impactor to seat the tibial implant under lateral fluoroscopy.

Referring to FIGS. 121-124, the final talar implant placement procedure is shown. Retrieve the appropriately sized talar implant. Apply bone cement to the inferior surfaces of the talar implant. Do not apply bone cement to the fin. Insert the talar implant into the tibiotalar joint and align it over the chamfered cut until the fin fits into the reamed slot. Confirm placement on lateral fluoroscopy view to ensure that the fin is within the talus. Retrieve the Talus Impactor. Press the Talus Impactor against the talar implant. Use a mallet to impact the talus implant against the talus. Confirm talar implant placement using fluoroscopy. In one embodiment, for the flat talus, align the flat talar implant such that the pegs fit within the drilled peg holes on the talus. During talus impaction, ensure the foot is in plantarflexion.

Figure 125:
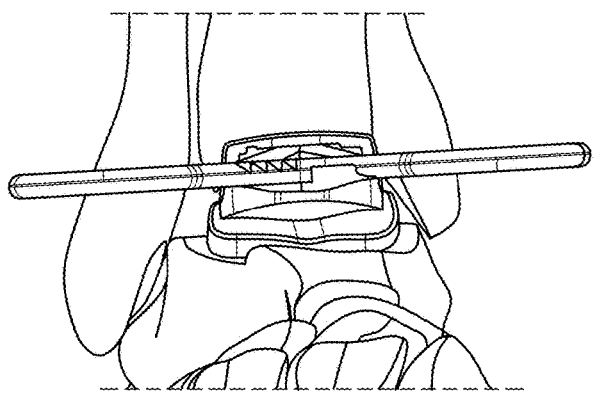
Figure 126:
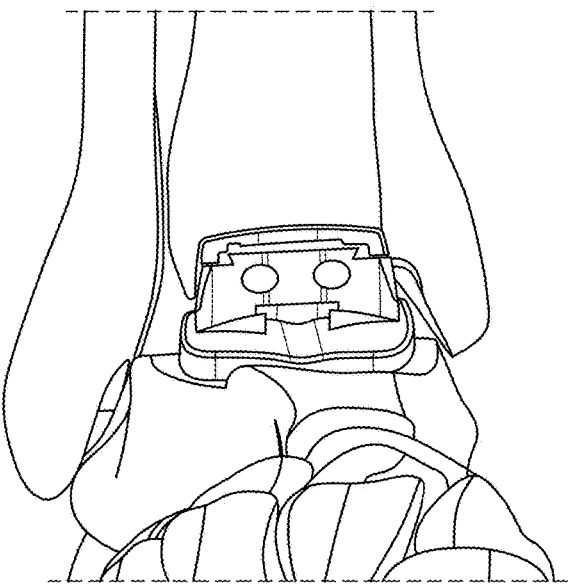
Figure 127:
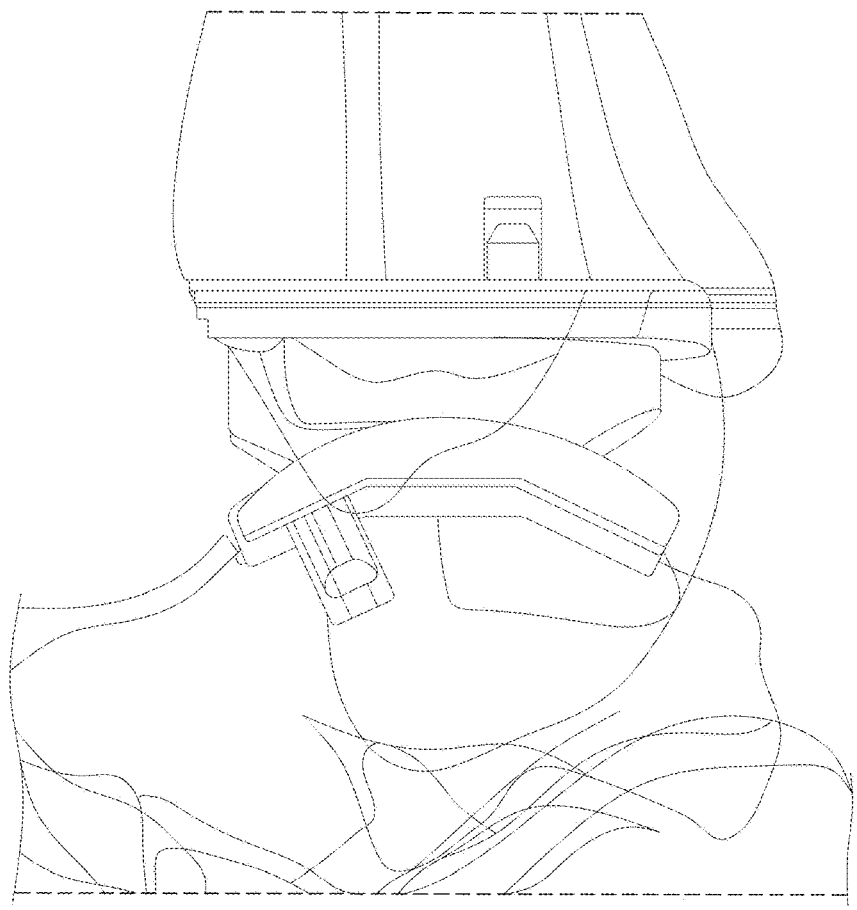

The final implant placement procedure may also include a final poly implant placement procedure, as shown in FIGS. 125-127. Final Poly Implant Placement includes retrieving the correct sized poly implant. Attach the poly implant to the Poly Placement Handle. Insert the poly implant between the tibia and talus such that the poly mates with the dovetail on the tibia trial until a click is heard or felt between the poly and tibia implant. Remove the Poly Placement Handle. Closure includes proceeding to final fluoroscopic images and incision closure at this time.

Figure 128:
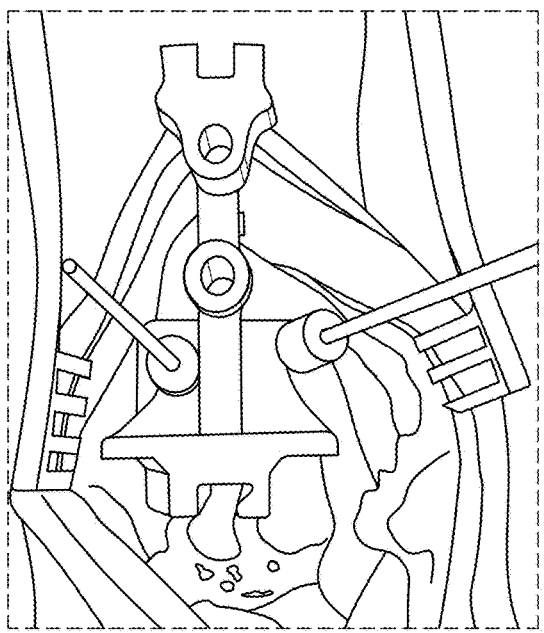

The method may also be performed using a patient specific alignment guide, as shown in FIGS. 128-132. FIG. 128 illustrates Provisional Fixation. Once the distal tibiotalar joint has been exposed and pre-operative planning CT scans have been examined to evaluate appropriate guide placement, now establish alignment position by matching the distal most contoured portion of PSI guide to the patient's anatomy, using Notch of Harty as an anatomic reference point. Using a pin driver, place two provisional 2.4 mm×100 mm smooth pins through the distal most medial/lateral converging pin holes, securing the PSI construct to the anterior cortex of the tibia.

Figure 129:
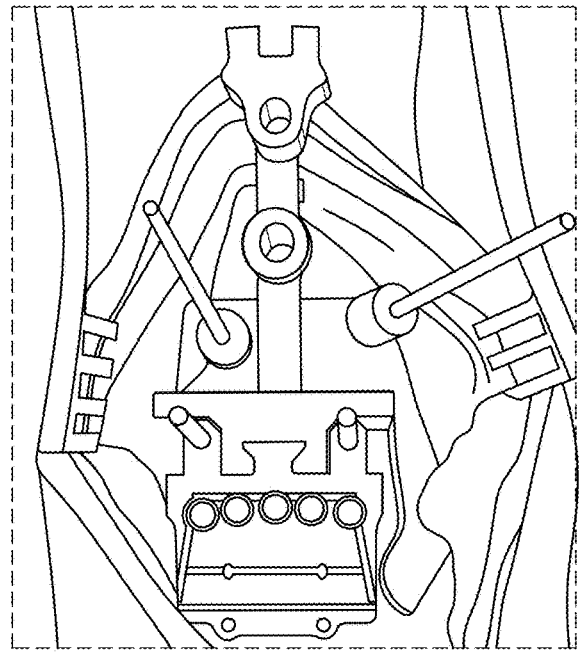

FIGS. 129 and 130 show Rotational and Translational Adjustments. Based on surgeon preference, retrieve either the ARC™ or FLAT sizing resection block for the anticipated tibial implant size. Insert the sizing resection block into the dovetailed portion of the PSI guide until a secure press-fit connection has been established. With the selected tibial sizing resection block attached, take an AP fluoroscopy shot to evaluate gross Joint Line Height and M/L positioning. To further assess and confirm Joint Line Height, insert the Angel Wing into the horizontal slot on the anterior face of the sizing resection block, then insert the JLR rod into the posterior lateral receiving end of the Angel Wing, rotating the distal portion of the JLR Rod until tightly fixed to the alignment construct. Then compare the long axis of the tibia with the joint line axis. Once positioning has been confirmed on AP and lateral fluoroscopy views, secure the sizing resection block with two M/L 2.4 mm×60 mm pins located at the distal most portion of the block, just below the PSI alignment guide, then cut pins flush with pin cutters. In one embodiment, Medial—Lateral alignment can be evaluated with an AP fluoroscopy view, slope can be evaluated with JLR Rod, varus—valgus can be determined with laser.

FIGS. 131 and 132 shows Gross Positioning with a Tibial Alignment Laser. Once the ARCHITECT™ PSI Alignment Construct is in place, retrieve the Tibial Alignment Laser and insert the distal self activating portion into the horizontal slot on the anterior face of the selected Tibial Sizing Resection Block, ensuring the laser window is pointed posteriorly, towards the operative limb. In one embodiment, to assess Internal/External (I/E) rotation, verify the green beam is targeting the tibial crest, roughly 10 cm distal from the tubercle. In one embodiment, using fluoroscopy, shoot an AP image that confirms positioning prior to setting the position with two 2.4×110 mm Smooth Steinmann Pins to determine appropriate position.

After positioning of the patient specific alignment guide, the method may then proceed to the procedures starting at FIGS. 39-48, for the Arc procedure, or FIGS. 49-53, for the flat procedure, and continue through the procedures described with reference to FIGS. 54-80, as described in greater detail above and which will not be described again here for brevity sake.

Figure 133:
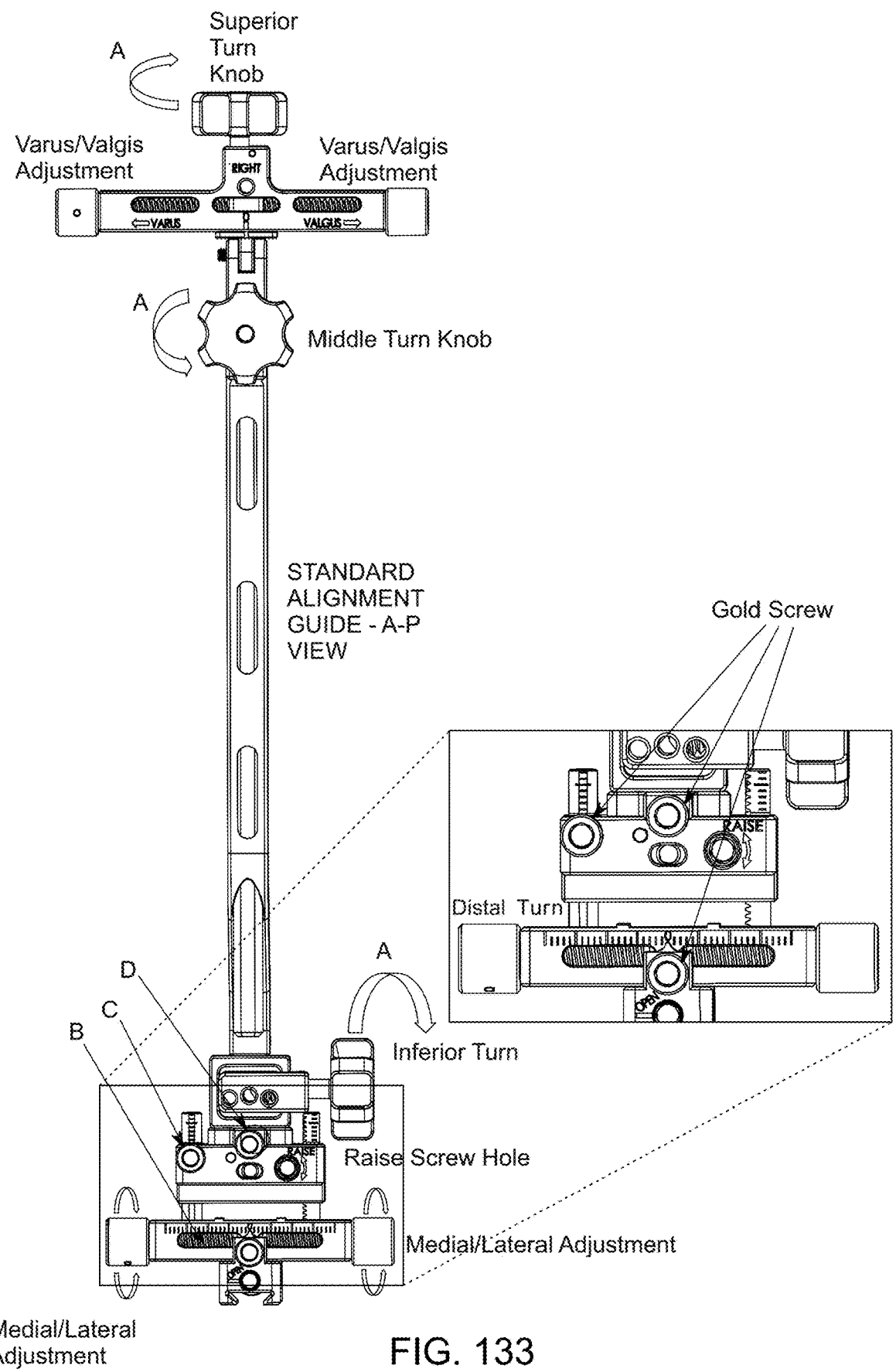
FIGS. 133-161 is a portion of the method of FIG. 24 using a full alignment guide, in accordance with an aspect of the present disclosure.

The method may also be performed using a full alignment guide, as shown in FIGS. 133-152. FIG. 133 shows retrieving the Standard External Alignment Guide. The Alignment Guide is prepared on the back table for placement by following steps A-D below. A) Varus/Valgus Controls—Rotate the posterior, middle and distal turn knobs counterclockwise by hand until fully open. B) Medial/Lateral Controls—Rotate the medial/lateral small turn knobs by hand, on either side of the construct to center the distal receiving dovetailed connection to 0. Then lock the position by rotating the distal most screw clockwise with the hex driver. C) Proximal/Distal Controls—With the alignment guide in hand and using the hex driver, rotate the "RAISE" screw clockwise (to raise) or counterclockwise (to lower) until the proximal aspect of the control block is flush with the laser marked lines on the two vertical tracks. Lock the position by rotating the screw on the far left of the alignment guide clockwise until fully tightened. D) Internal/External Controls—To adjust internal/external rotation, insert the hex driver into the proximal most central screw and unlock by turning counterclockwise, allowing for rotational adjustments, then re-lock position by rotating the screw clockwise with the hex driver.

Incision and approach include making a longitudinal midline incision over the anterior ankle, beginning approximately 10 cm proximal to the ankle joint and terminating just distal to the talonavicular joint. The incision will start approximately 1 cm lateral to the tibial crest and will course just lateral to the tibialis anterior tendon. The initial incision should penetrate skin only, but no direct tension should be placed on the skin margins until full-thickness retraction is possible. Identify the superficial peroneal nerve and retract it laterally. Continue exposure to the extensor retinaculum. Identify the extensor hallucis longus (EHL) tendon below the retinaculum and divide the retinaculum longitudinally over the EHL tendon. Care should be taken to leave the sheath of the tibialis anterior (TA) tendon intact. Retract the EHL tendon laterally and the TA tendon medially. Identify the neurovascular bundle and retract it laterally with the EHL tendon. Continue exposure until the anterior capsule is visualized. Perform an anterior capsulotomy via a longitudinal incision. Elevate the capsule and periosteum over the anterior tibia and talus to expose the anterior ankle joint, the tibial plafond, the medial and lateral gutters and the anterior and dorsal talus. Joint Accessibility includes removing any tibial osteophytes from the joint line extending to 1 cm proximal to the joint line. Remove any talar osteophytes which may impede instrumentation entry and placement. If a dorsal boss is noted on the talus, removal of this boss should be performed with a wide, flat osteotome to provide a flush surface.

Figure 134:
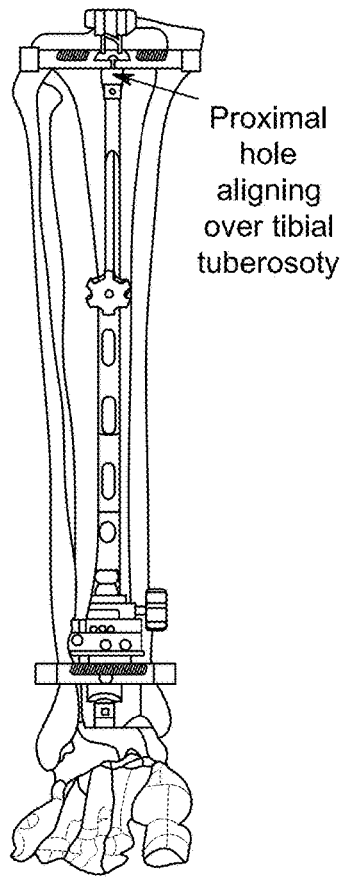

FIG. 134 shows Provisional Fixation. Once the distal tibiotalar joint has been exposed, then based on preference, either establish joint line at surgical site or identify and establish the proximal tuberosity landmark by palpating for the tibial tubercle. Using a pin driver, place a provisional 3.0×100 mm Fluted Steinman Pin into the anterior cortex of the tibia. Anchor the proximal end of the External Alignment Guide by sliding the proximal hole over the tubercle fixation pin. Loosening the Middle Turn Knob counter clockwise by hand, then distract the guide distally until the distal most end of the Alignment Guide is grossly aligned with the tibiotalar joint surgical site.

Figure 135:
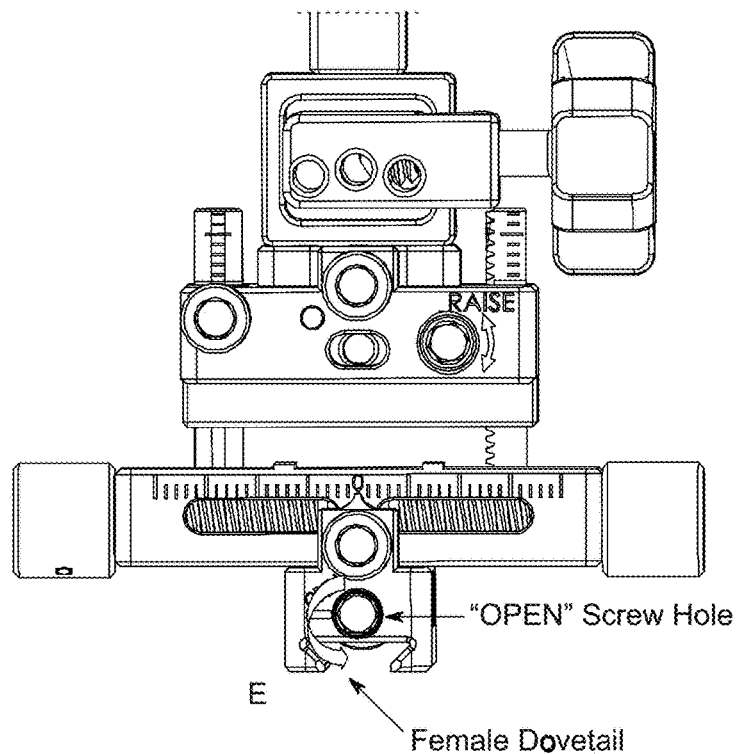

FIG. 135 shows the Distal End of the Alignment Guide. Once grossly aligned over the tibiotalar joint within the surgical site: E) Rotate the "OPEN" screw hole counterclockwise using the hex driver. Insert the male dovetail portion of the I/E Joint Line Reference (JLR) Rod into the female dovetail portion of the Alignment Guide and lock by tightening the "OPEN" screw in a clockwise direction.

Figure 136:
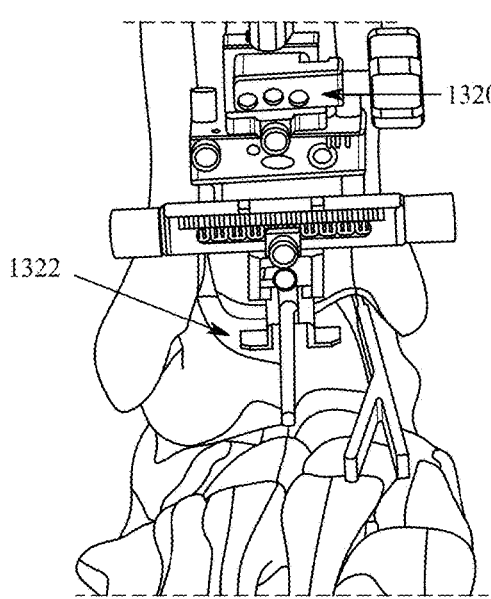
Figure 137:
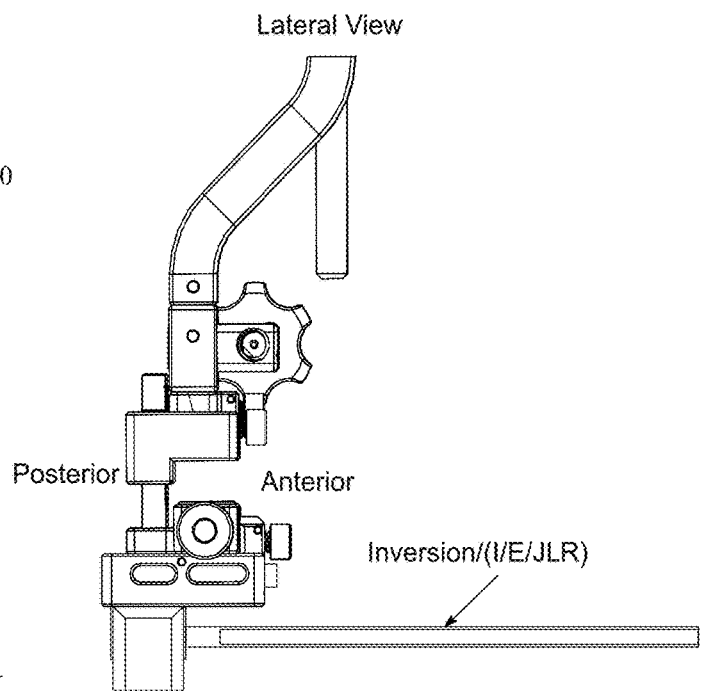

FIGS. 136 and 137 illustrate the Gross Joint Line Height (JLH). Use the JLR portion of the I/E JLR Rod to adjust gross superior/inferior position of the Alignment Guide relative to the joint line. With the proximal hole of the Alignment Guide anchored over the proximal tubercle, now align the distal cluster of three holes 1320 over the anterior tibial crest before establishing slope with 3.0 mm Steinman pin. Confirm that the correct side of the proximal and distal pieces of the Alignment Guide are facing anteriorly, in line with the second metatarsal.

Figure 138:
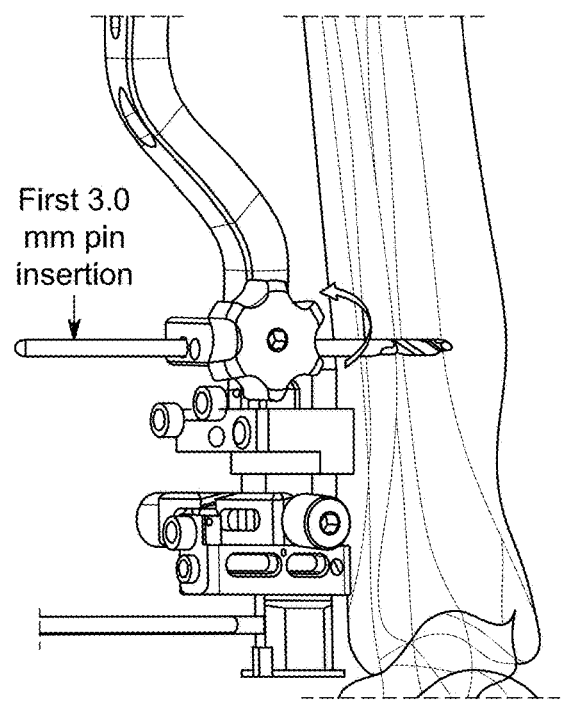

FIG. 138 shows the method of establishing Slope and securing Position of Alignment Guide. With gross JLH and I/E rotation established, place a second 3.0 mm Fluted Steinmann Pin into one of the three distal holes to set slope, selecting the hole that is centered over the anterior crest. Perform a visual check to verify the Fluted Steinmann Pin is as parallel as possible to the I/E JLR Rod in the sagittal plane, then lock the Inferior Turn Knob by hand by turning counterclockwise. In one embodiment, ensure the posterior aspect of the guide is two finger breadths away from the anterior tibia and the distal end of the guide is positioned slightly above the joint line. Take lateral fluoroscopy to check JLH, utilizing optional Angle Wing to verify placement.

Figure 139:
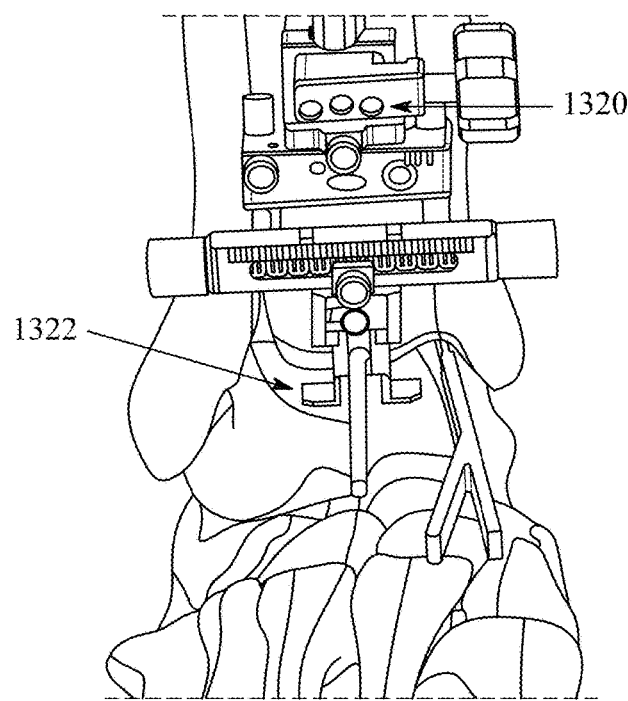

FIG. 139 illustrates assessing Internal—External Rotation. Place the Gutter Alignment Tool 1322 into the medial gutter. Use the JLR Rod to verify I/E rotation against the Gutter Alignment Tool 1322. The tool is designed to allow surgeon preference of I/E rotation. The long axis of the tool indicates medial gutter angulation, while the angled projection indicates 8° of external rotation from the medial gutter, indicating gutter bisection. The surgeon has the option to select preferred I/E rotation given these landmarks.

Figure 140:
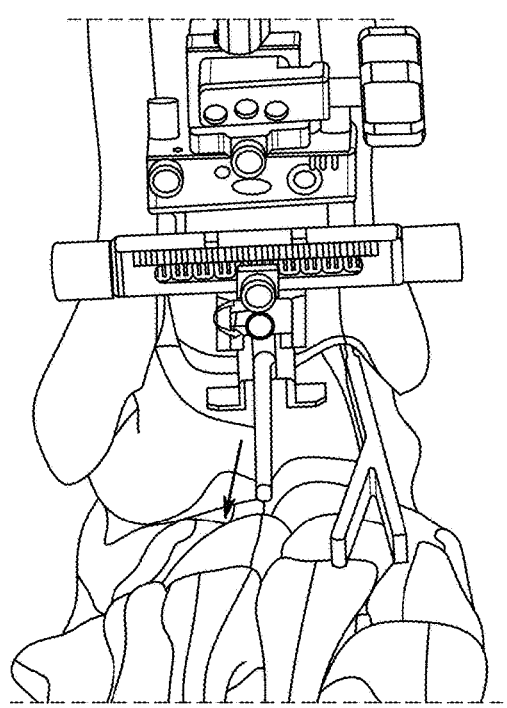
Figure 141:
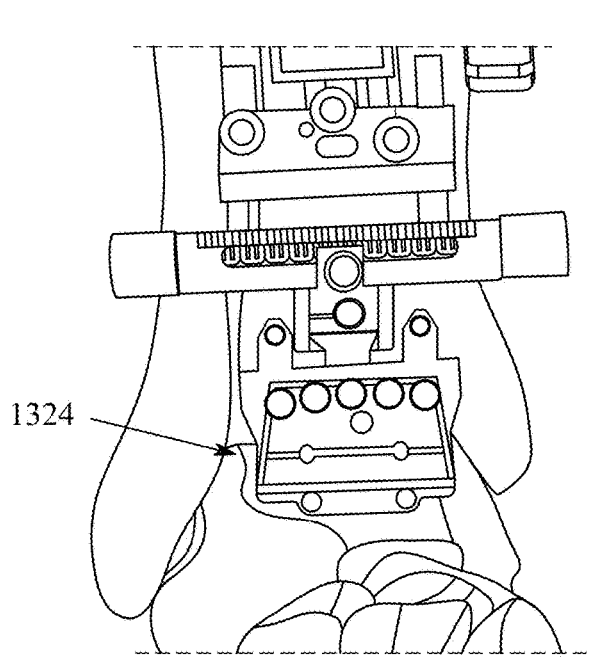

FIGS. 140 and 141 show the Gross Sizing Evaluation. Remove the Gutter Alignment Tool and I/E JLR Rod from the dovetail by rotating the "OPEN" screw counterclockwise and pulling the I/E JLR Rod anteriorly until it is removed from the Alignment Guide. Retrieve the Talar Sizing Resection Block 1324 based on estimated tibial sizing requirements. Based on preference, select from the ARC/Chamfer or FLAT/Flat guide options, then using the hex driver rotate the distal most "OPEN" screw counterclockwise allowing for insertion of the male dovetail portion of the receiving end of the Alignment Guide construct and locking by tightening the "OPEN" screw in a clockwise direction.

Figure 142:
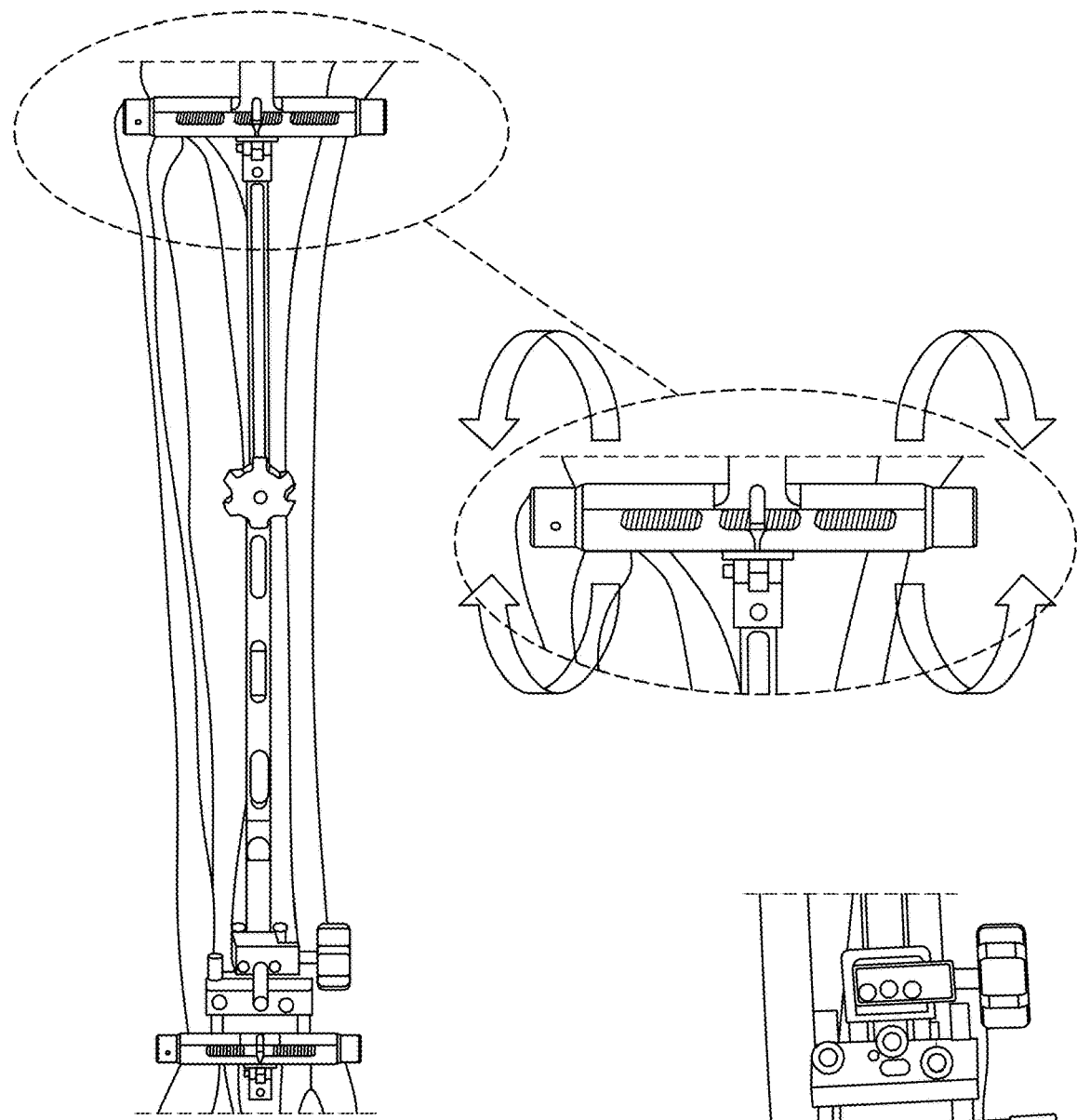
Figure 143:
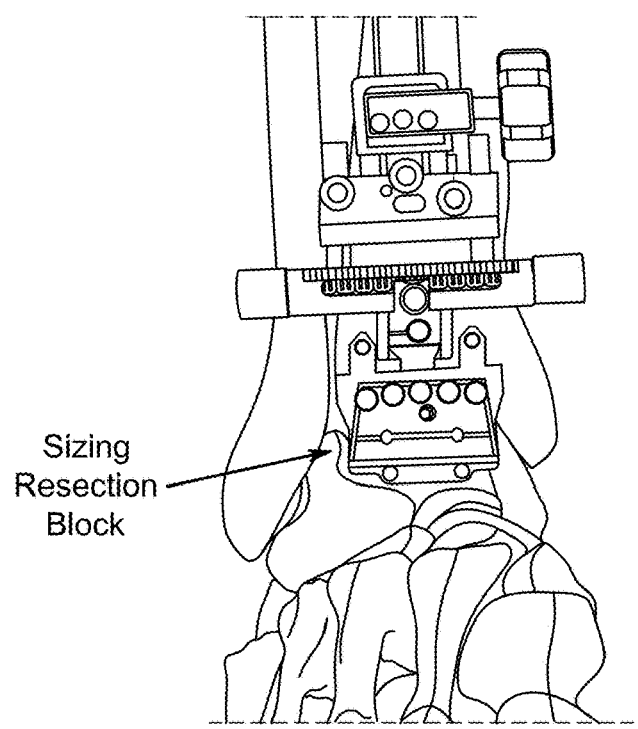

FIGS. 142 and 143 show Gross Varus/Valgus Alignment. Confirm the Sizing Resection Block position using fluoroscopy. Adjust varus/valgus alignment by rotating the proximal small turn knobs forward or backward to adjust varus/valgus position. Repeat AP fluoroscopic view to confirm varus/valgus position of the Sizing Resection Block by comparing the long axis of the tibia with the joint line axis.

Figure 144:
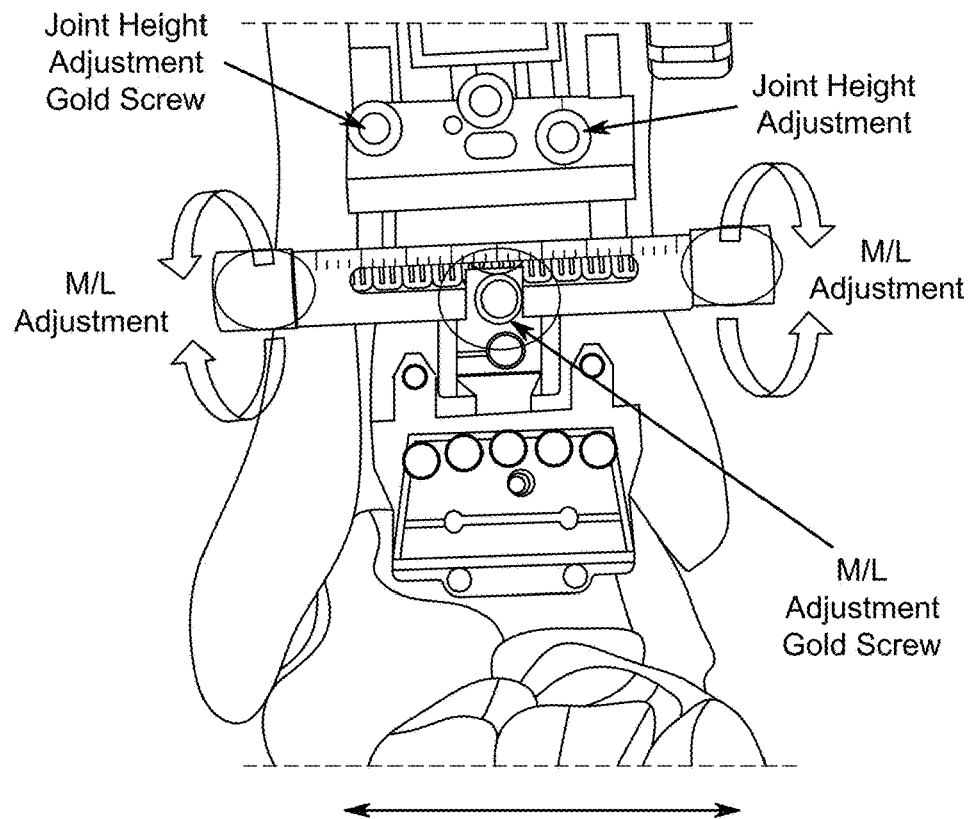

FIG. 144 shows Medial—Lateral Alignment. Adjust medial/lateral (M/L) alignment by rotating the smaller turn knobs counterclockwise (to shift left) or clockwise (to shift right), using fluoroscopy in an AP view to verify the sizing resection block is appropriately aligned with the medial and lateral gutters. Radiolucent alignment markers within the Sizing Resection Block will help evaluate positioning. Lock in M/L alignment by rotating the center most distal most screw clockwise until the threads are fully seated.

Figure 145:
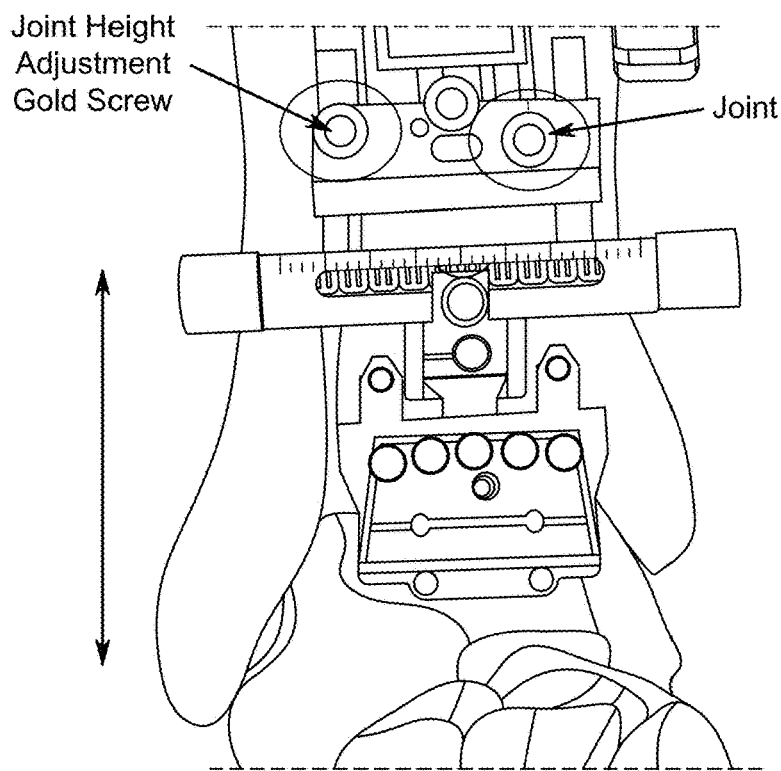

FIG. 145 shows Distal—Proximal Alignment. Unlock the left screw on the Alignment Construct Control Block by rotating it counterclockwise until fully open. Using fluoroscopy under an AP view, evaluate and adjust joint line height by rotating the "RAISE" screw on the right side of the control block clockwise (to raise) or counterclockwise (to lower). Once appropriate positioning has been determined, establish the joint line height by rotating the left screw clockwise until the threads are fully seated.

Figure 146:
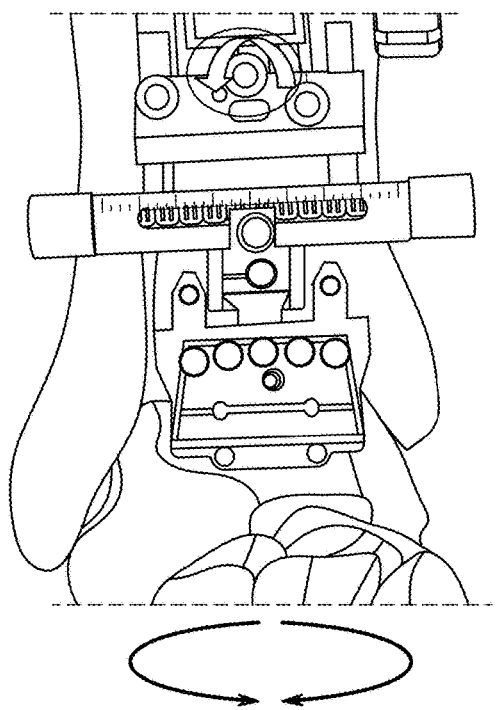

FIG. 146 shows Internal—External Alignment. Confirm internal/external (I/E) position visually. If minor adjustments are needed at this time, remove the sizing resection block by unlocking the "OPEN" screw, and attach the Lateral Alignment Rod. Then unlock the proximal most center screw by rotating it counterclockwise and complete micro adjustments as needed. Once final I/E position is established, lock the distal most screw by rotating clockwise with hex driver.

Figure 147:
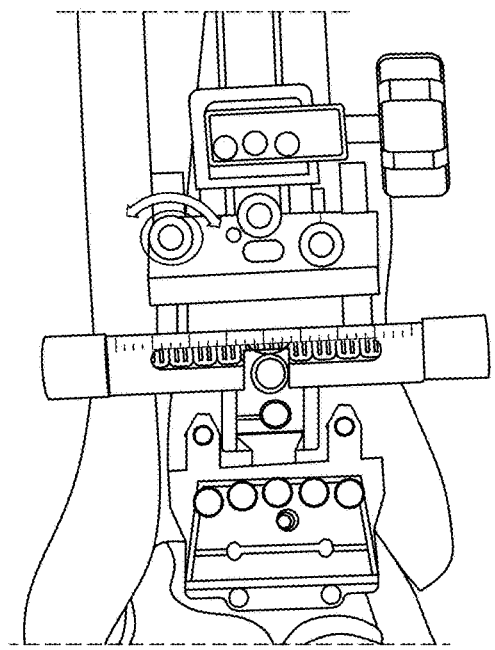
Figures 151, 152:
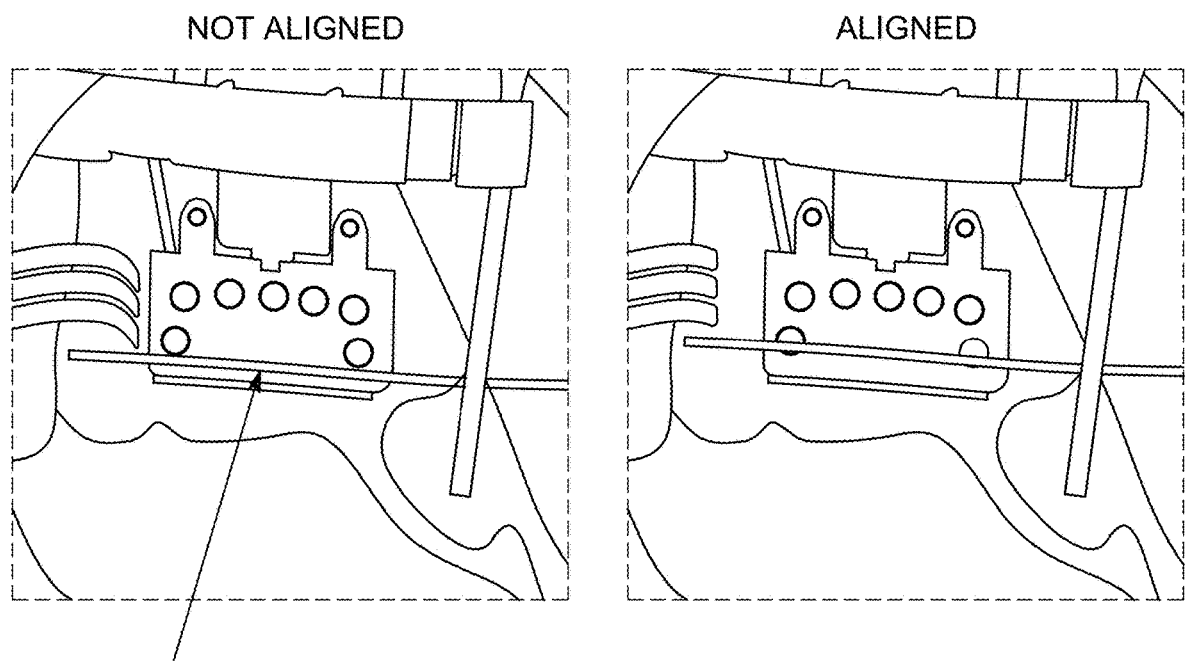

FIGS. 147, 151 and 152 shows Final Joint Line Height Adjustments. If needed, perform final joint line height adjustments at this time. With either the Sizing Resection Block or Lateral Alignment Rod in place, insert the Joint Line Wing into the horizontal slot on the anterior face, then rotate the screw near the "RAISE" laser marking clockwise (to raise) or counterclockwise (to lower) until the radiopaque projection of the Wing is at the joint line or desired joint line. Lock in joint line height by rotating the lateral screw in a clockwise direction. In one embodiment, to ensure a true AP view of the ankle, ensure the Wing projection is overlapping the posterior fluoroscopy marker of the Sizing Resection Block.

Figure 148:
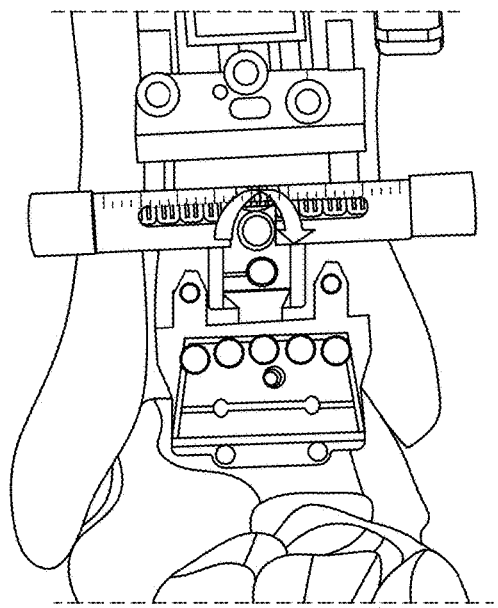
Figure 149:
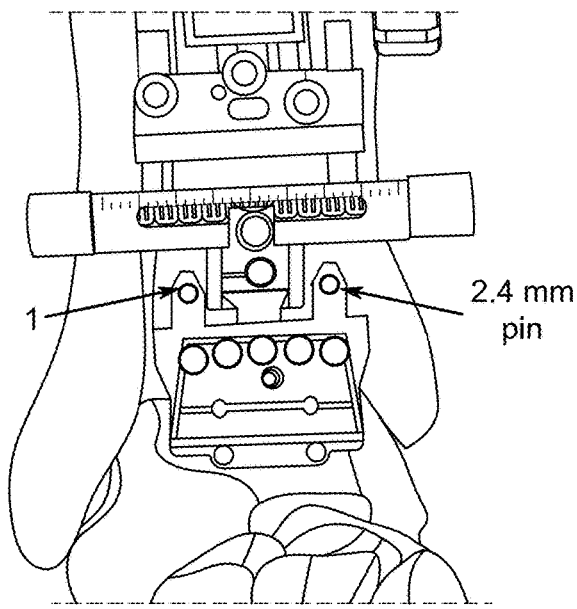
Figure 150:
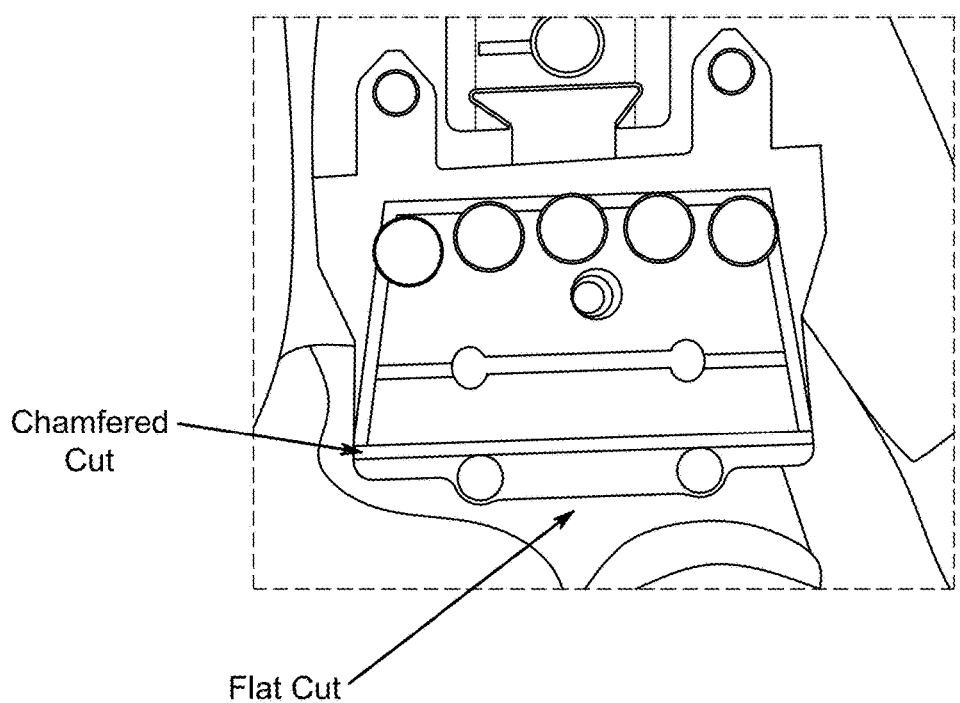

FIGS. 148-150 shows Lock Medial-Lateral Alignment. Perform medial/lateral micro adjustment by rotating the small turn knobs on either side of the Alignment Construct in a clockwise/counterclockwise direction such that the medial corner of the drill holes is above the medial gutter. The lateral corner of the drill holes should be on the tibia near the syndesmosis. If a smaller or larger tibial implant size is necessary, remove the Sizing Resection Block and select the appropriate size and re-insert. Re-adjust the medial/lateral position of the Sizing Resection Block, if necessary. Lock in medial/lateral position by rotating the central distal screw in a clockwise direction. To establish the final position against the tibia, place two 2.4×110 mm Smooth Steinmann Pins into the most proximal M/L holes of the Sizing Resection Block. In one embodiment, cut M/L tibia Steinmann Pins flush with provided Pin Cutters to offset pin depth to allow for easier transfer of tibial sizing resection block during subsequent steps. In one embodiment, with the foot in neutral position, the talar cut height can be assessed at this point, using the Sizing Resection Block. If a chamfered talar cut is preferred, the cut height can be referenced from the proximal slot located on the distal aspect of the Sizing Resection Block. If a flat talar cut is preferred, the cut height can be referenced from the distal edge of the flat cutout between the distal most pin holes.

Referring now to FIGS. 153-161, the method may include tibial joint preparation and tibiotalar joint preparation.

Figure 153:
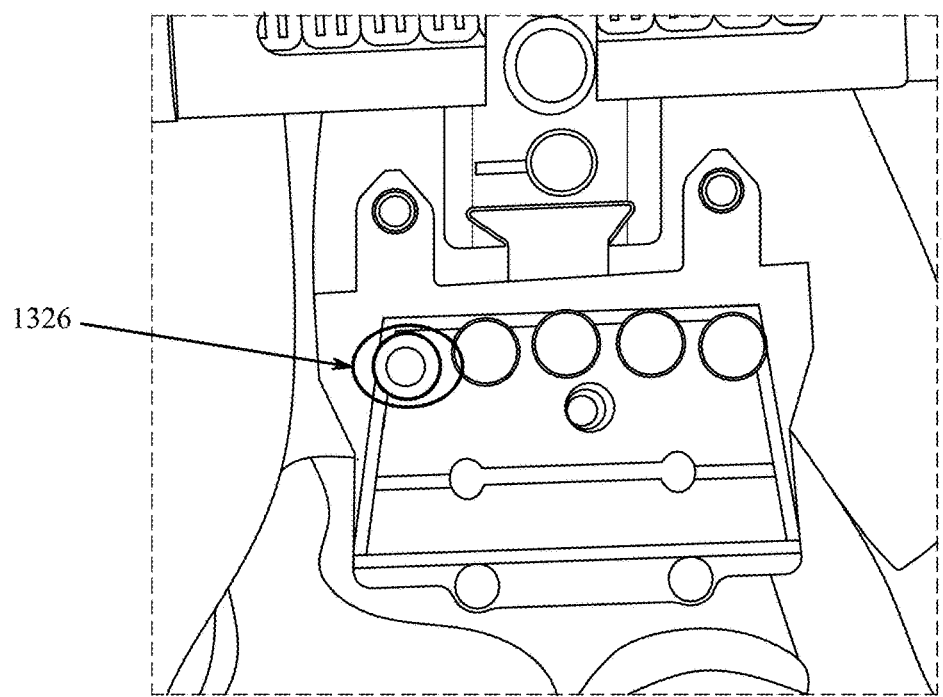

FIG. 153 shows the Bi-cortical ARC™ Resection Drill 1326. Retrieve the 3.5 mm Tibial ARC Resection Drill 1326. Under power, drill bi-cortically into the medial most corner hole of the Sizing Resection Block. Remove the drill and place the 3.5 mm Top Hat in the drilled hole to help secure the position of the block as the remaining holes are drilled. Laser markings on the ARC Resection Drill should be noted and are for reference only. The markings indicate the shortest likely distance the drill will need to travel to achieve bi-cortical drilling.

Figure 154:
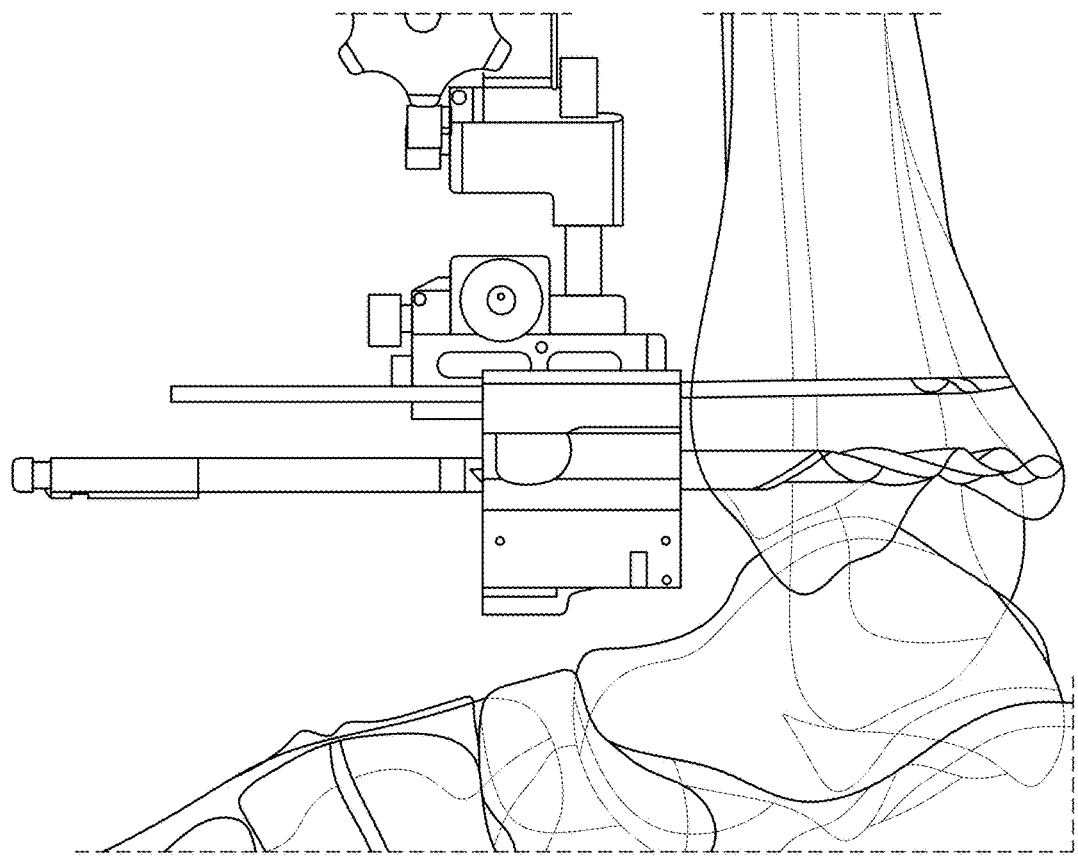

Referring to FIG. 154, performing sequential bi-cortical drilling of the additional holes, using a pecking technique when nearing the posterior cortex to ensure that drilling occurs through the posterior cortex, but does not penetrate beyond is shown. Then remove the Sizing Resection Block by rotating the "OPEN" screw counterclockwise and pulling the Sizing Resection Block off anteriorly. Prior to placing the ARC Tibiotalar Resection Block, ensure that the appropriate tibiotalar resection block style is selected based on the desired talar cut.

Figure 155:
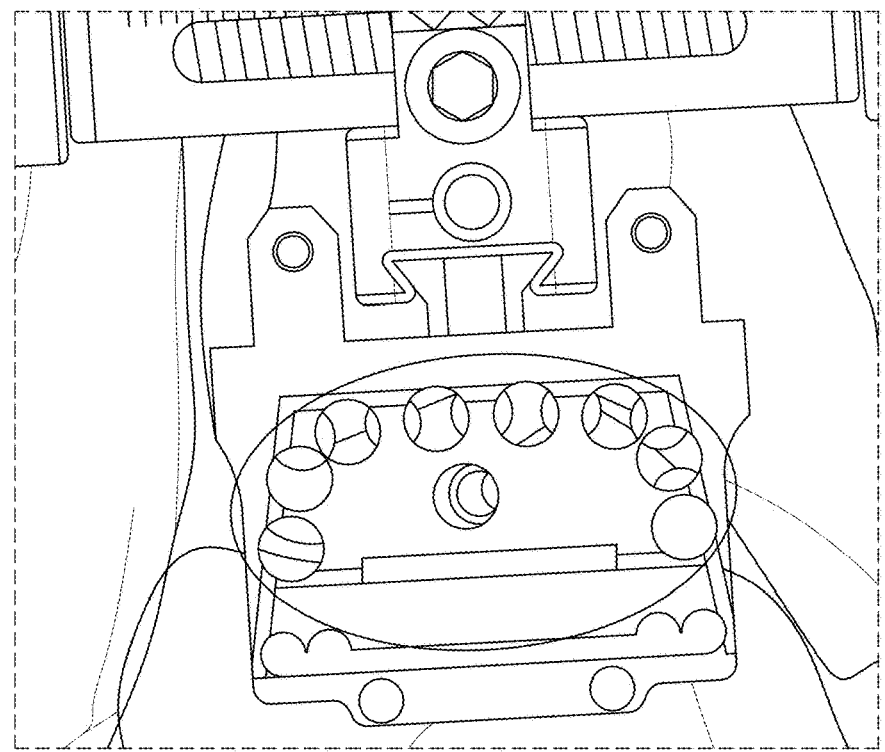

FIG. 155 illustrates that once the Tibiotalar Resection Block style has been selected, slide the proximal portion of the block over the two previously trimmed M/L 2.4 mm guide pins and into the dovetail connection on the Alignment Construct and tighten the "OPEN" screw clockwise to lock in place. Note the overlapping holes. As described above, perform sequential drilling with the 3.5 mm ARC Resection Drill, removing the remaining cortical bone, using a pecking technique when nearing the posterior cortex to ensure that drilling occurs through the posterior cortex, but does not penetrate beyond.

Figure 156:
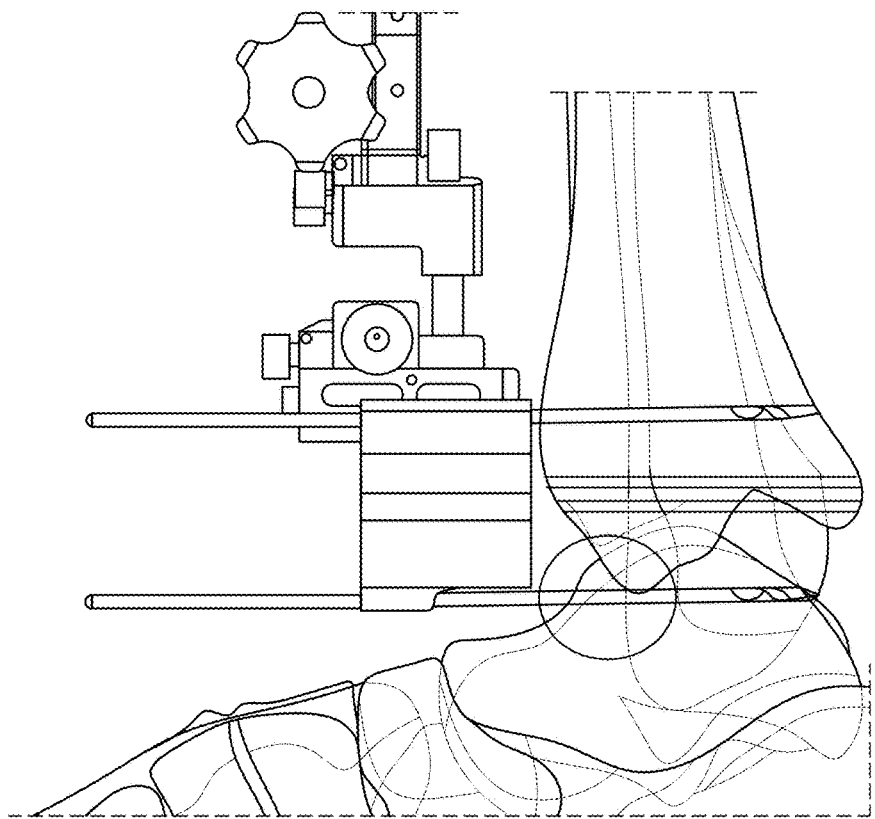

FIG. 156 shows stopping, setting it, and pinning it in Neutral Plantigrade Position. With the foot in neutral, the position of the tibiotalar joint may be held with provisional fixation. Place two 2.4×110 mm Smooth Steinmann Pins into the distal holes of the Tibiotalar Resection Block into the talus. Before completing the dorsal talar table top cut, use a saw blade to evaluate bone resection height. In one embodiment, cut the provisional 2.4 mm talar Steinmann pins flush with provided Pin Cutters to offset pin depth, allowing for easier access of the saw blade in subsequent steps.

Figure 157:
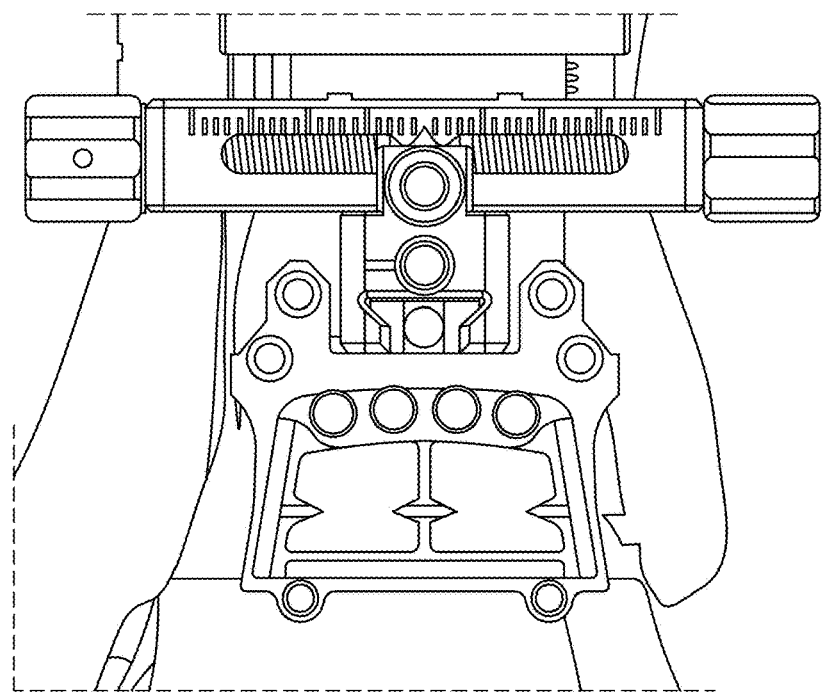

FIG. 157 shows the Preliminary Dorsal Talar Table Top Cut with Bone Preparation. With the 2.4 mm Smooth Steinmann Pins cut flush to the Resection Block, clearance for the saw blade has been achieved. Retrieve the provided 8×90 mm Oscillating Saw Blade to complete the initial dorsal talar table top cut. Cut the superior aspect of the talus through the cutting slot from a medial to lateral direction, then verify accuracy under a lateral fluoroscopy view. In one embodiment, take care to avoid contact of the saw with the medial malleolus and the fibula. Verify all Alignment Construct screws and knobs are still tight after the cut is completed.

Resection Block Removal includes removing the Tibiotalar Resection Block by rotating the "OPEN" screw counterclockwise and pulling the block anteriorly. Remove the 2.4 mm talar pins with the provided Pin Puller. In one embodiment, for larger patients, the saw blade may not fully complete the posterior talar dome cut with Tibiotalar Resection Block in place. In this case, the 13×90 mm Oscillating Saw Blade can be utilized. Insert the saw into the cut portion, and finish the talar cut freehand, ensuring the entire posterior surface is cut from medial to lateral. Remove the talar cut bone from the operative site with the Square Tip Ronguer.

Figure 158:
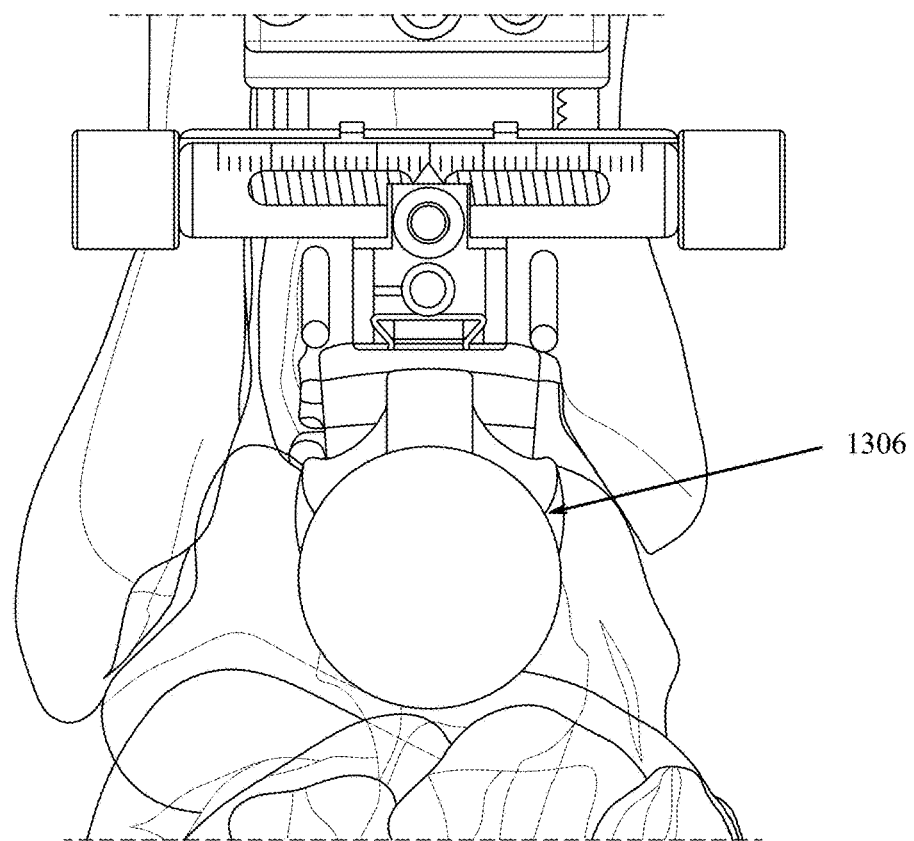

FIG. 158 shows the ARC™ Osteotome—Tibial Planer. Retrieve the ARC™ Osteotome, align the leading edge against the ruffled cortical surface of the tibia, with slight pressure, advance the osteotome forward in a posterior direction, using slight upward pressure to ensure the tibial bone is evenly planed completely from medial to lateral and anterior to posterior. In one embodiment, striking the anterior aspect of the ARC Osteotome with a mallet during this process is NOT recommended. Fine rasping in subsequent steps will help achieve a smooth even surface.

In one embodiment, Tibial Bone Fragment Removal includes once the appropriate tibiofibular ligaments have been completely released, retrieving the curved curette and Kocher forcep. Insert the curved curette lengthwise between the tibia and talus such that the curved portion is parallel to the cut surface of the tibia and talus. Once the curved curette has passed beyond the bone, rotate the curved curette 90° pointing superiorly behind the tibia fragment. Retrieve the Kocher forcep. Insert one side of the Kocher forcep between the tibia and talar cut surfaces and the second side into the tibia cut surface. Ensure that the posterior aspect of the bone is grasped by the Kocher forcep. Using the non-dominant hand, place counter pressure on the central aspect of the lower leg. Using the dominant hand, grip the Kocher forcep and curette. Pull the Kocher forcep and curette together directly anteriorly to retrieve the tibia bone fragment from the tibiotalar joint. Surgical Tip: Retrieve the 6 mm curved osteotome. Use the osteotome to release the Anterior Inferior Tibiofibular Ligament (AITFL), the Interosseous Ligament (IOL) and Posterior Inferior Tibiofibular Ligament (PITFL).

Figure 159:
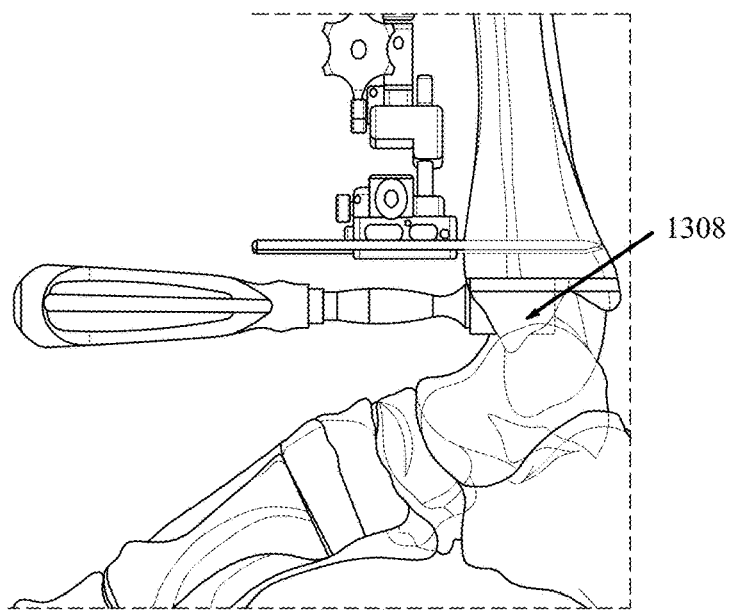

FIG. 159 shows an ARC™ Tibial Rasp. After any remaining posterior fragments from the tibia and talus have been removed, confirm complete bone removal on a lateral view using fluoroscopy. Retrieve the corresponding sized Tibial ARC Rasp. Rasp the tibial cortical surface to ensure that no ridges remain between the drill portions, and that the posterior surface has been fully drilled. In one embodiment, gently push the tibial rasp posteriorly and pull anteriorly to smooth cortical surface, ensuring the rasp remains parallel with the resected distal tibial cortices. Then, manually verify with finger sweep to check for any remaining bone or ridges. For softer bone, using a push ONLY technique is recommended.

Figure 160:
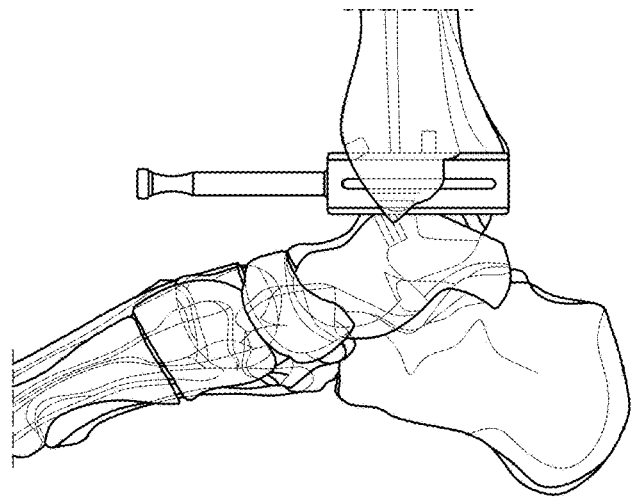

FIGS. 160 and 161 show an ARC™ Tibiotalar Gap Checker. Retrieve the corresponding cut style Tibiotalar Resection Gap Checker, and insert into the resected tibiotalar joint, (i.e. Arc/Chamfer, Flat/Flat, etc. cut style indicator is reflected by laser marking). Ensure the gap checker reaches the posterior aspect of the tibia and that no irregularity exists on fluoroscopy between the bone and the device. If necessary, remove any residual bone fragments that may be contributing to irregularity. Re-insert the Gap Checker to confirm congruent surface between the tibia, Gap Checker and the talus.

After positioning of the full or traditional alignment guide, the method may optionally proceed to any one of the procedures in FIGS. 39-80, as described in greater detail above and which will not be described again here for brevity sake.

Additional instruments for use in the TAR procedure are described in greater detail in U.S. Provisional Application No. 62/779,436, entitled Joint Replacement Systems and Methods of Use and Assembly, which is hereby incorporated by reference in its entirety. Further, the TAR procedure may be completed using patient specific instrumentation, which is described in greater detail in U.S. Provisional Application No. 62/890,611, entitled Patient Specific Instruments and Methods of Use, which is hereby incorporated by reference in its entirety.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A surgical method for total ankle replacement (TAR), comprising:
    obtaining a TAR implant, wherein the TAR implant comprises:
        a tibial component comprising a tibial engagement surface and at least one bone engagement projection;
        a talar component with a talar engagement surface and a talar articulation surface; and
        a tibial insert configured to removably couple with the tibial component and comprising tibial articulation surface that articulates with the talar articulation surface;
    conducting pre-operative templating;
    making an incision to expose an ankle joint with a first tibia bone and a second talar bone;
    continuing the incision while releasing soft tissue, comprising:
        identifying the superficial peroneal nerve and retracting it laterally;
        continuing incision to the extensor retinaculum;
        identifying the extensor hallucis longus (EHL) tendon below the retinaculum;
        dividing the retinaculum longitudinally over the EHL tendon;
        leaving the sheath of the tibialis anterior (TA) tendon intact;
        identifying the neurovascular bundle and retracting it laterally with the EHL tendon;
        retracting the TA tendon medially; and
        continuing incision until the anterior capsule is visualized;
    aligning a joint alignment guide with the first tibia bone;
    preparing the first tibia and second talar bones for receiving the TAR implant, comprising:
        performing an anterior capsulotomy; and
        removing osteophytes on the tibia and the talus;
    coupling a tibial sizing block with a tibial alignment base;
    performing a resection of the first tibia bone to form a resected tibia;
    performing a resection to the second talar bone to form a resected talus;
    trialing the TAR implant with the resected tibia and the resected talus via a TAR trial and guide system to determine sizes for the tibial component, the talar component and the tibial insert; and
    closing the incision.

2. The method of claim 1, wherein the aligning comprises;
    an initial alignment;
    a fine alignment; and
    an additional alignment step.

3. The method of claim 1, wherein making an incision to expose the ankle joint with the first tibia bone and the second talar bone comprises:
    beginning the incision proximal to the ankle joint; and
    terminating the incision distal to the talonavicular joint.

4. The method of claim 1, wherein the TAR trial and guide system comprises:
    a tibial trial and bone preparation first component comprising:
        a base portion comprising a first side with a first tibial engagement surface configured to engage a resected distal tibia of the ankle joint and at least one bone aperture formation guide through hole extending from the first tibial engagement surface to a second tibial insert engagement side; and
        an arm portion extending proximally from an anterior portion of the base portion configured to engage an anterior side of the resected distal tibia; and
    a talar trial and bone preparation second component comprising:
        a first talar engagement surface on a distal side of the second component configured to engage a portion of a resected talus of the ankle joint;
        a posterior trial articulation surface on a proximal side of the second component that is anteriorly-posteriorly arcuately convex;
        an anterior window extending through the second component between the proximal side and the distal side thereof;
        a posterior cut slot extending through the second component between the proximal side and the distal side thereof that is angled posteriorly as it extends from the proximal side to the distal side; and
        a plurality of pin apertures extending through the second component between the proximal side and the distal side.

5. The method of claim 4, further comprising preparing the resected tibia for the implantation of the at least one projection of the tibial component therein, comprising:

coupling the arm portion of the first component to the anterior side of the resected distal tibia with the first tibial engagement surface of the first component engaged with the resected distal tibia; and passing at least one projection of a bone aperture formation instrument though the at least one bone aperture formation guide through hole of the base portion of the first component and into the resected distal tibia to form at least one aperture in the resected distal tibia that is configured to accept the at least one projection of the tibial component therein.

6. The method of claim 5, further comprising preparing the resected talus for coupling with the talar engagement surface of the talar component, comprising:

coupling the second component to the resected distal talus such that the first talar engagement surface of the second component engages a surface portion of the resected talus;

passing a bone cutting instrument through the anterior window of the second component to form an anterior chamfer surface on the resected talus; and passing a bone cutting blade through the posterior cut slot the second component to form a posterior chamfer surface on the resected talus.

7. The method according claim 6, wherein the system further comprises a talar chamfer trial comprising:

a second talar engagement surface on a distal side of the talar chamfer trial configured to engage the surface portion, the anterior chamfer and the posterior chamfer of the resected talus;

a second posterior trial articulation surface on a proximal side of the talar chamfer trial that comprises an anteriorly-posteriorly and medially-laterally arcuately convex portion;

at least one bone aperture formation guide through hole; and a plurality of pin through holes extending between the proximal and distal sides thereof.

8. The method according claim 7, further comprising preparing the resected talus of the ankle joint for the implantation of at least one projection of the talar engagement surface of the talar component therein, comprising:

coupling the second talar engagement surface in engagement with the surface portion, the anterior chamfer and the posterior chamfer of the resected talus by passing a plurality of pins through the plurality of pin through holes and into the resected talus; and passing at least one projection of a bone aperture formation instrument though the at least one bone aperture formation guide through hole of the talar chamfer trial and into the resected talus to form at least one aperture in the resected talus that is configured to accept the at least one projection of the talar component therein.

9. The method according to claim 5, further comprising engaging the first tibial engagement surface of the first component with the resected distal tibia via a distractor system.

10. The method according to claim 9, wherein the distractor system comprises a first pivotable member having a first user engageable arm and an opposite first end;

a second pivotable member having a second user engageable arm and an opposite end, said first pivotable member pivotably connected to said second pivotable member between said user engageable arms and said ends;

a first connecting member having a first end and a second end, said first end pivotally connected to said first end of said first pivotable member;

a second connecting member having a first end and a second end, said first end pivotally connected to said second end of said second pivotable member;

a biasing member for biasing said first arm away from said second arm so that said second end of said first connecting member is biased towards said second end of said second member; and at least one detachable tool comprising a body having a proximal portion and a distal portion, said proximal portion being releasably attachable to at least one of said second end of said first connection member and/or said second end of said second connecting member, said distal portion being operably positionable between the resected tibia and the resected talus.

11. The method according to claim 6, further comprising engaging the first talar engagement surface of the second component with the surface portion of the resected talus via a distractor system.

12. The method according to claim 11, wherein the distractor system comprises a first pivotable member having a first user engageable arm and an opposite first end;

a second pivotable member having a second user engageable arm and an opposite end, said first pivotable member pivotably connected to said second pivotable member between said user engageable arms and said ends;

a first connecting member having a first end and a second end, said first end pivotally connected to said first end of said first pivotable member;

a second connecting member having a first end and a second end, said first end pivotally connected to said second end of said second pivotable member;

a biasing member for biasing said first arm away from said second arm so that said second end of said first connecting member is biased towards said second end of said second member; and at least one detachable tool comprising a body having a proximal portion and a distal portion, said proximal portion being releasably attachable to at least one of said second end of said first connection member and/or said second end of said second connecting member, said distal portion being operably positionable between the resected tibia and the resected talus.

13. The method according claim 1, wherein performing the resection of the first tibia bone to form the resected tibia comprises utilizing a resection guide.

14. The method according claim 13, wherein the resection guide comprises:

a body having a first side and an opposite second side;

said body having a plurality of alignment pin through-holes extending from said first side to said second side of said body with openings on said first side of said body and openings on said second side of said body;

said body having a plurality of guide through-holes extending from said first side to said second side to define a first pattern of guide through-holes with openings on said first side of said body and openings on said second side of said body; and wherein when said plurality of alignment pin through-holes of said body is supported on a plurality of alignment pins attached to the first tibia bone, said openings of the guide through-holes on said second side of said body face the first tibia bone and said openings of the guide through-holes on said first side face away from said first tibia bone so that said first pattern of guide through-holes is operable for receiving a drill for use in resecting the at least a portion of the first tibia bone.

15. The method according claim 14, wherein performing a resection of the first tibia bone to form a resected tibia comprises:
supporting the resection guide on a plurality of alignment pins attached to the first tibia bone, the resection guide having the first pattern of guide through-holes; and
guiding a drill through the plurality of guide through-holes in the resection guide and into at least a portion of the first tibia bone.

16. The method according claim 15, further comprising:
removing the resection guide from the plurality of alignment pins attached to the first tibia bone;
supporting a second resection guide on the plurality of alignment pins attached to the first tibia bone, the second resection guide having a second pattern of guide through-holes offset from the first pattern; and
guiding a drill through the plurality of guide through-holes in the second resection guide and into at least a portion of the first tibia bone.

17. The method according claim 16, further comprising:
removing the second resection guide from the plurality of alignment pins attached to the first tibia bone;
supporting a sweeping reamer on the plurality of alignment pins attached to the first tibia bone, the sweeping reamer having an elongated slot; and
guiding a reamer through the elongated slot in the sweeping reamer and into the portion of the first tibia bone.

18. The method according claim 17, wherein:
the supporting the resection guide on the plurality of alignment pins attached to the first tibia bone comprises supporting the resection guide on a first plurality of pins attached to a tibia of the patient and a second plurality of pins attached to a talus of the patient;
the guiding the drill through the plurality of guide through-holes in the resection guide is into the tibia of the patient; and
the resection guide includes a slot, and further comprising guiding a cutting tool in the slot and into the talus of the patient.

19. A surgical method for total ankle replacement (TAR), comprising:
obtaining a TAR implant, wherein the TAR implant comprises:
a tibial component comprising a tibial engagement surface and at least one bone engagement projection;
a talar component with a talar engagement surface and a talar articulation surface; and
a tibial insert configured to removably couple with the tibial component and comprising tibial articulation surface that articulates with the talar articulation surface;
conducting pre-operative templating;
making an incision to expose an ankle joint with a first tibia bone and a second talar bone;
aligning a joint alignment guide with the first tibia bone;
preparing the first tibia and second talar bones for receiving the TAR implant;
coupling a tibial sizing block with a tibial alignment base;
performing a resection of the first tibia bone to form a resected tibia;
performing a resection to the second talar bone to form a resected talus;
trialing the TAR implant with the resected tibia and the resected talus via a TAR trial and guide system to determine sizes for the tibial component, the talar component, and the tibial insert, wherein the TAR trial and guide system comprises:
a tibial trial and bone preparation first component comprising:
a base portion comprising a first side with a first tibial engagement surface configured to engage a resected distal tibia of the ankle joint and at least one bone aperture formation guide through hole extending from the first tibial engagement surface to a second tibial insert engagement side; and
an arm portion extending proximally from an anterior portion of the base portion configured to engage an anterior side of the resected distal tibia; and
a talar trial and bone preparation second component comprising:
a first talar engagement surface on a distal side of the second component configured to engage a portion of a resected talus of the ankle joint;
a posterior trial articulation surface on a proximal side of the second component that is anteriorly-posteriorly arcuately convex;
an anterior window extending through the second component between the proximal side and the distal side thereof;
a posterior cut slot extending through the second component between the proximal side and the distal side thereof that is angled posteriorly as it extends from the proximal side to the distal side; and
a plurality of pin apertures extending through the second component between the proximal side and the distal side;
preparing the resected tibia for the implantation of the at least one projection of the tibial component therein, comprising:
coupling the arm portion of the first component to the anterior side of the resected distal tibia with the first tibial engagement surface of the first component engaged with the resected distal tibia; and
passing at least one projection of a bone aperture formation instrument though the at least one bone aperture formation guide through hole of the base portion of the first component and into the resected distal tibia to form at least one aperture in the resected distal tibia that is configured to accept the at least one projection of the tibial component therein; and
closing the incision.

20. A surgical method for total ankle replacement (TAR), comprising:
obtaining a TAR implant, wherein the TAR implant comprises:
a tibial component comprising a tibial engagement surface and at least one bone engagement projection;
a talar component with a talar engagement surface and a talar articulation surface; and
a tibial insert configured to removably couple with the tibial component and comprising tibial articulation surface that articulates with the talar articulation surface;
conducting pre-operative templating;
making an incision to expose an ankle joint with a first tibia bone and a second talar bone;
aligning a joint alignment guide with the first tibia bone;

preparing the first tibia and second talar bones for receiving the TAR implant;
coupling a tibial sizing block with a tibial alignment base;
performing a resection of the first tibia bone to form a resected tibia comprises utilizing a resection guide, wherein the resection guide comprises:
  a body having a first side and an opposite second side;
  said body having a plurality of alignment pin through-holes extending from said first side to said second side of said body with openings on said first side of said body and openings on said second side of said body;
  said body having a plurality of guide through-holes extending from said first side to said second side to define a first pattern of guide through-holes with openings on said first side of said body and openings on said second side of said body; and
  wherein when said plurality of alignment pin through-holes of said body is supported on a plurality of alignment pins attached to the first tibia bone, said openings of the guide through-holes on said second side of said body face the first tibia bone and said openings of the guide through-holes on said first side face away from said first tibia bone so that said first pattern of guide through-holes is operable for receiving a drill for use in resecting the at least a portion of the first tibia bone;
wherein performing a resection of the first tibia bone to form a resected tibia comprises:
  supporting the resection guide on a plurality of alignment pins attached to the first tibia bone, the resection guide having the first pattern of guide through-holes;
  guiding a drill through the plurality of guide through-holes in the resection guide and into at least a portion of the first tibia bone;
  removing the resection guide from the plurality of alignment pins attached to the first tibia bone;
  supporting a second resection guide on the plurality of alignment pins attached to the first tibia bone, the second resection guide having a second pattern of guide through-holes offset from the first pattern; and
  guiding a drill through the plurality of guide through-holes in the second resection guide and into at least a portion of the first tibia bone;
performing a resection to the second talar bone to form a resected talus;
trialing the TAR implant with the resected tibia and the resected talus via a TAR trial and guide system to determine sizes for the tibial component, the talar component and the tibial insert; and
closing the incision.

* * * * *